United States Patent
Miyashita et al.

(10) Patent No.: US 12,084,397 B2
(45) Date of Patent: Sep. 10, 2024

(54) ORGANIC COMPOUND, ORGANIC LIGHT-EMITTING ELEMENT, DISPLAY APPARATUS, PHOTOELECTRIC CONVERSION APPARATUS, ELECTRONIC APPARATUS, LIGHTING APPARATUS, MOVING OBJECT, AND EXPOSURE LIGHT SOURCE

(71) Applicant: CANON KABUSHIKI KAISHA, Tokyo (JP)

(72) Inventors: Hirokazu Miyashita, Ebina (JP); Naoki Yamada, Inagi (JP); Satoru Shiobara, Hiratsuka (JP); Isao Kawata, Kawasaki (JP); Yuto Ito, Kokubunji (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 257 days.

(21) Appl. No.: 17/010,647

(22) Filed: Sep. 2, 2020

(65) Prior Publication Data

US 2021/0070677 A1 Mar. 11, 2021

(30) Foreign Application Priority Data

Sep. 5, 2019 (JP) ................. 2019-162082

(51) Int. Cl.
*C07C 13/62* (2006.01)
*H10K 85/60* (2023.01)

(52) U.S. Cl.
CPC ............. *C07C 13/62* (2013.01); *H10K 85/60* (2023.02)

(58) Field of Classification Search
None
See application file for complete search history.

(56) References Cited

U.S. PATENT DOCUMENTS

| | | | |
|---|---|---|---|
| 2010/0026171 A1 | 2/2010 | Negishi | |
| 2011/0024737 A1* | 2/2011 | Horiuchi ................. | C07C 43/21 585/27 |
| 2013/0033416 A1 | 2/2013 | Kamatani | |
| 2016/0035982 A1* | 2/2016 | Itabashi ................... | C07C 13/62 585/27 |
| 2020/0403173 A1* | 12/2020 | Miyashita ........... | H01L 51/5221 |

FOREIGN PATENT DOCUMENTS

| | | |
|---|---|---|
| CN | 102245546 A | 11/2011 |
| CN | 112441949 A | 3/2021 |
| DE | 10 2019 108200 A1 | 10/2019 |
| EP | 2314558 B1 | 5/2014 |
| EP | 2379473 B1 | 2/2017 |
| JP | H11-040360 A | 2/1999 |
| JP | 2009-221180 A | 10/2009 |
| JP | 2010-143879 A | 7/2010 |
| JP | 2010-254610 A | 11/2010 |
| JP | 2012-246258 A | 12/2012 |
| JP | 2016015388 A * | 1/2016 |
| JP | 2018-76259 A | 5/2018 |
| JP | 2020-026406 A | 2/2020 |
| JP | 2021-038187 A | 3/2021 |
| WO | 2007/099802 A1 | 9/2007 |
| WO | 2008/120806 A1 | 10/2008 |
| WO | 2010/071224 A1 | 6/2010 |
| WO | 2013/042357 A1 | 3/2013 |
| WO | 2014125970 A1 | 8/2014 |

(Continued)

OTHER PUBLICATIONS

Machine translation JP2016015388A, Jan. 28, 2016, pp. 1-25 (Year: 2016).*

Wu, Tsun-Cheng et al., "Synthesis and Structural Analysis of a Highly Curved Buckybowl Containing Corannulene and Sumanene Fragments", Journal of the American Chemical Society, 2011, pp. 16319-16321, vol. 133, No. 41.

Wu, Tsun-Cheng et al., "Bowl-Shaped Fragments of C70 or Higher Fullerenes: Synthesis, Structural Analysis, and Inversion Dynamics", Angewandte Chemie, International Edition, 2013, pp. 1289-1293, vol. 52, No. 4.

(Continued)

*Primary Examiner* — Medhanit W Bahta
(74) *Attorney, Agent, or Firm* — Canon U.S.A., Inc. I.P. Division

(57) ABSTRACT

An organic compound represented by formula [1] is provided.

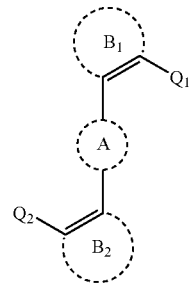

[1]

Ring A is a polycyclic aromatic hydrocarbon ring having a fluoranthene skeleton and having 16 to 60 carbon atoms and optionally has, as a substituent, a substituted or unsubstituted alkyl group or the like. Rings $B_1$ and $B_2$ are aromatic hydrocarbon rings having 6 to 18 carbon atoms and each have two or more electron withdrawing groups. $Q_1$ and $Q_2$ respectively represent one of the electron withdrawing groups of the ring $B_1$ and one of the electron withdrawing groups of the ring $B_2$, and are respectively located at an ortho position of the ring $B_1$ and at an ortho position of the ring $B_2$ with respect to the ring A.

18 Claims, 8 Drawing Sheets

(56) References Cited

FOREIGN PATENT DOCUMENTS

WO      2018/179482  A1    10/2018
WO      2021/085131  A1    5/2021

OTHER PUBLICATIONS

Schmidt, Bernd M. et al., "Fluorinated and Trifluoromethylated Corannulenes", Chemistry—A European Journal, 2013, pp. 13872-13880, vol. 19, No. 41.

\* cited by examiner

FIG. 1

| COMPOUND | STRUCTURE | MOLECULAR WEIGHT | VERTICAL DIRECTION OF MOLECULE | PLANAR DIRECTION OF MOLECULE | DIHEDRAL ANGLE(°) | DECOMPOSITION TEMPERATURE - SUBLIMATION TEMPERATURE (°C) |
|---|---|---|---|---|---|---|
| COMPARATIVE COMPOUND (6) | 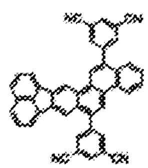 | 604.67 | | | 56 | 60 |
| EXEMPLARY COMPOUND A17 | 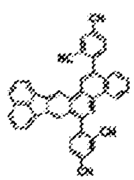 | 604.67 | | | 70 | 90 |

ORGANIC COMPOUND, ORGANIC LIGHT-EMITTING ELEMENT, DISPLAY APPARATUS, PHOTOELECTRIC CONVERSION APPARATUS, ELECTRONIC APPARATUS, LIGHTING APPARATUS, MOVING OBJECT, AND EXPOSURE LIGHT SOURCE

BACKGROUND OF THE INVENTION

Field of the Invention

The present disclosure relates to an organic compound, an organic light-emitting element, a display apparatus, a photoelectric conversion apparatus, an electronic apparatus, a lighting apparatus, a moving object, and an exposure light source.

Description of the Related Art

Organic light-emitting elements, in particular, organic electroluminescent elements (hereafter may be referred to as "organic EL elements") are electronic elements including a pair of electrodes and an organic compound layer disposed between the electrodes. By injecting electrons and holes through the pair of electrodes, excitons of a luminescent organic compound in the organic compound layer are generated. The organic light-emitting elements emit light when the excitons return to their ground state.

Recent remarkable progress in organic light-emitting elements can achieve low driving voltage, various emission wavelengths, high-speed response, and reductions in the thickness and weight of light-emitting devices.

Luminescent organic compounds have been enthusiastically created to date. This is because it is important to create compounds having good light-emitting properties in order to provide high-performance organic light-emitting elements. Japanese Patent Laid-Open No. 11-40360 discloses a compound 1-A below as a compound that has been created so far.

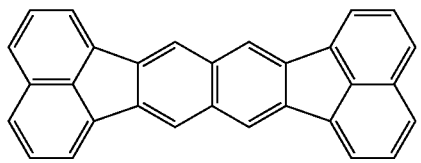

1-A

Studies conducted by the present inventors reveal that the compound 1-A has a low oxidation potential and the compound itself has low stability as described later. Therefore, organic light-emitting elements including this compound have poor durability.

SUMMARY OF THE INVENTION

The present disclosure provides an organic compound having a high oxidation potential and high chemical stability. The present disclosure also provides an organic light-emitting element having high driving durability.

An organic compound according to an aspect of the present disclosure is represented by formula [1] below.

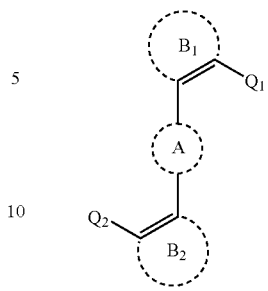

[1]

In the formula [1], ring A is a polycyclic aromatic hydrocarbon ring having a fluoranthene skeleton and having 16 to 60 carbon atoms and optionally has, as a substituent, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, or a silyl group.

Rings $B_1$ and $B_2$ are aromatic hydrocarbon rings having 6 to 18 carbon atoms and each have two or more electron withdrawing groups.

$Q_1$ and $Q_2$ respectively represent one of the electron withdrawing groups of the ring $B_1$ and one of the electron withdrawing groups of the ring $B_2$, and are respectively located at an ortho position of the ring $B_1$ and at an ortho position of the ring $B_2$ with respect to the ring A.

Further features of the present disclosure will become apparent from the following description of exemplary embodiments with reference to the attached drawings.

BRIEF DESCRIPTION OF THE DRAWINGS

FIG. 1 shows a structure of an exemplary compound A17 according to an embodiment of the present disclosure.

DESCRIPTION OF THE EMBODIMENTS

Organic Compound

Figure 2:
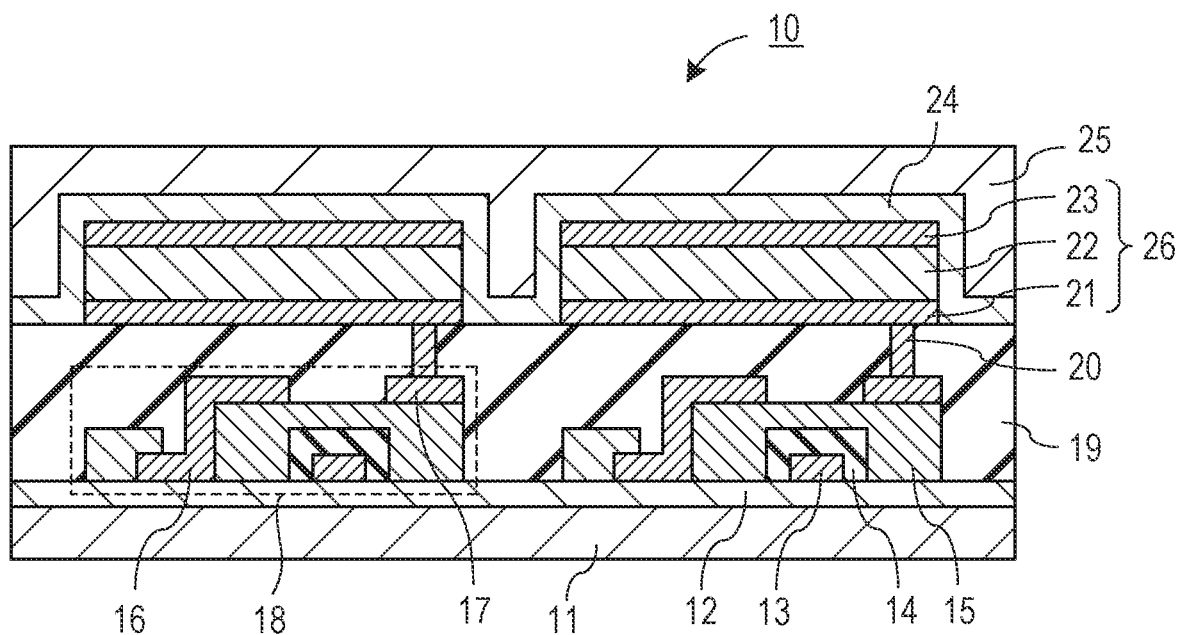
FIG. 2 is a schematic sectional view illustrating an example of a display apparatus including an organic light-emitting element according to an embodiment of the present disclosure.

First, an organic compound according to this embodiment will be described. The organic compound according to this embodiment is an organic compound represented by general formula [1] below.

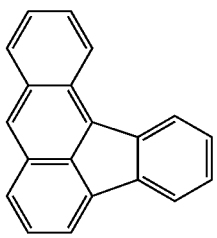

[1]

In the formula [1], the ring A is a polycyclic aromatic hydrocarbon ring having a fluoranthene skeleton and having 16 to 60 carbon atoms, such as 16 to 40 carbon atoms.

The ring A is, for example, FF1 to FF42 below, but is not limited thereto. The ring A may be FF1 to FF16.

FF1

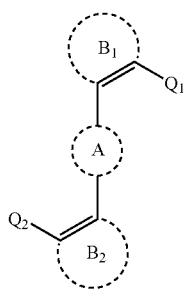

FF2

FF3

FF4

FF5

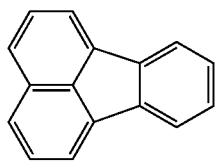

FF6

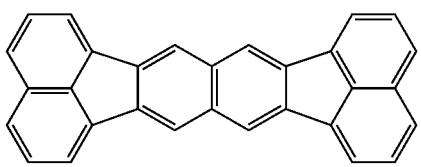

FF7

FF8

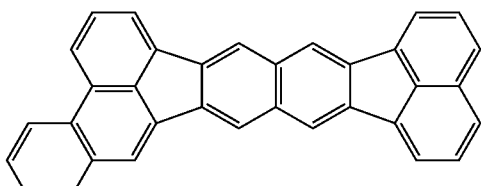

FF9

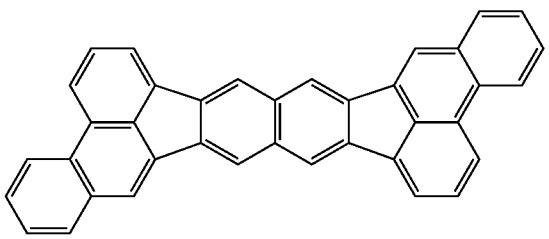

FF10

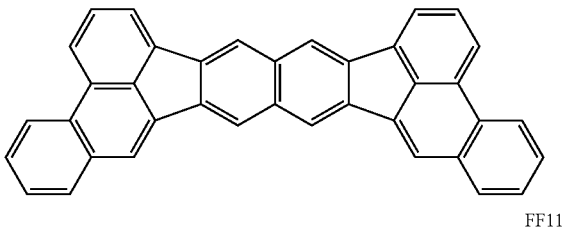

FF11

FF12

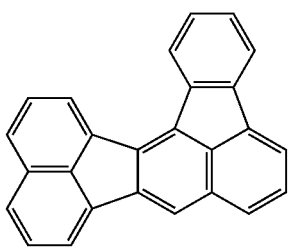

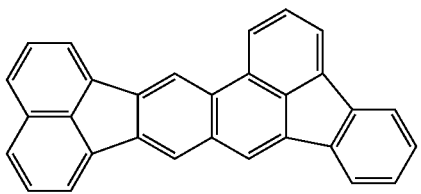

FF13
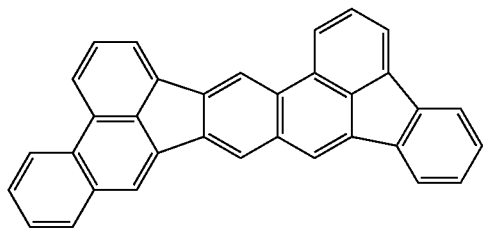
FF14
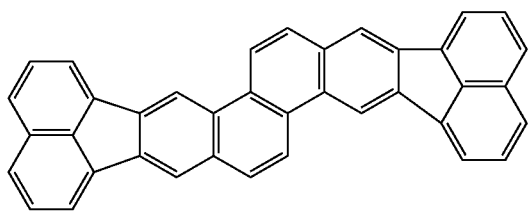
FF15
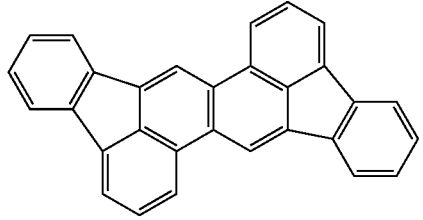
FF16
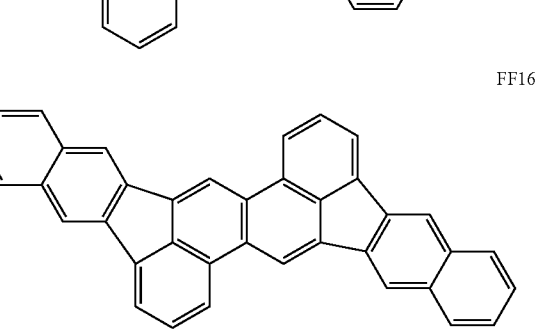
FF17
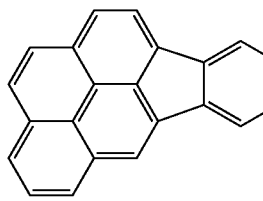
FF18
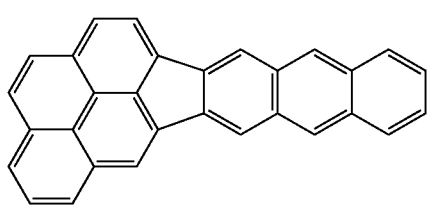
FF19
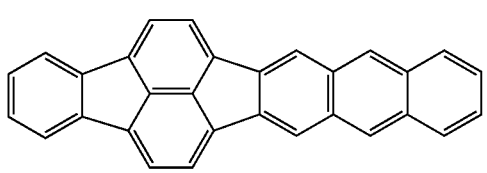
FF20
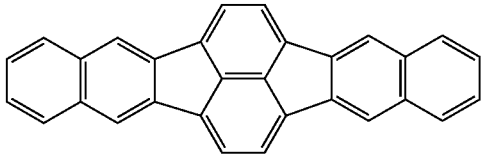
FF21
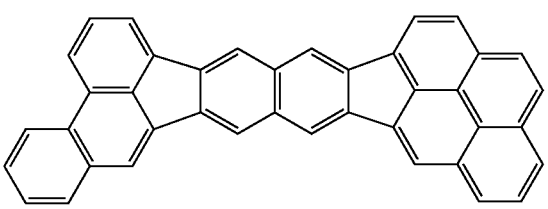
FF22
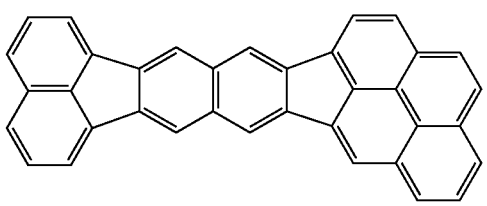
FF23
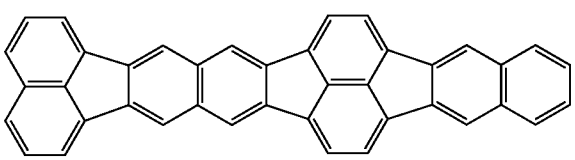
FF24
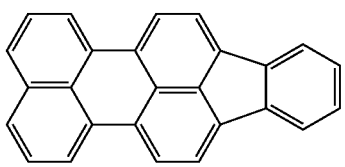
FF25
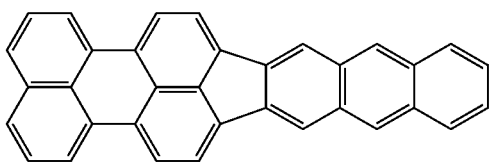
FF26
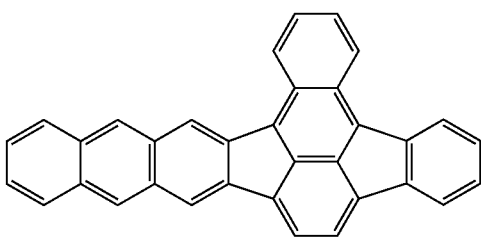
FF27
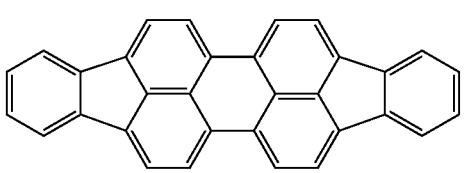

FF28
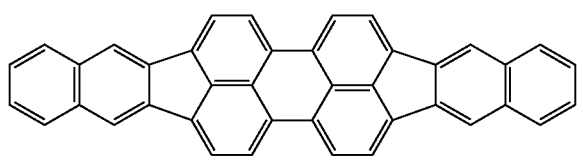

FF36
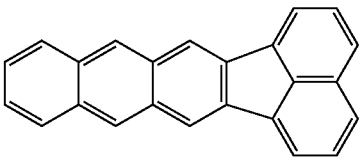

FF29
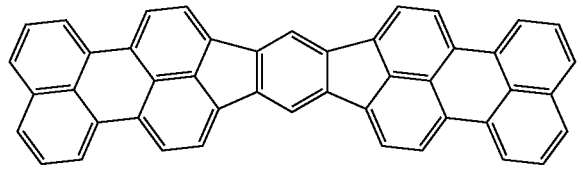

FF37
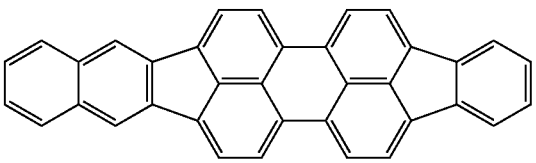

FF30
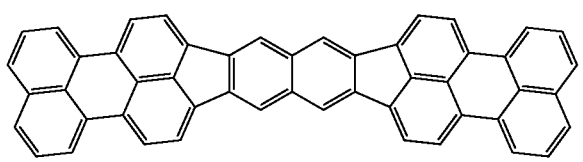

FF38
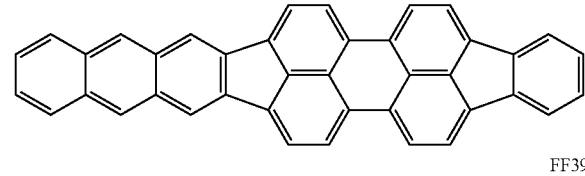

FF31
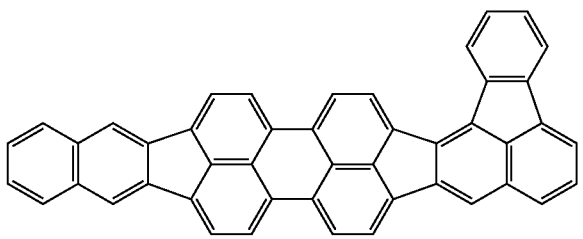

FF39
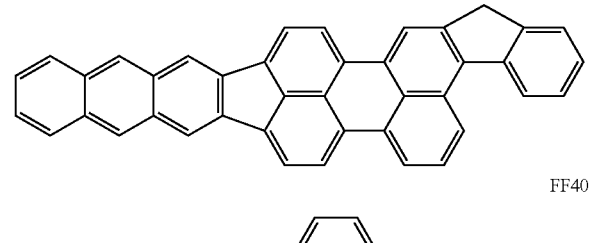

FF32
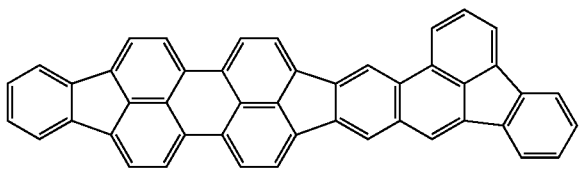

FF40
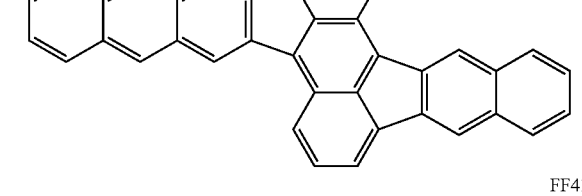

FF33
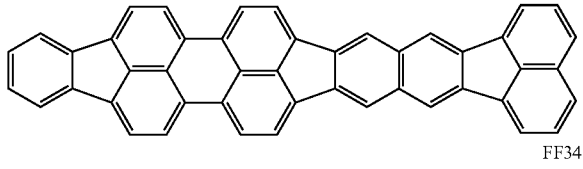

FF41
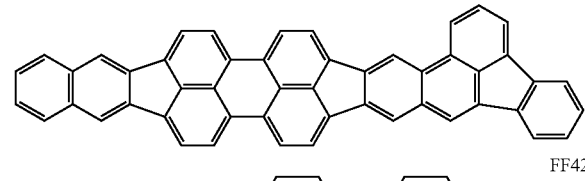

FF34
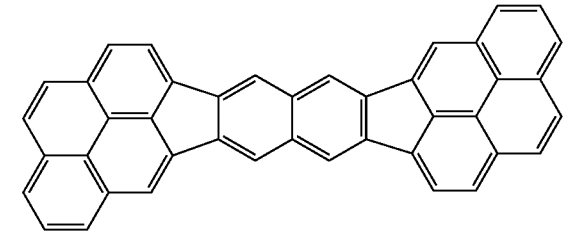

FF42
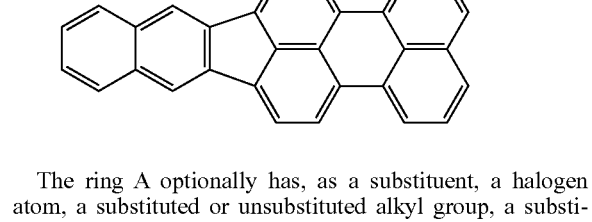

FF35
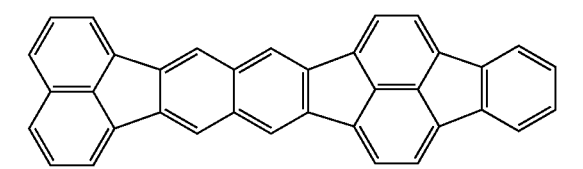

The ring A optionally has, as a substituent, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, and a silyl group.

Non-limiting examples of the halogen atom that is optionally included in the ring A as a substituent include fluorine, chlorine, bromine, and iodine.

Non-limiting examples of the alkyl group that is optionally included in the ring A as a substituent include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group. The alkyl group that is optionally included in the ring A as a substituent is, for example, an alkyl group having 1 to 10 carbon atoms.

Non-limiting examples of the alkoxy group that is optionally included in the ring A as a substituent include a methoxy group, an ethoxy group, a propoxy group, an 2-ethyloctyloxy group, and a benzyloxy group. The alkoxy group that is optionally included in the ring A as a substituent is, for example, an alkoxy group having 1 to 6 carbon atoms.

Non-limiting examples of the amino group that is optionally included in the ring A as a substituent include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, and an N-piperidyl group.

Non-limiting examples of the aryl group that is optionally included in the ring A as a substituent include a phenyl group, a naphthyl group, an indenyl group, a biphenyl group, a terphenyl group, fluorenyl group, a phenanthryl group, a fluoranthenyl group, and a triphenylenyl group. The aryl group that is optionally included in the ring A as a substituent is, for example, an aryl group having 6 to 18 carbon atoms.

Non-limiting examples of the heterocyclic group that is optionally included in the ring A as a substituent include a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group. The heterocyclic group that is optionally included in the ring A as a substituent is, for example, a heterocyclic group having 3 to 15 carbon atoms.

Non-limiting examples of the aryloxy group that is optionally included in the ring A as a substituent include a phenoxy group and a thienyloxy group.

Non-limiting examples of the silyl group that is optionally included in the ring A as a substituent include a trimethylsilyl group and a triphenylsilyl group.

Non-limiting examples of a substituent that may be further introduced to the alkyl group, the alkoxy group, the amino group, the aryl group, the heterocyclic group, and the aryloxy group include alkyl groups such as a methyl group, an ethyl group, a n-propyl group, an isopropyl group, a n-butyl group, and a tert-butyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxy groups such as a methoxy group, an ethoxy group, and a propoxy group; aryloxy groups such as a phenoxy group; halogen atoms such as fluorine, chlorine, bromine, and iodine; and cyano groups.

In the formula [1], the rings $B_1$ and $B_2$ are aromatic hydrocarbon rings having 6 to 18 carbon atoms and each have two or more electron withdrawing groups. Non-limiting examples of the rings $B_1$ and $B_2$ include a benzene ring, a naphthalene ring, a phenanthrene ring, a fluorene ring, a fluoranthene ring, a pyrene ring, an anthracene ring, and a triphenylene ring. Among them, the rings $B_1$ and $B_2$ may be a benzene ring or a naphthalene ring having a low molecular weight from the viewpoint of sublimability. The rings $B_1$ and $B_2$ may have the same structure.

The rings $B_1$ and $B_2$ may have a substituent other than the electron withdrawing groups. Examples of the substituent other than the electron withdrawing groups that may be included in the rings $B_1$ and $B_2$ include a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, and a silyl group. Specific examples of the substituent are the same as those that have been described as the substituent which is optionally included in the ring A. Among them, the rings $B_1$ and $B_2$ may be a substituted or unsubstituted alkyl group.

In the formula [1], $Q_1$ and $Q_2$ respectively represent one of the electron withdrawing groups of the ring $B_1$ and one of the electron withdrawing groups of the ring $B_2$, and are respectively located at an ortho position of the ring $B_1$ and at an ortho position of the ring $B_2$ with respect to the ring A. Non-limiting examples of $Q_1$ and $Q_2$ include fluorine, a trifluoromethyl group, and a cyano group. Among them, $Q_1$ and $Q_2$ may represent a cyano group having high bond energy because of its triple bond from the viewpoint of stability of a compound, that is, durability of an element. $Q_1$ and $Q_2$ may represent the same electron withdrawing group.

Next, a method for synthesizing the organic compound according to this embodiment will be described. The organic compound according to this embodiment is synthesized through, for example, the following reaction scheme.

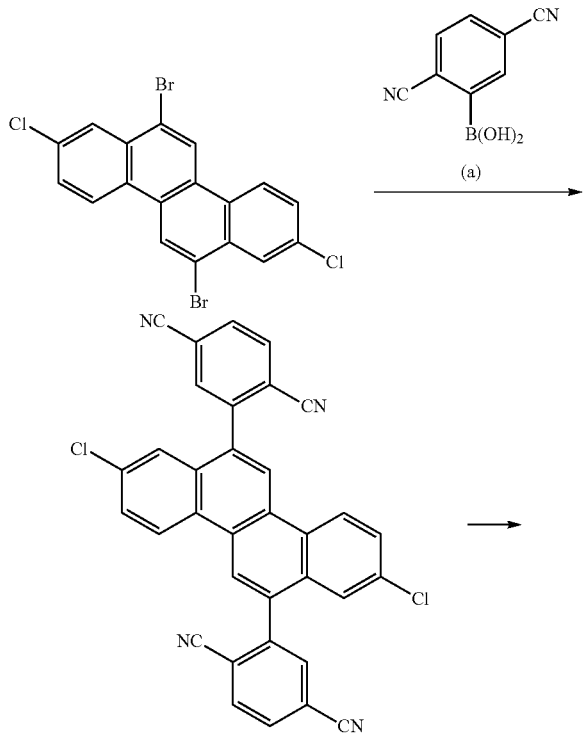

11
-continued
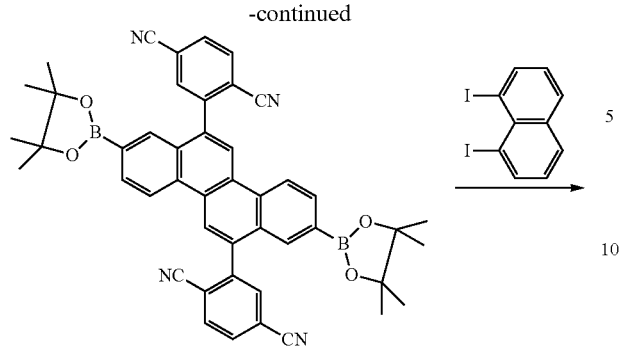
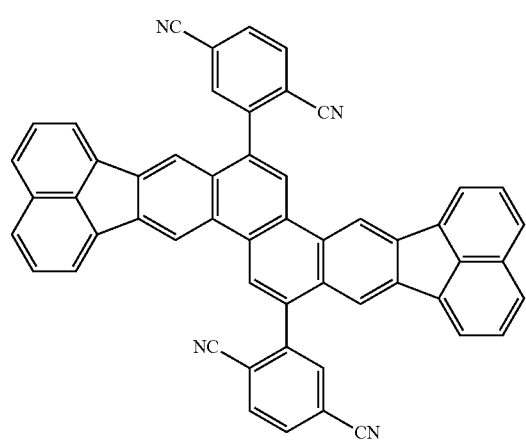
A20
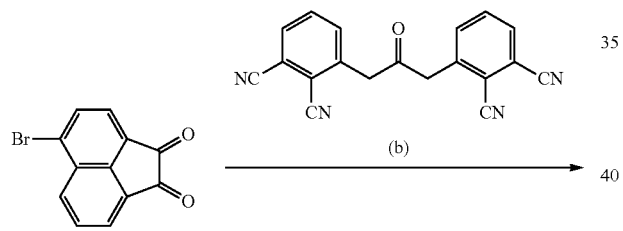
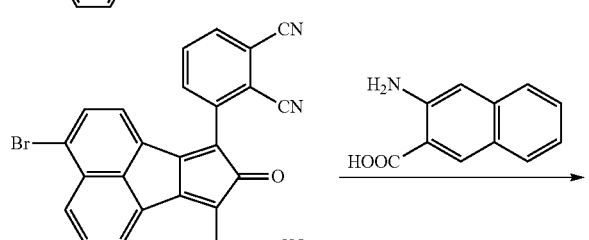
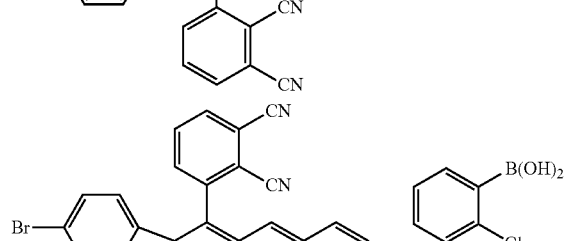
12
-continued
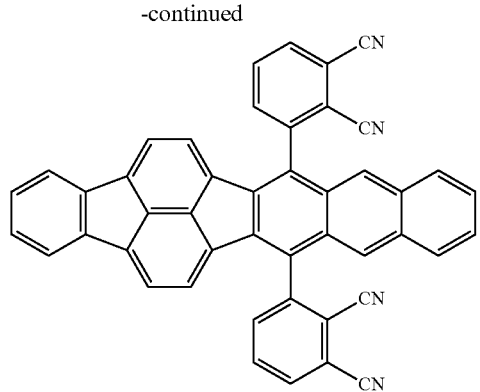
B23
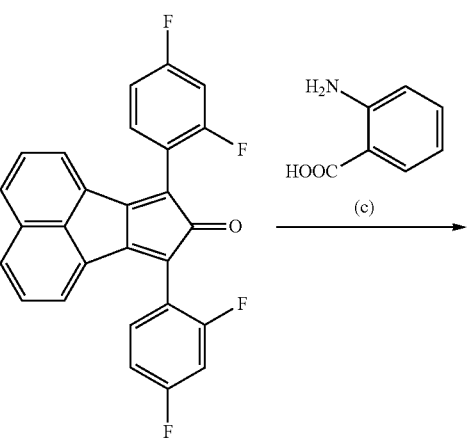
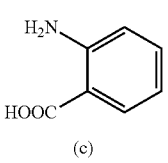
(c)
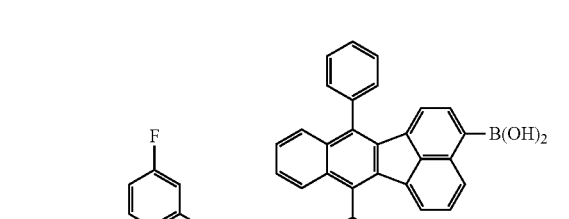
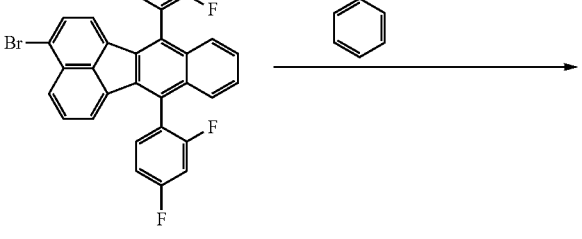
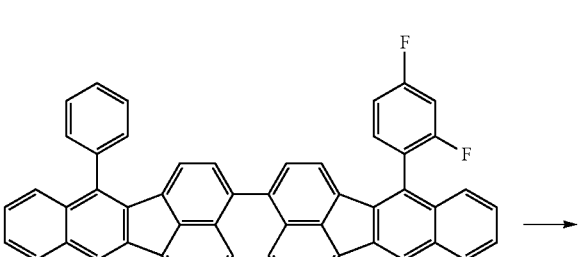

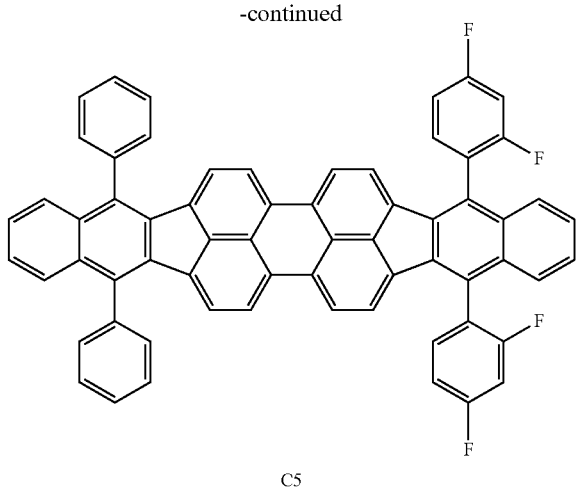

C5

Herein, the compound represented by the general formula [1] can be obtained by appropriately changing the starting materials and the compounds that are represented by (a) to (c) above and react with the starting materials. The synthesis method will be described in detail in Examples.

Since the organic compound according to this embodiment has the following features, the organic compound is a compound having a high oxidation potential, high chemical stability, and high sublimability. Furthermore, an organic light-emitting element having high durability can be provided by using the organic compound.

The term "basic skeleton" herein refers to a skeleton in which the polycyclic aromatic hydrocarbon ring including a fluoranthene skeleton and represented by the ring A is unsubstituted. Hereafter, the ring $B_1$ and the ring $B_2$ may be collectively referred to as a "ring B", and $Q_1$ and $Q_2$ may be collectively referred to as an "electron withdrawing group Q".

(1) The fluoranthene skeleton is present in the basic skeleton, the ring B has two or more electron withdrawing groups, and at least one of the electron withdrawing groups is located at an ortho position with respect to the ring A.
(2) The electron withdrawing group Q is provided so as to cover the basic skeleton.

Hereafter, these features will be described.

(1) The fluoranthene skeleton is present in the basic skeleton, the ring B has two or more electron withdrawing groups, and at least one of the electron withdrawing groups is located at an ortho position with respect to the ring A.

In the creation of the organic compound represented by the formula [1], the present inventors have focused on the basic skeleton and the substituent. In the organic compound according to this embodiment, the basic skeleton represented by the ring A is a polycyclic aromatic hydrocarbon ring having a fluoranthene skeleton, the substituents represented by the ring B have two or more electron withdrawing groups, and the substitution position of at least one of the electron withdrawing groups is an ortho position of the ring B with respect to the ring A.

The fluoranthene is an aromatic hydrocarbon having a five-membered ring. The feature of the aromatic hydrocarbon having a five-membered ring is as follows. Such an aromatic hydrocarbon has a $5\pi$ electron system. If the aromatic hydrocarbon accepts one electron (is reduced), the aromatic hydrocarbon has a $6\pi$ electron system, which causes aromatic stabilization in accordance with the Huckel's rule. Therefore, fluoranthene has better electron-accepting property and poorer electron-donating property than aromatic hydrocarbons (e.g., anthracene and pyrene) constituted by only a six-membered ring. In other words, fluoranthene does not readily donate electrons and thus has high oxidation stability. Therefore, the basic skeleton itself represented by the ring A and having a fluoranthene skeleton has high oxidation stability.

Furthermore, the substituents represented by the ring B have two or more electron withdrawing groups, at least one of which is located at an ortho position with respect to the ring A. Thus, the oxidation stability is improved.

High oxidation stability signifies that the compound itself is not easily oxidized and has high chemical stability. High chemical stability signifies that the compound itself is stable and does not readily undergo a chemical reaction. In organic light-emitting elements, carrier transport caused when an organic compound sandwiched between electrodes is repeatedly oxidized and reduced between its molecules and carrier recombination allow the organic compound to have an excited state and a ground state in a repeated manner. Consequently, the organic light-emitting elements emit light. A compound having low chemical stability is not suitable because such a compound causes a chemical reaction through an oxidation-reduction process and in an excited state, and changes into a different compound, which impairs the intrinsic element characteristics, that is, which decreases the luminance.

The oxidation stability of the organic compound according to this embodiment will be described by comparing the organic compound with comparative compounds having a structure similar to that of the organic compound according to this embodiment. Herein, the comparative compounds are comparative compounds (1) to (5) listed in Table 1. The comparative compounds (1) to (5) are compounds having a basic skeleton similar to that of the compound 1-A disclosed in Japanese Patent Laid-Open No. 11-40360.

One of the organic compounds according to this embodiment is an exemplary compound A1 listed in Table 1. The exemplary compound A1 is a compound in which, in the general formula [1], the ring A is a basic skeleton of the compound 1-A disclosed in Japanese Patent Laid-Open No. 11-40360, the rings $B_1$ and $B_2$ are benzene rings, and the electron withdrawing groups $Q_1$ and $Q_2$ are cyano groups.

Herein, the comparative compounds (1) to (5) and the exemplary compound A1 are compared with each other in terms of oxidation-reduction potential by performing cyclic voltammetry (CV) measurement. Table 1 shows the results. The CV measurement was performed using a DMF solution of 0.1 M tetrabutylammonium perchlorate (for reduction potential measurement) and a dichloromethane solution of 0.1 M tetrabutylammonium perchlorate (for oxidation potential measurement). The reference electrode was Ag/Ag$^+$, the counter electrode was Pt, and the working electrode was glassy carbon. The scanning speed of voltage was 1.0 V/s. The measurement instrument was an electrochemical analyzer 660C manufactured by ALS.

TABLE 1

| Compound | Structure | Oxidation potential (V) | Reduction potential (V) |
|---|---|---|---|
| Comparative compound (1) | 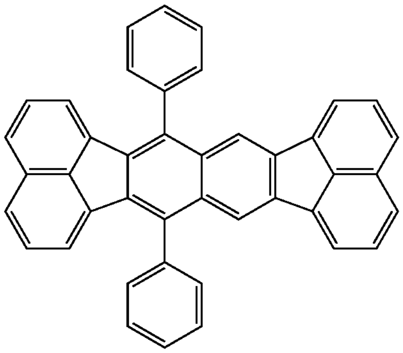 [SMILES: c1ccc(-c2c3cc4c(cc3c(-c3ccccc3)c3c5cccc6cccc(c23)c65)c2cccc3cccc4c32)cc1] | 1.03 | −2.00 |
| Comparative compound (2) | 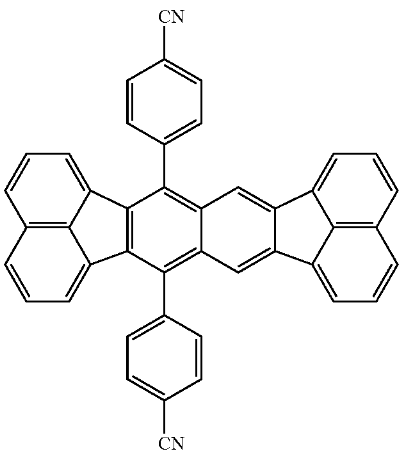 [SMILES: N#Cc1ccc(-c2c3cc4c(cc3c(-c3ccc(C#N)cc3)c3c5cccc6cccc(c23)c65)c2cccc3cccc4c32)cc1] | 1.10 | −1.94 |
| Comparative compound (3) | 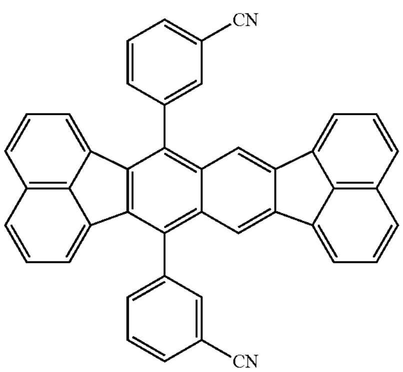 [SMILES: N#Cc1cccc(-c2c3cc4c(cc3c(-c3cccc(C#N)c3)c3c5cccc6cccc(c23)c65)c2cccc3cccc4c32)c1] | 1.11 | −1.95 |
| Comparative compound (4) | 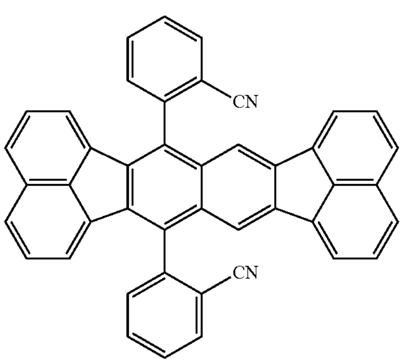 [SMILES: N#Cc1ccccc1-c1c2cc3c(cc2c(-c2ccccc2C#N)c2c4cccc5cccc(c12)c54)c1cccc2cccc3c21] | 1.15 | −1.93 |

TABLE 1-continued

| Compound | Structure | Oxidation potential (V) | Reduction potential (V) |
|---|---|---|---|
| Comparative compound (5) | 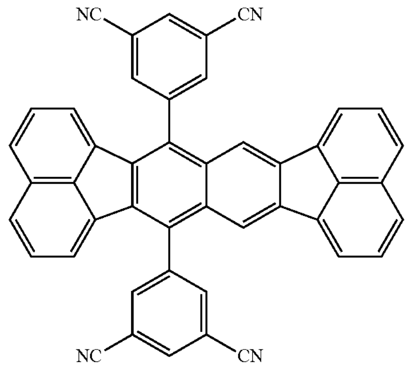 [SMILES: N#Cc1cc(C#N)cc(-c2c3cc4c(cc3c(-c3cc(C#N)cc(C#N)c3)c3c5cccc6cccc(c23)c65)c2cccc3cccc4c32)c1] | 1.19 | −1.89 |
| Exemplary compound A1 | 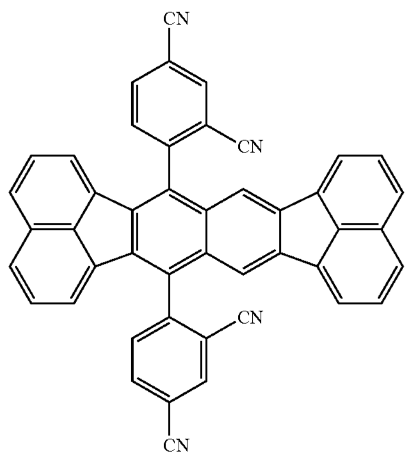 [SMILES: N#Cc1ccc(-c2c3cc4c(cc3c(-c3ccc(C#N)cc3C#N)c3c5cccc6cccc(c23)c65)c2cccc3cccc4c32)c(C#N)c1] | 1.21 | −1.87 |

Table 1 shows that the comparative compounds (1) to (5) have oxidation potentials of 1.03 V, 1.10 V, 1.11 V, 1.15 V, and 1.19 V, respectively, whereas the exemplary compound A1 according to this embodiment has a high oxidation potential of 1.21 V. In other words, the exemplary compound A1 is a compound that is not easily oxidized.

This has been considered as follows. The comparison between the comparative compounds (2) to (4) shows that the oxidation potential of the comparative compound (4) having a cyano group located at an ortho position is a highest potential of 1.15 V. This shows that when electron withdrawing groups are introduced, the substitution position that increases the oxidation potential and provides the highest contribution to the oxidation stability is an ortho position. This is probably because the highest occupied molecular orbital (HOMO) is present in the basic skeleton represented by the ring A and the substitution position having the shortest distance between the ring A and the electron withdrawing group via the ring B is an ortho position, which maximizes the electron withdrawing effect, that is, the contribution to an increase in oxidation potential. Furthermore, the organic compound according to this embodiment further has one or more electron withdrawing groups at a position other than the ortho position, and thus has a high oxidation potential and is stable as a compound. Therefore, the organic light-emitting element including this compound has high stability and high durability.

(2) The electron withdrawing group Q is provided so as to cover the basic skeleton.

In general, since polycyclic aromatic hydrocarbons have high molecular planarity, the degree of molecular packing increases. The molecular packing unfavorably increases the crystallinity, which deteriorates sublimability and causes concentration quenching. In other words, a decrease in the degree of molecular packing can improve the sublimability and can suppress the concentration quenching. The improvement in sublimability can increase the purity of a material through sublimation purification and enables the production of an organic light-emitting element by vapor deposition. This can decrease the amount of impurities contained in the organic light-emitting element. Thus, a decrease in light emission efficiency due to impurities and a decrease in driving durability can be suppressed. The reduction in concentration quenching is suitable from the viewpoint of improving the light emission efficiency of the organic light-emitting element.

Accordingly, the present inventors have focused on the molecular structure of the substituent. By introducing a substituent that covers a conjugate plane at the center of the basic skeleton, the degree of molecular packing can be decreased. In the organic compound according to this embodiment, the arrangement of the molecular packing is believed to be facilitated through overlapping of π conjugate planes of the basic skeleton represented by the ring A. Accordingly, the present inventors have attempted to introduce a substituent that covers the π conjugate plane.

Specifically, it has been attempted that the π conjugate plane of the basic skeleton is covered by introducing a cyano group to an ortho position of a benzene ring serving as a substituent as in the exemplary compound A17 listed in FIG. 1, thereby decreasing the degree of molecular packing. The exemplary compound A17 is a compound in which, in the general formula [1], the ring A is FF5, the rings $B_1$ and $B_2$ are benzene rings, and the electron withdrawing groups $Q_1$ and $Q_2$ are cyano groups. The comparative compound (6) is a compound different from the exemplary compound A17 in terms of the substitution position of the electron withdrawing group of the ring B.

The effect of the substituent represented by the ring B will be described by comparing the comparative compound (6) and the exemplary compound A17. The comparative compound (6) and the exemplary compound A17 have the same molecular weight, but the exemplary compound A17 has a larger difference between decomposition temperature and sublimation temperature than the comparative compound (6). As the difference between decomposition temperature and sublimation temperature increases, the temperature margin in sublimation purification increases, which achieves excellent sublimability.

This is probably because the angle (dihedral angle) between the basic skeleton and the ring B is 56 in the comparative compound (6) whereas the angle is as large as 70° in the exemplary compound A17, which suppresses the overlapping of the π conjugate planes of the basic skeleton.

This is also probably because the cyano group physically suppresses the overlapping of the π conjugate planes of the basic skeleton, and increases the negative charge by a nitrogen atom having high electronegativity and thus exerts a repulsive force between cyano groups, which inhibits the overlapping of the π conjugate planes.

That is, when the organic compound has an electron withdrawing group at an ortho position of the ring B, the degree of molecular packing can be decreased, which provides a compound which has high sublimability and whose concentration quenching can be suppressed. Therefore, the organic light-emitting element including this compound has high driving durability and exhibits high-efficiency light-emitting properties.

The sublimation temperature is a temperature at which the organic compound is gradually heated at a degree of vacuum of $1\times10^{-1}$ Pa in an atmosphere of Ar flow, the sublimation purification is initiated, and the sublimation rate reaches a sufficient sublimation rate. The decomposition temperature is a temperature at which the weight loss determined by TG/DTA measurement reaches 5%.

Accordingly, when the organic compound according to this embodiment satisfies the conditions (1) and (2), the organic compound is a compound having high oxidation stability and high sublimability.

Furthermore, when the organic compound satisfies the following condition (3), the organic compound is suitable as a compound used for organic light-emitting elements. This is because when the condition (3) is satisfied, the effect of decreasing the degree of molecular packing is further improved.

(3) The ring B bonds to the ring A at a position at which the dihedral angle between the fluoranthene skeleton and the ring B is large.

The organic compound according to this embodiment has high planarity of the basic skeleton represented by the ring A. If the organic compound is unsubstituted, the degree of molecular packing increases. The organic compound according to this embodiment may have a substituent at the ring A.

The substituent is selected from the group consisting of a phenyl group, a naphthyl group, a phenanthryl group. The phenyl group is more suitable. Herein, the substitution position that can effectively decrease the degree of molecular packing will be described.

The degree of molecular packing, that is, the π-π interaction between molecules increases as the π plane is expanded. To decrease the π-π interaction, the present inventors have focused on the dihedral angle between the ring A serving as a basic skeleton and the ring B serving as a substituent. Herein, the dihedral angle between the basic skeleton and the substituent was estimated by the molecular orbital calculations using fluoranthene, which is the minimum unit of the ring A serving as a basic skeleton, and benzene, which is the minimum unit of the ring B serving as a substituent.

The density functional theory (DFT), which has been widely used today, was used as a calculation technique of the molecular orbital calculations. The functional was B3LYP and the basis function was 6-31G*. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford CT, 2010.), which has been widely used today.

TABLE 2

| Name | Structure | Dihedral angle (°) | S1 (nm) |
|---|---|---|---|
| 8-phenylfluoranthene | 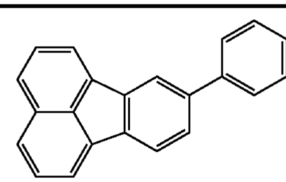 | 38.2 | 384 |
| 7-phenylfluoranthene | 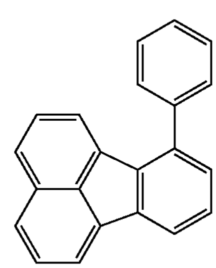 [SMILES: c1ccc(-c2cccc3c2-c2cccc4cccc-3c24)cc1] | 59.2 | 365 |

TABLE 2-continued

| Name | Structure | Dihedral angle (°) | S1 (nm) |
|---|---|---|---|
| 1-phenylfluoranthene | 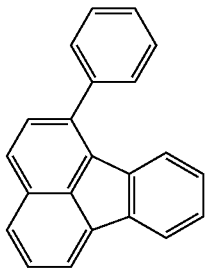 [SMILES: c1ccc(-c2ccc3cccc4c3c2-c2ccccc2-4)cc1] | 55.5 | 373 |
| 2-phenylfluoranthene | 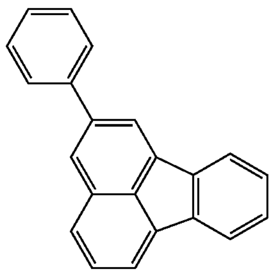 [SMILES: c1ccc(-c2cc3c4c(cccc4c2)-c2ccccc2-3)cc1] | 38.1 | 380 |
| 3-phenylfluoranthene | 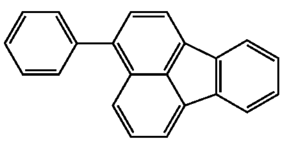 [SMILES: c1ccc(-c2ccc3c4c(cccc24)-c2ccccc2-3)cc1] | 49.5 | 376 |

Table 2 shows that 7-phenylfluoranthene has the largest dihedral angle and the shortest wavelength. Since the dihedral angle is maximum, the π-π interaction between basic skeletons (fluoranthene) can be suppressed by the substituent (benzene). It is also found that since S1 is the smallest, the π plane is not expanded. Accordingly, 7-phenylfluoranthene can most effectively decrease the degree of molecular packing.

Therefore, the ring A has a fluoranthene skeleton represented by general formula [2] below or a benzo(k)fluoranthene skeleton represented by general formula [3] below, and the rings $B_1$ and $B_2$ may bond to the ring A at any one of positions * in the general formula [2] or [3] below.

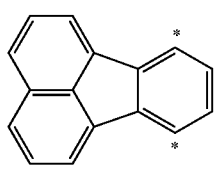

[2]

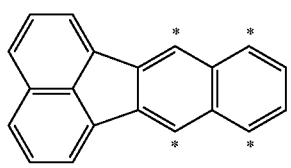

[3]

When the basic skeleton of the ring A having a fluoranthene skeleton is described using general formula [4] or [5] below, the better substitution position of the ring B for decreasing the degree of molecular packing is any one of positions * in the general formula [4] or [5].

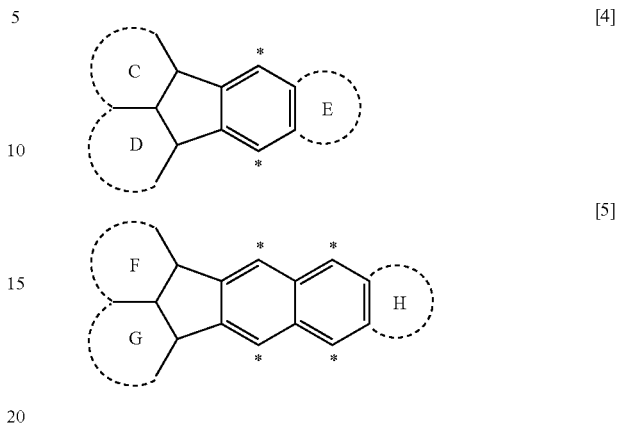

[4]

[5]

In the formula [4], the ring C to the ring E each represent an aromatic hydrocarbon ring, and ring C and the ring D may bond to each other to form a ring. In the formula [5], the ring F to the ring H each represent an aromatic hydrocarbon ring, and the ring F and the ring G may bond to each other to form a ring.

When the organic compound further satisfies the following condition (4), the organic compound may be used as a blue light-emitting material in particular. This is because when the condition (4) is satisfied, the emission wavelength is short and deep blue on the chromaticity coordinates can be reproduced.

(4) The ring A is a polycyclic aromatic hydrocarbon ring that has a fluoranthene skeleton and has 16 to 40 carbon atoms.

The organic compound according to this embodiment has an electron withdrawing group at an ortho position of the ring B and thus has a feature of high oxidation potential. Therefore, the band gap of the compound itself is larger than that of compounds having no electron withdrawing group. This signifies that the emission wavelength shifts to shorter wavelengths. With this feature, compounds suitable for emission wavelength regions required for the materials, such as blue, green, yellow, and red emission wavelength regions, can be obtained by adjusting the emission wavelength. In particular, in the blue region, deeper blue can be reproduced on the chromaticity coordinates of blue when the emission wavelength is shorter. Therefore, the feature of the organic compound according to this embodiment can be more suitably used.

In this embodiment, since the light-emitting properties (emission wavelength region) themselves are roughly dependent on the degree of π conjugation of the ring A, the degree of π conjugation is suitably small to some extent to obtain an emission wavelength in the blue region. Specifically, the ring A is a polycyclic aromatic hydrocarbon ring having 16 to 40 carbon atoms. Non-limiting examples of the polycyclic aromatic hydrocarbon having a fluoranthene skeleton and having 16 to 40 carbon atoms include FF1 to FF16 described above.

Herein, the comparative compounds (7) and (8) and the exemplary compound A23 are compared with each other in terms of emission wavelength. Table 3 shows the results. The emission wavelength was measured by photoluminescence measurement of a diluted toluene solution at an excitation wavelength of 350 nm at room temperature using an F-4500 manufactured by Hitachi, Ltd.

TABLE 3

| Compound | Structure | Emission wavelength (nm) |
|---|---|---|
| Comparative compound (7) | 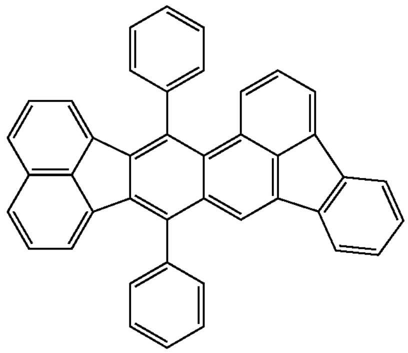 [SMILES: c1ccc(-c2c3cc4c5ccccc5c5cccc(c3c(-c3ccccc3)c3c6cccc7cccc(c23)c76)c54)cc1] | 440 |
| Exemplary compound A23 | 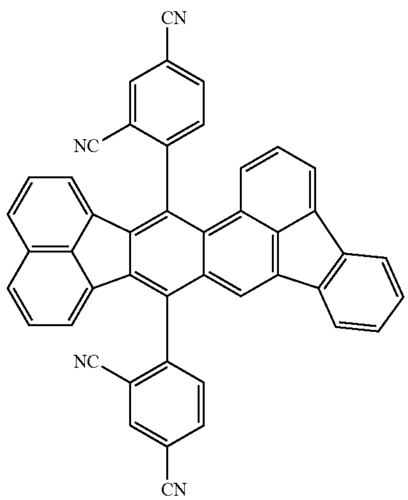 [SMILES: N#Cc1ccc(-c2c3cc4c5ccccc5c5cccc(c3c(-c3ccc(C#N)cc3C#N)c3c6cccc7cccc(c23)c76)c54)c(C#N)c1] | 437 |
| Comparative compound (8) | 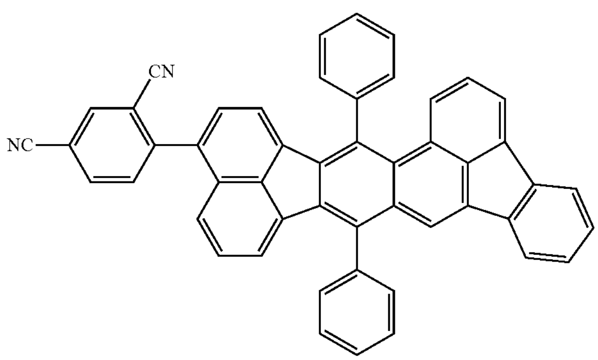 [SMILES: N#Cc1ccc(-c2ccc3c4c(-c5ccccc5)c5c(cc6c7ccccc7c7cccc5c76)c(-c5ccccc5)c4c4cccc2c43)c(C#N)c1] | 473 |

Table 3 shows that the emission wavelength of the exemplary compound A23 is shifted to shorter wavelengths by the electron withdrawing group. Therefore, when the organic compound according to this embodiment satisfies the condition (4), the organic compound is capable of emitting blue light with a high color purity that can reproduce deep blue. The chromaticity coordinates of blue will be described in detail in Examples. On the other hand, the emission wavelength of the comparative compound (8) is considerably shifted to longer wavelengths by introducing the electron withdrawing group. This shows that the emission wavelength can be adjusted by selecting the number and substitution position of electron withdrawing groups. The number and substitution position of electron withdrawing groups in the comparative compound (8) are particularly useful when the emission wavelength of a green or red light-emitting material is shifted to longer wavelengths for adjustment.

Since the organic compound according to this embodiment is a compound that has the above properties (1) and (2) and further has the property (3), the organic compound has high oxidation stability and high sublimability. Furthermore, when the organic compound has the property (4), the organic compound emits blue light having a short wavelength. By using this organic compound, a high-efficiency organic light-emitting element having high durability can be provided.

The organic compound according to an embodiment of the present disclosure will be specifically described below. However, the present invention is not limited thereto.
A1
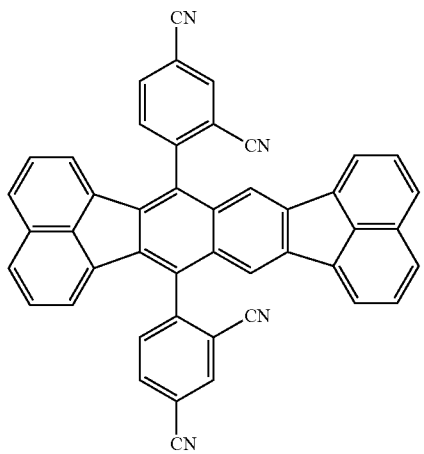
A2
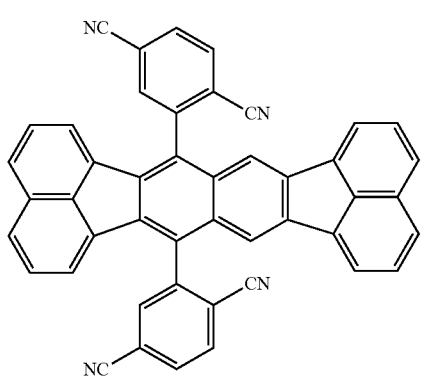
A3
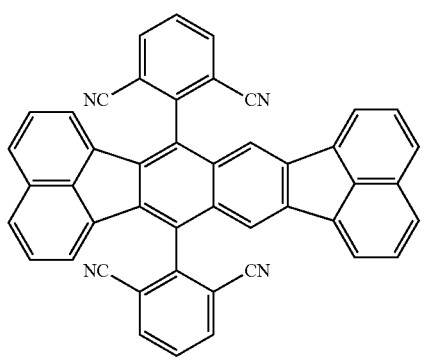
A4
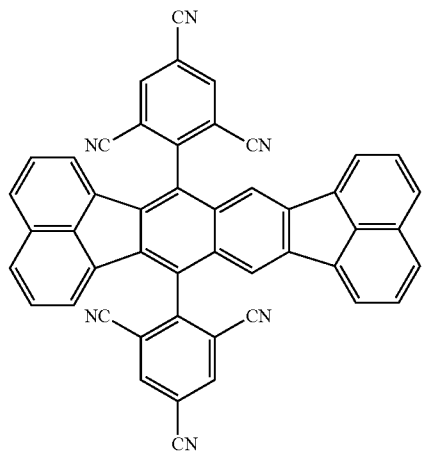
A5
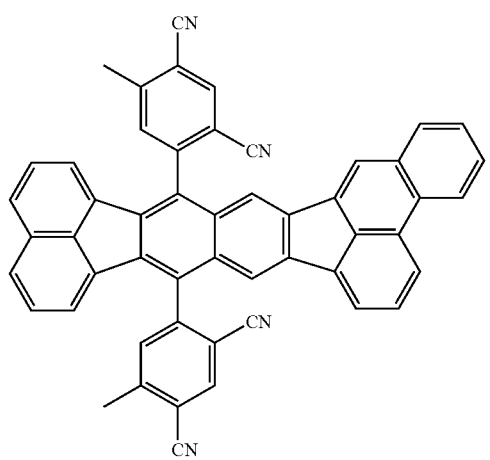
A6
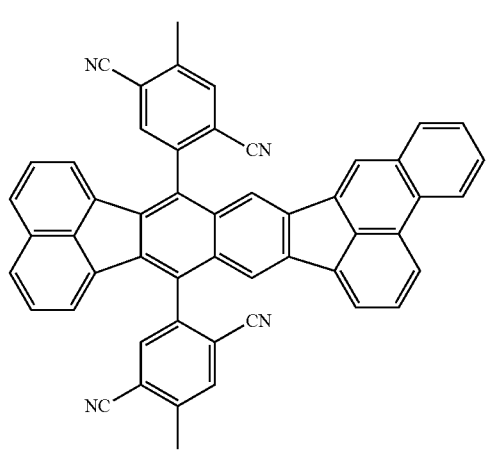

A7
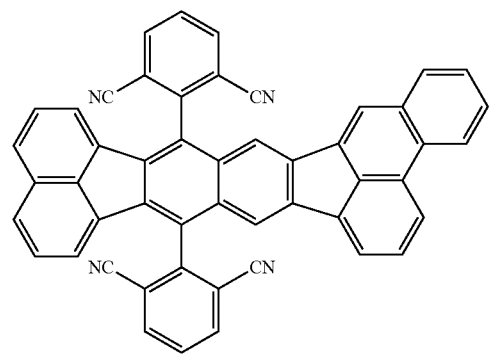
A8
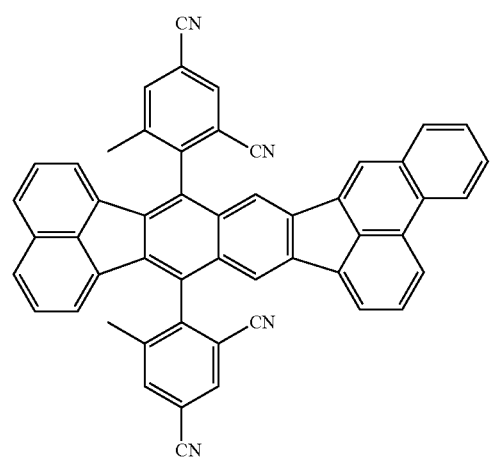
A9
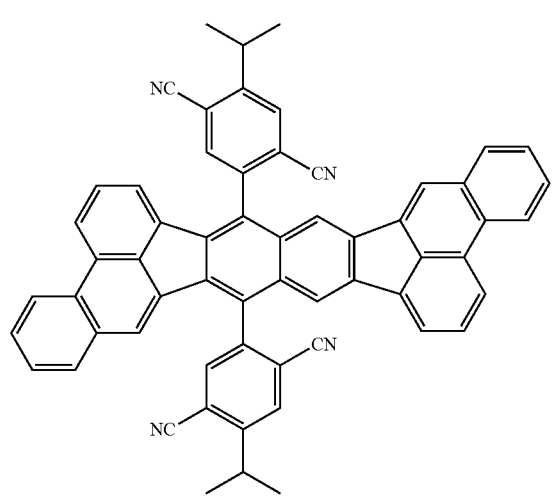
A10
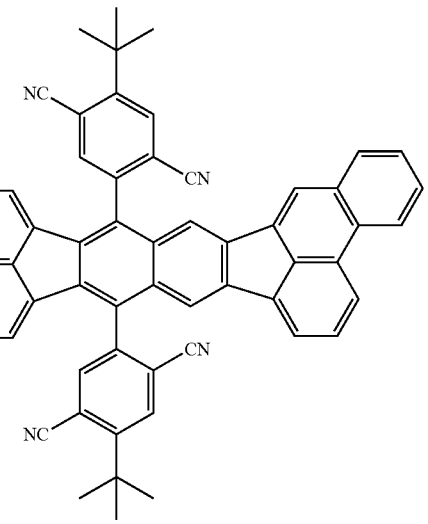
A11
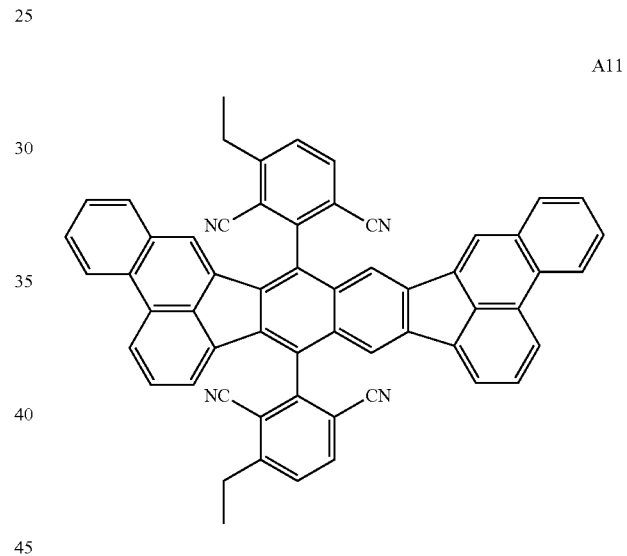
A12
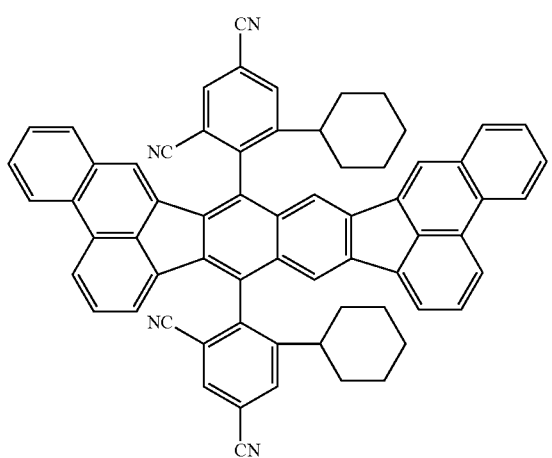

A13
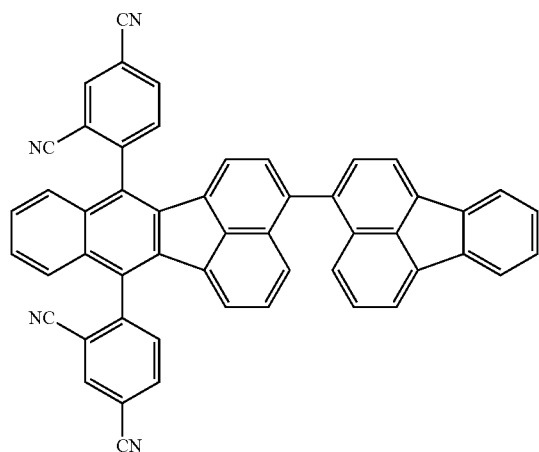
A14
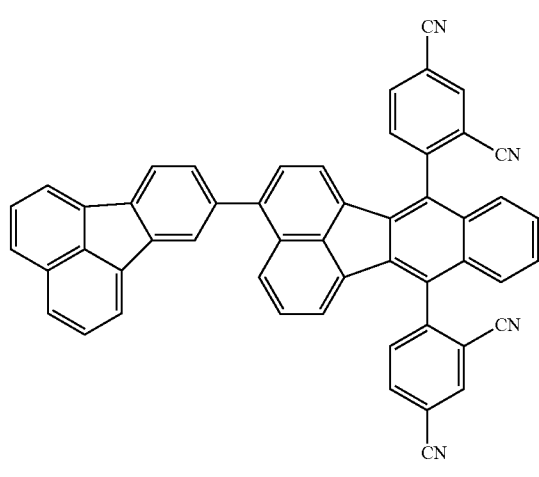
A15
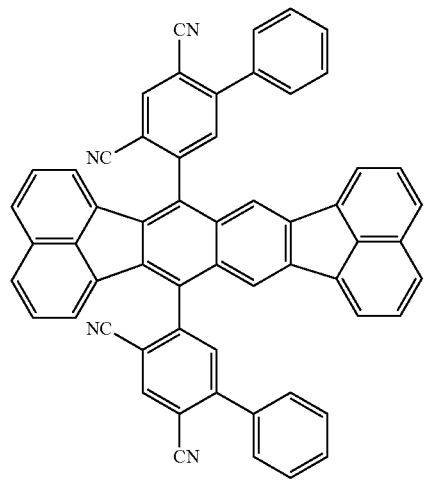
A16
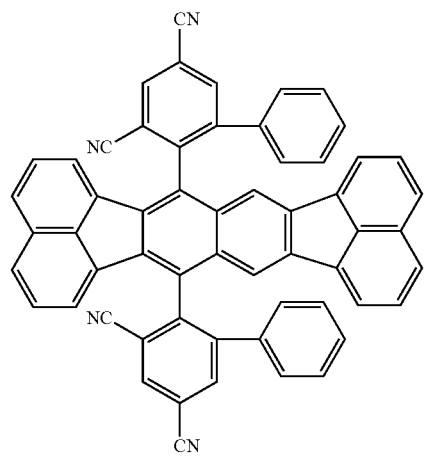
A17
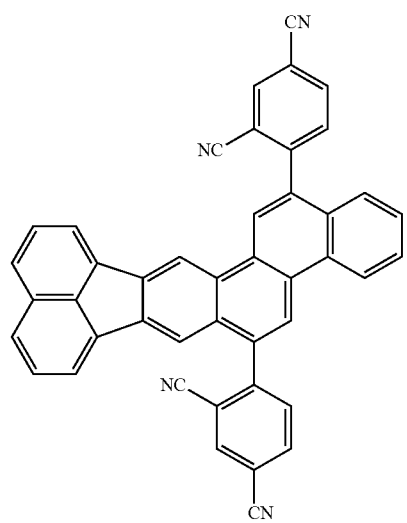
A18
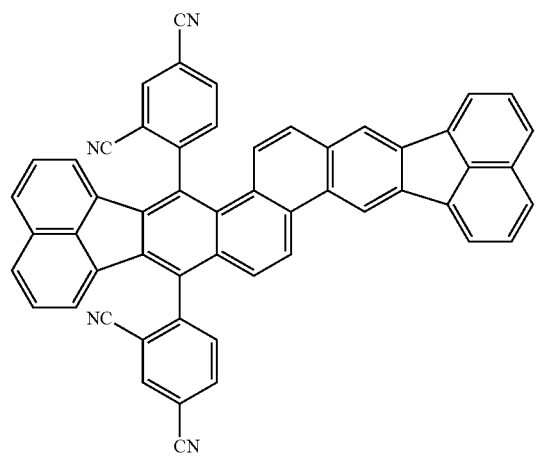

-continued
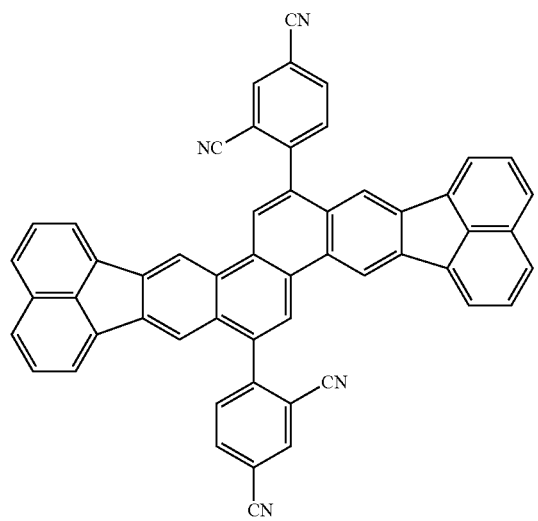
A19
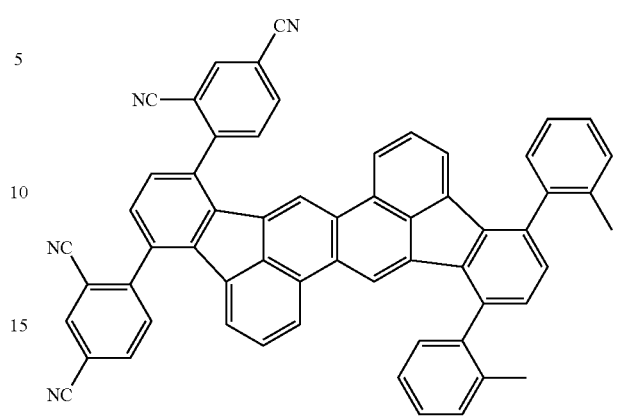
A22
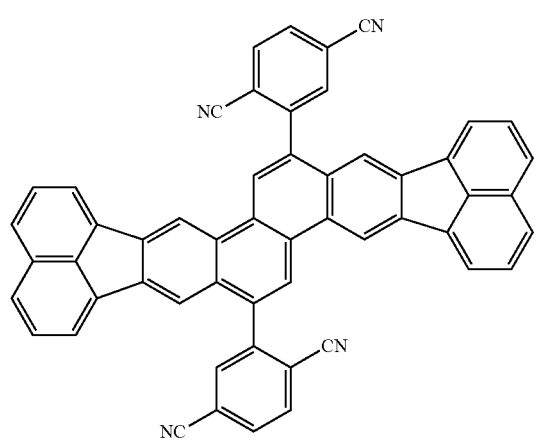
A20
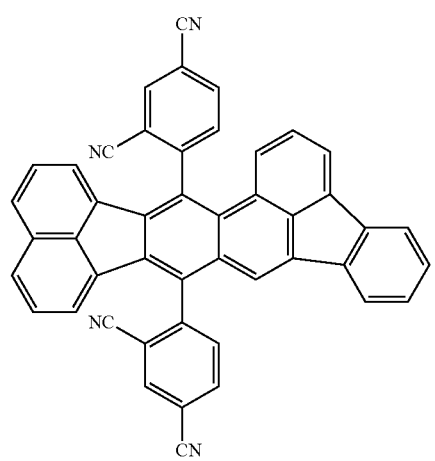
A23
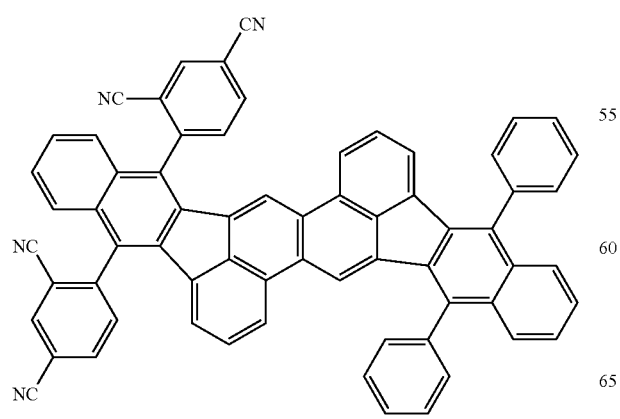
A21
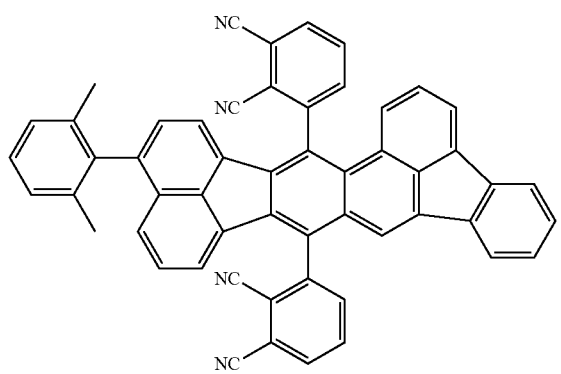
A24

A25
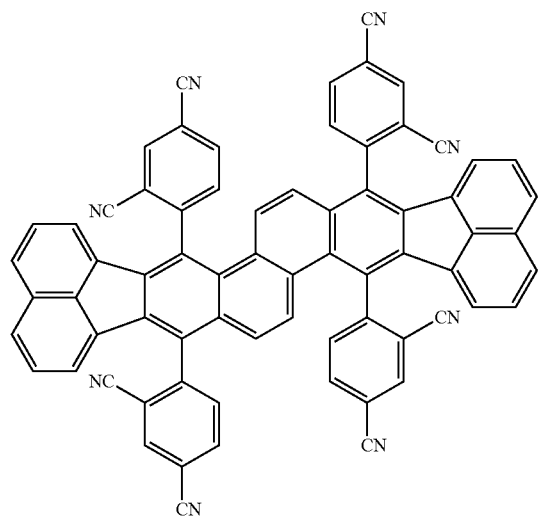
A26
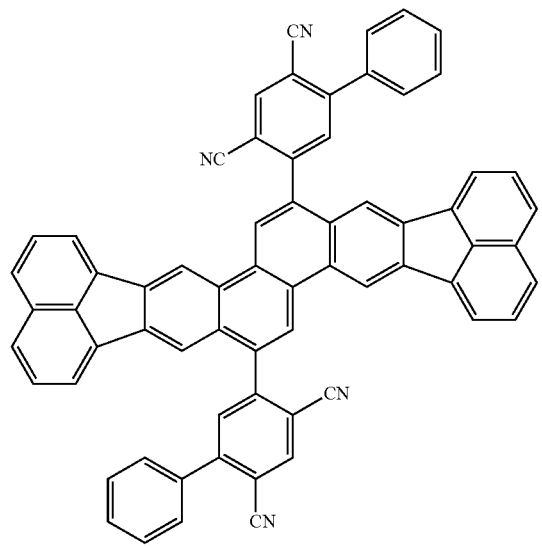
A27
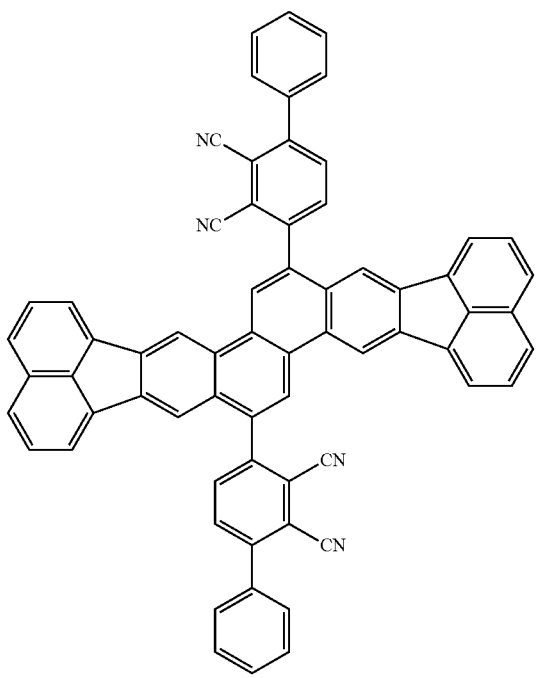
A28
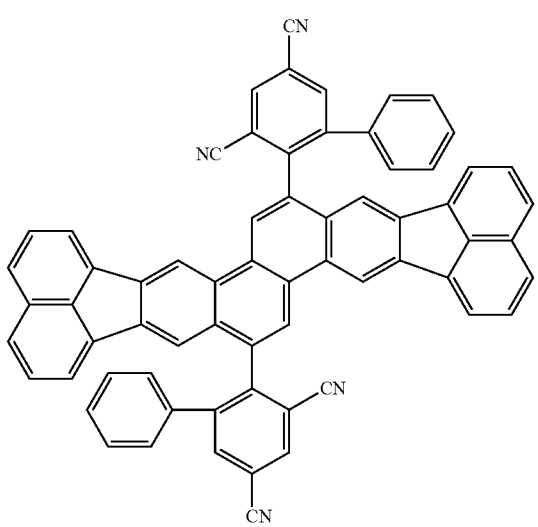

A29
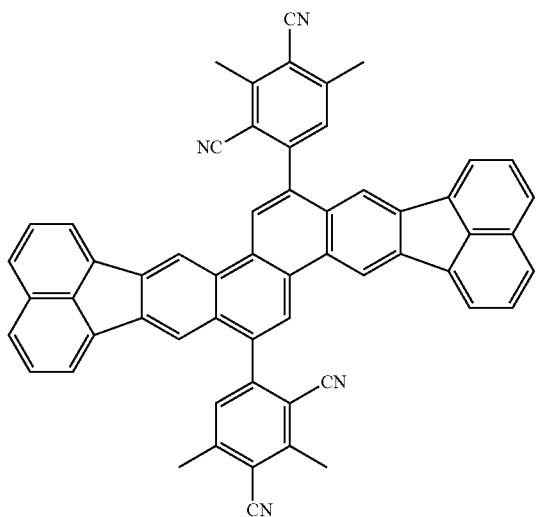
A30
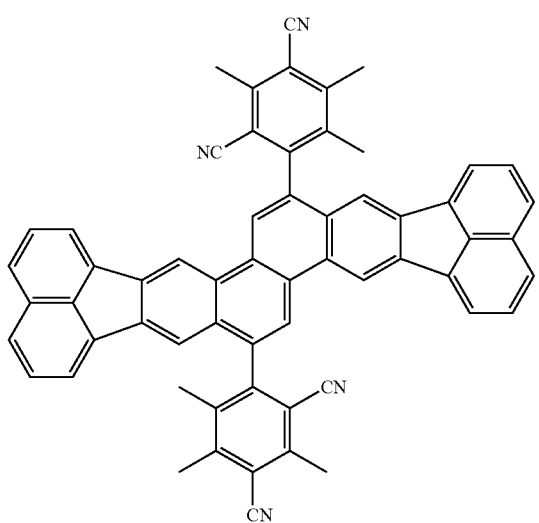
A31
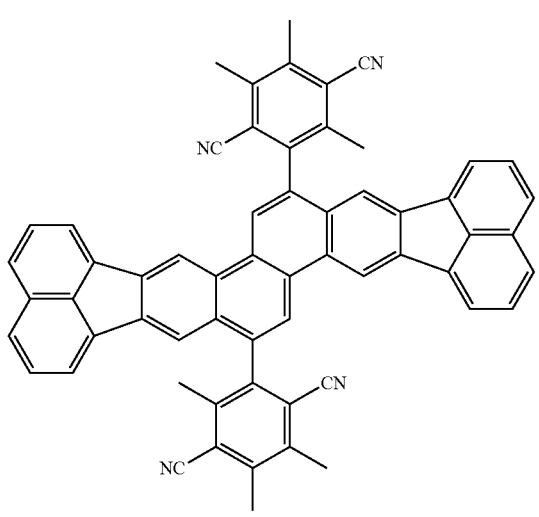
A32
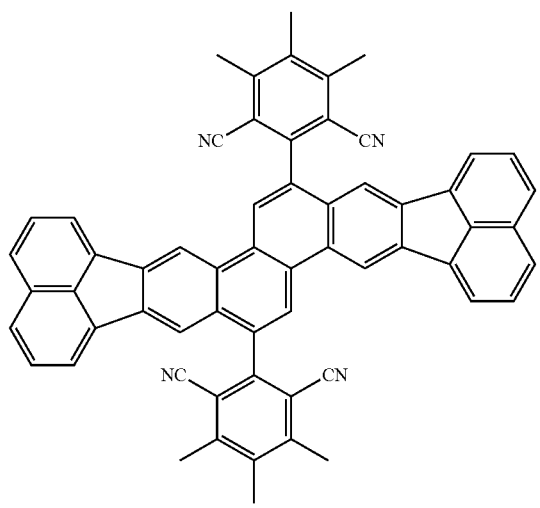
A33
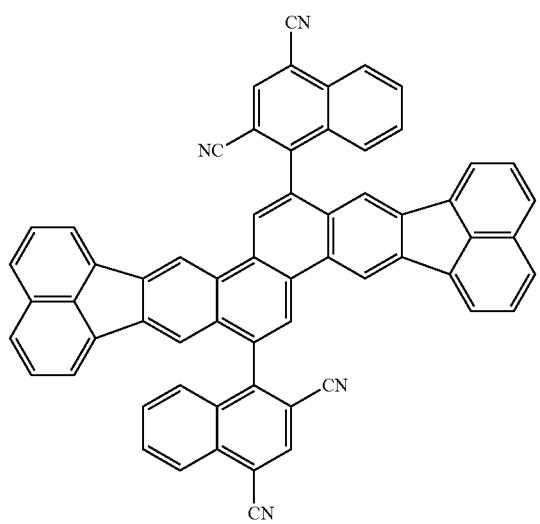
A34
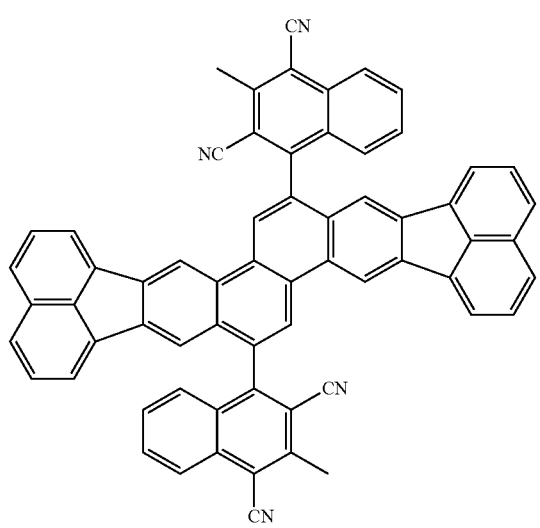

A35
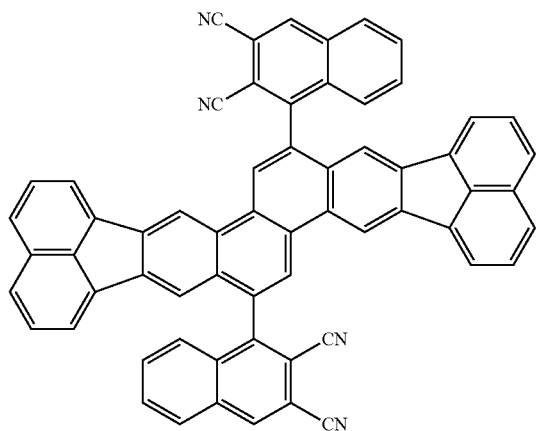
A36
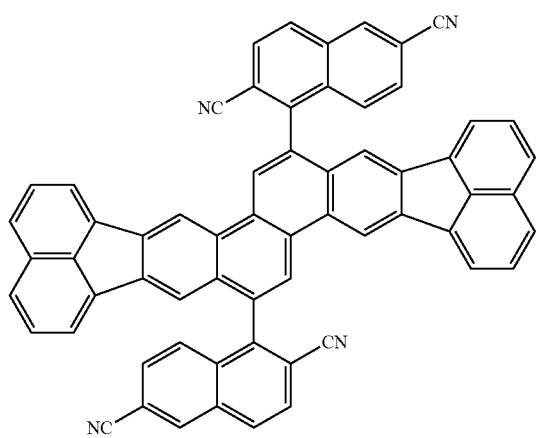
A37
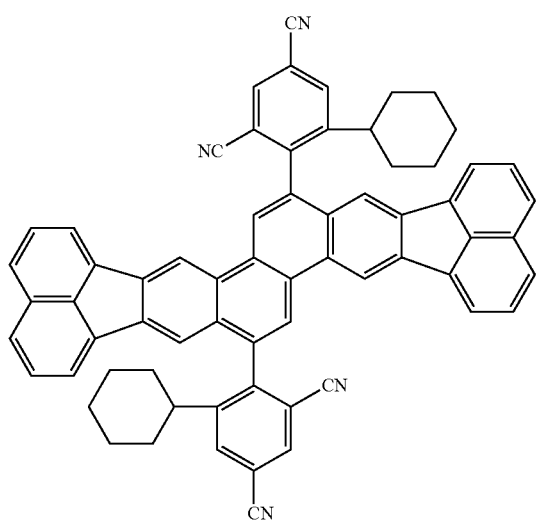
A38
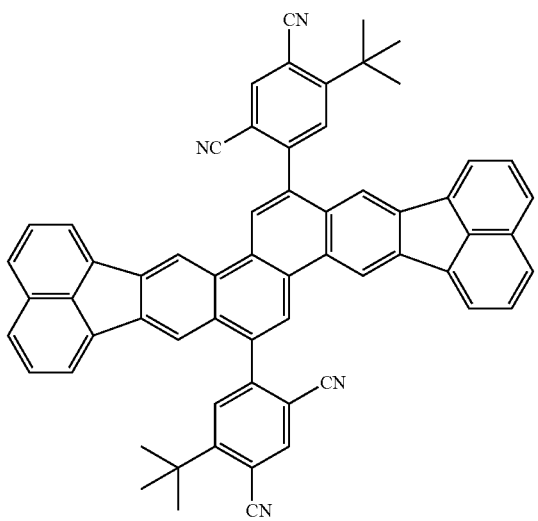
A39
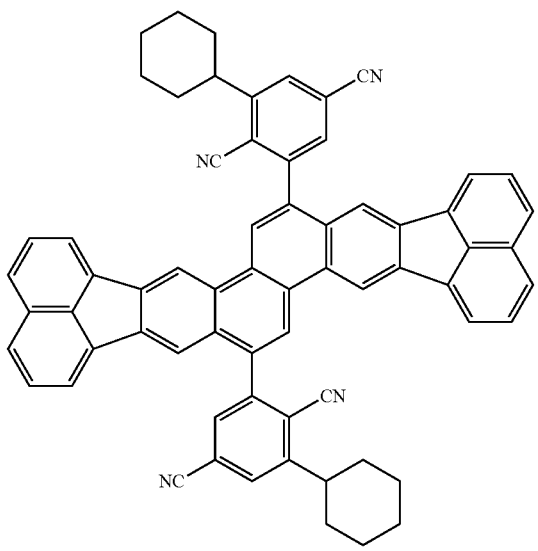

A40
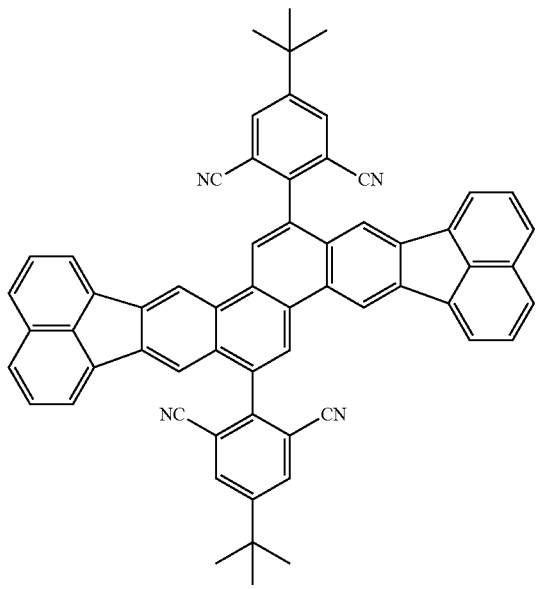
A42
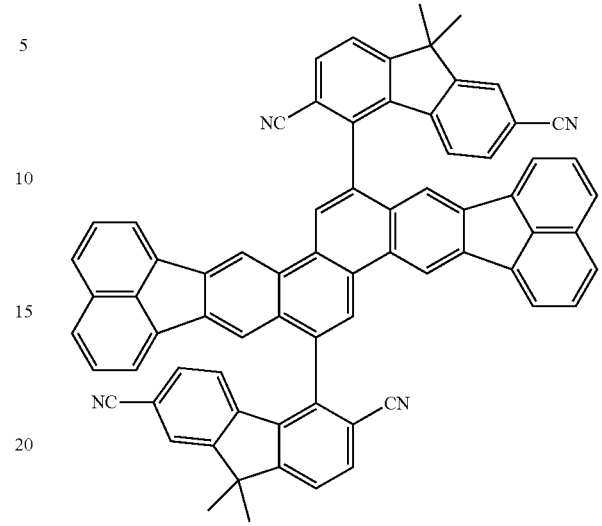
A41
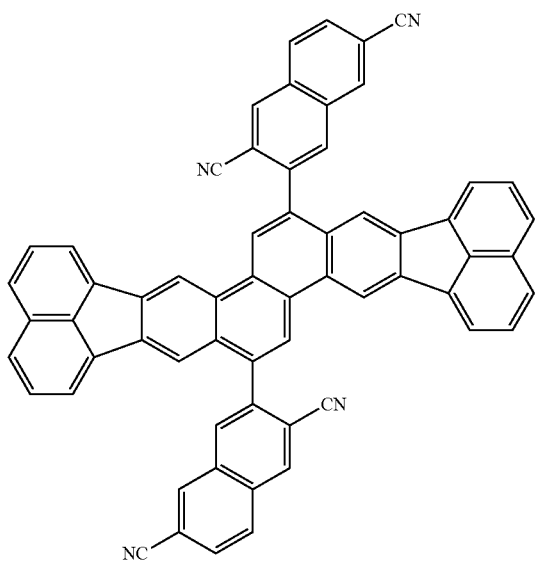
A43
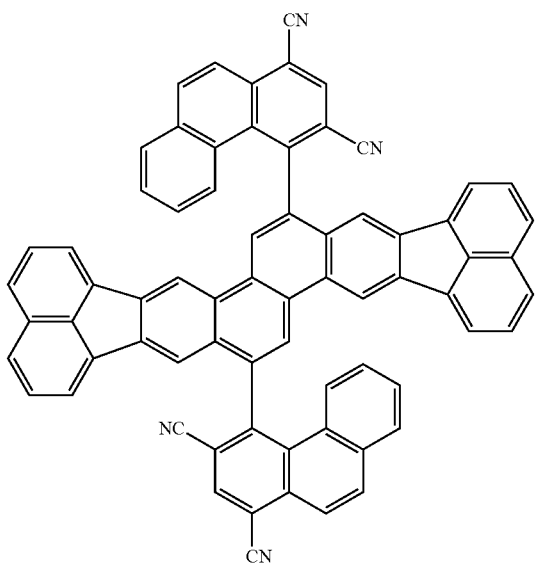

A44
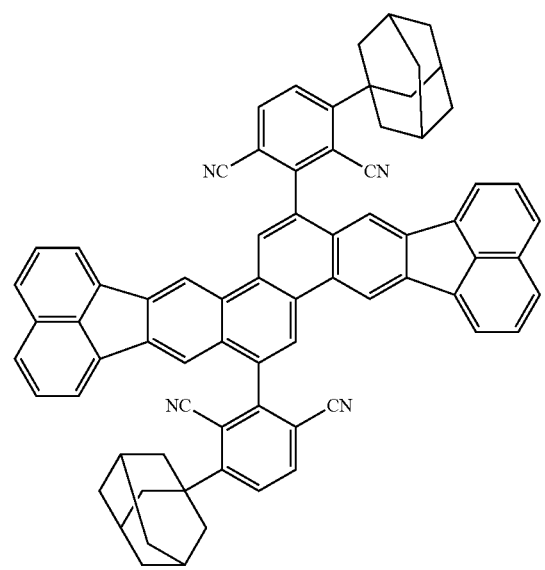
A45
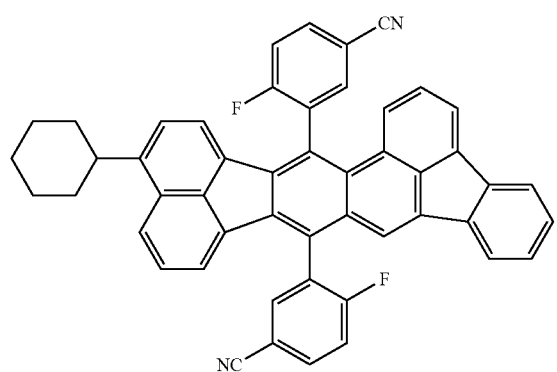
A46
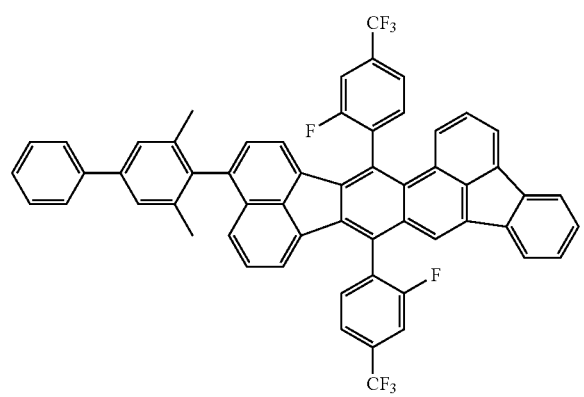
B1
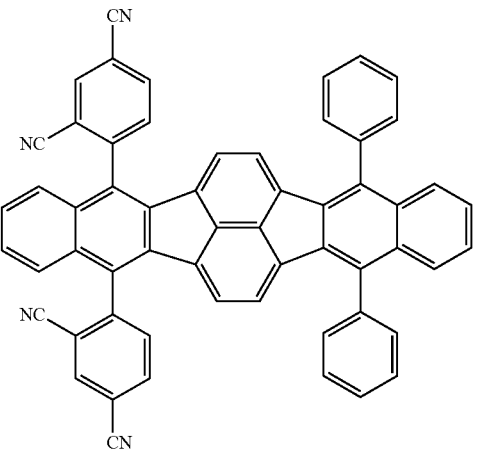
B2
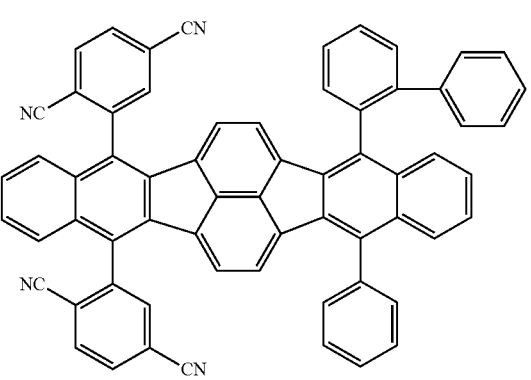
B3
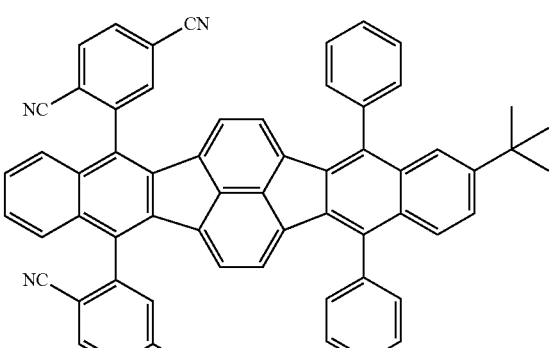
B4
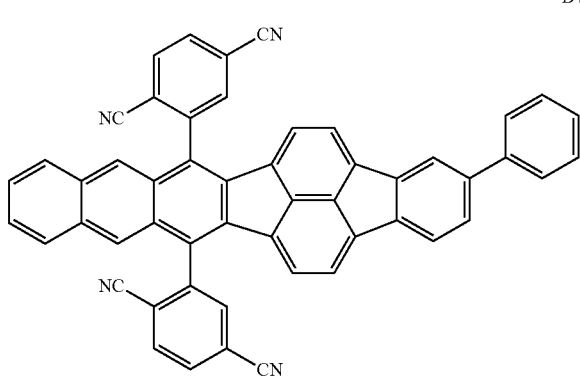

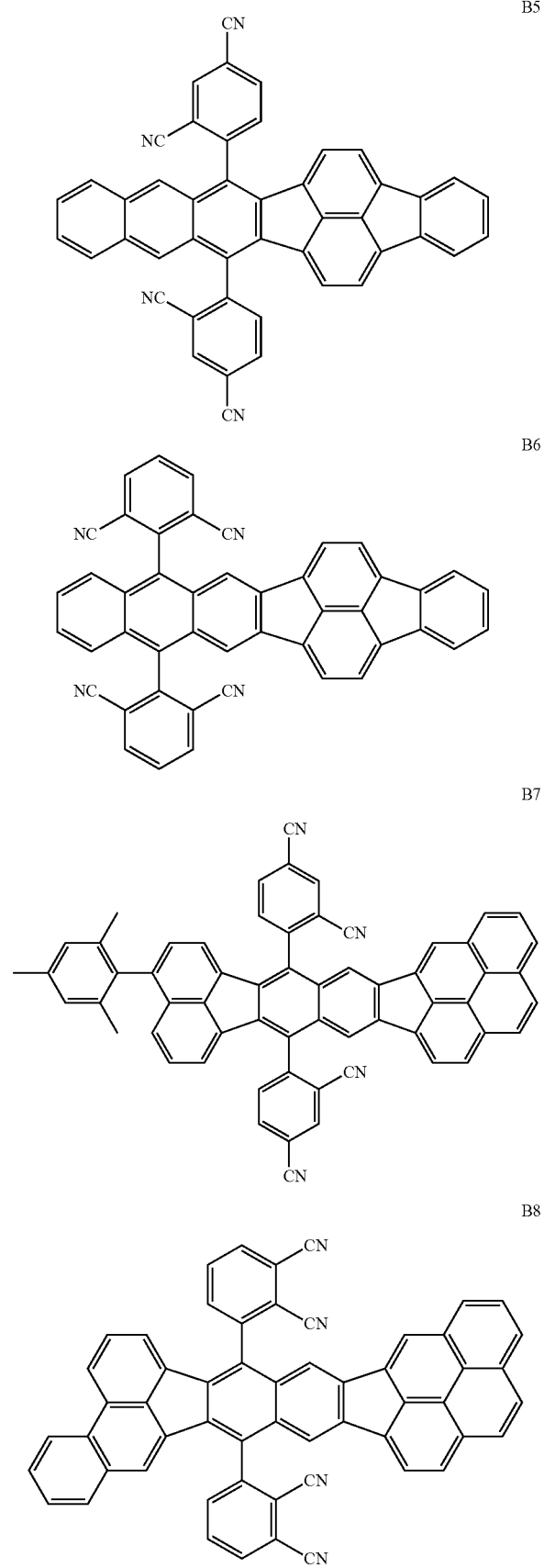

B12
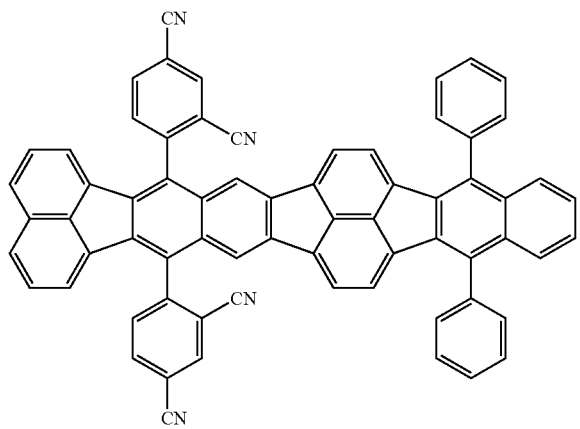
B15
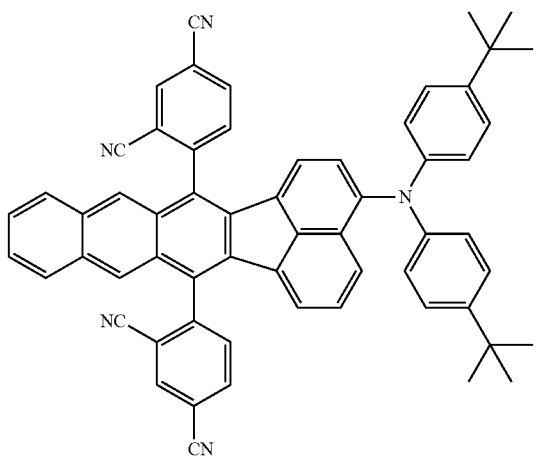
B13
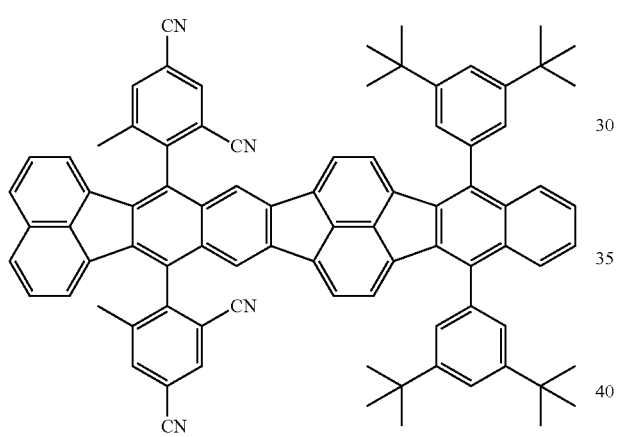
B16
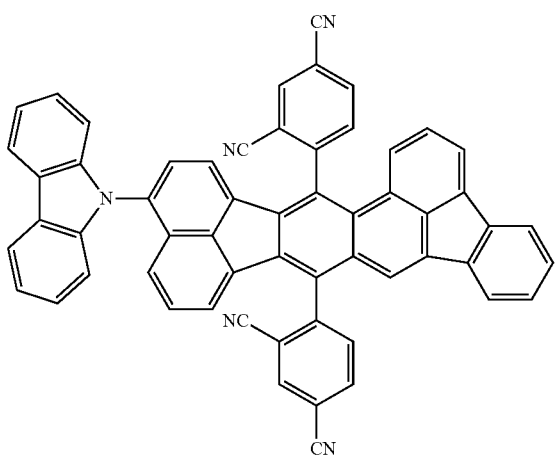
B14
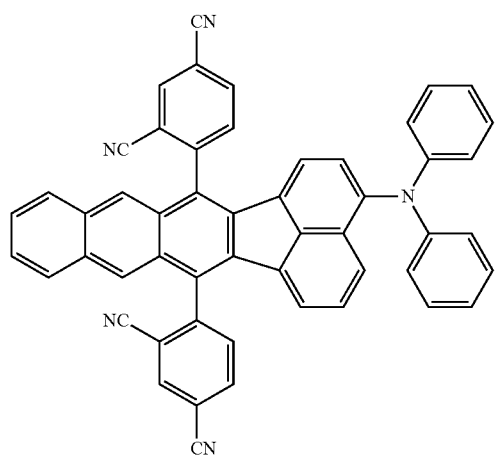
B17
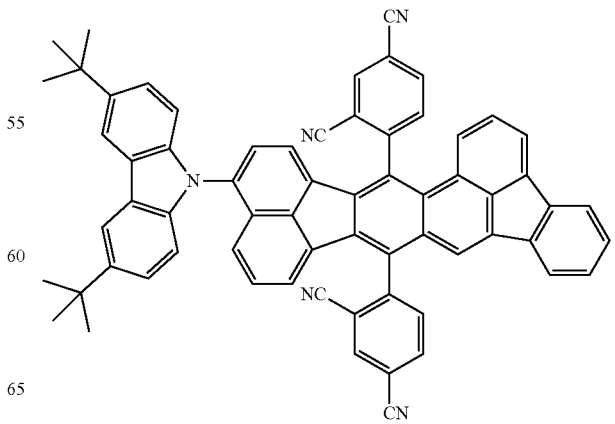

B18
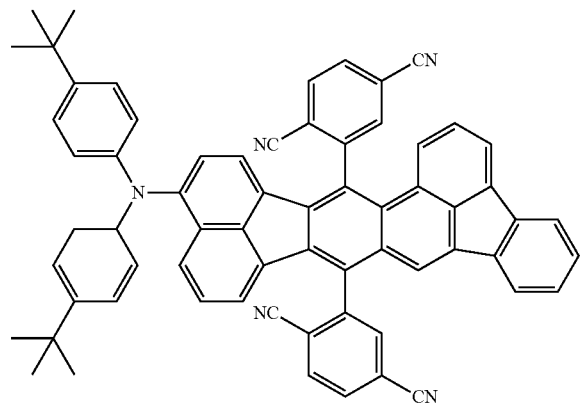
B19
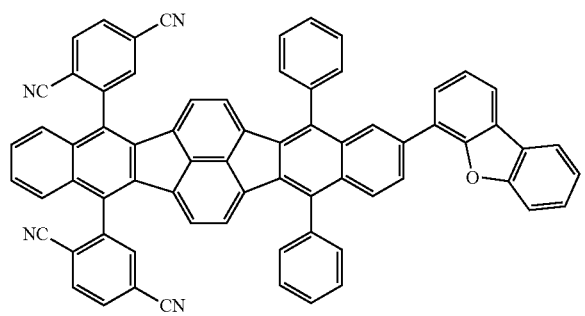
B20
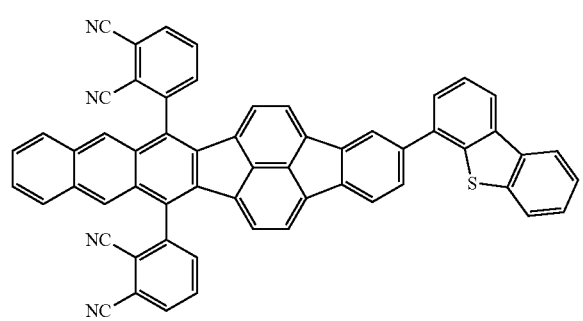
B21
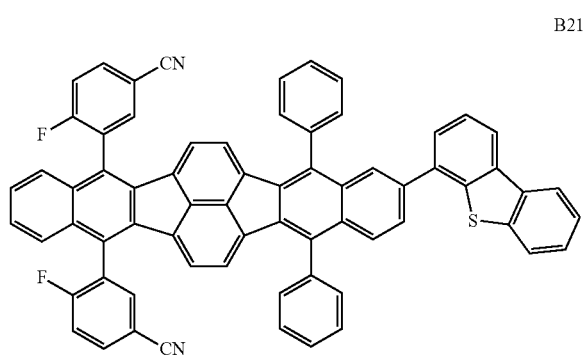
B22
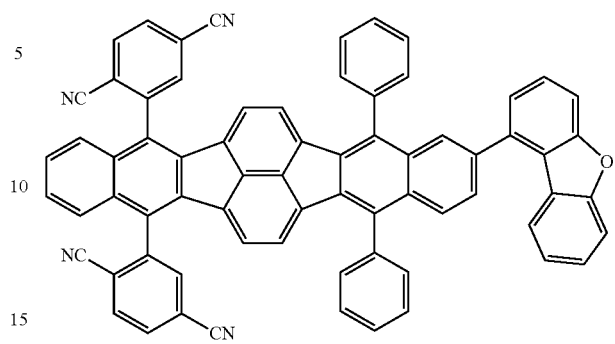
B23
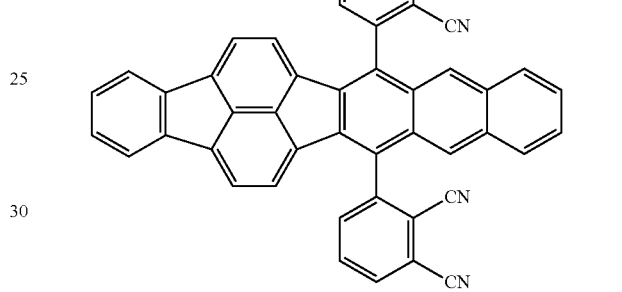
C1
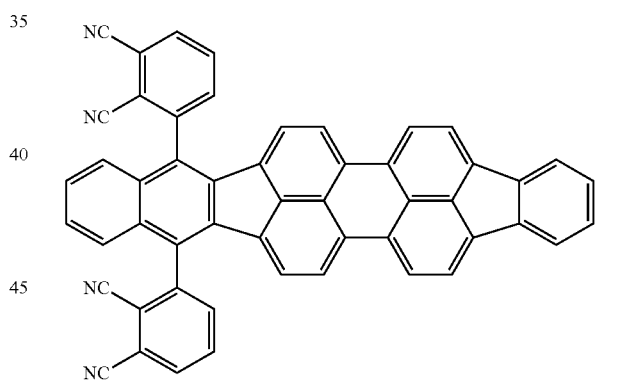
C2
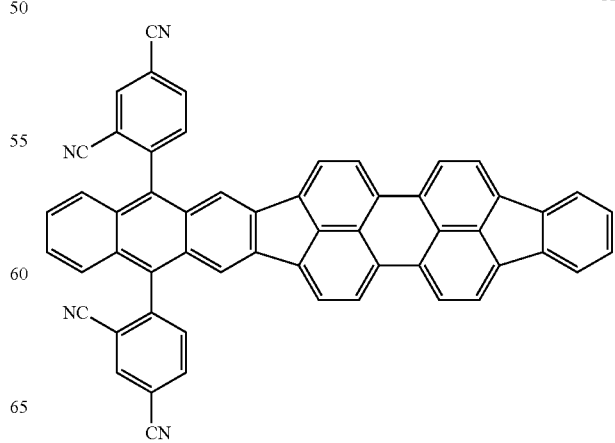

C3
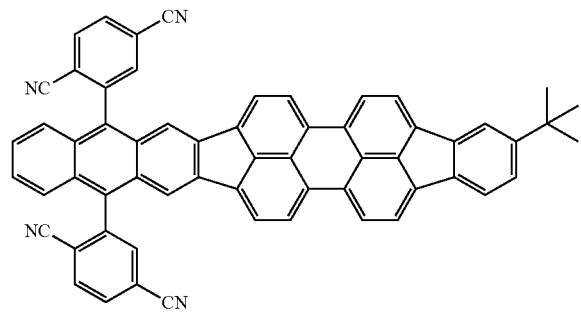
C7
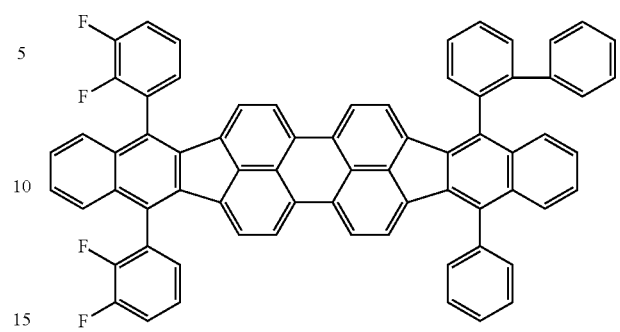
C4
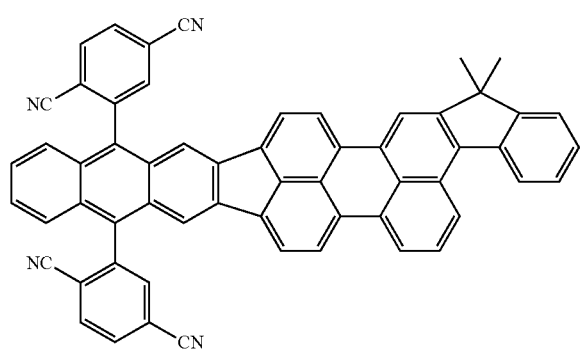
C8
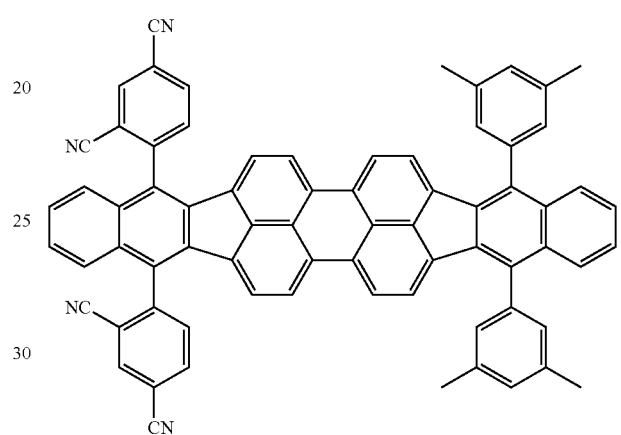
C5
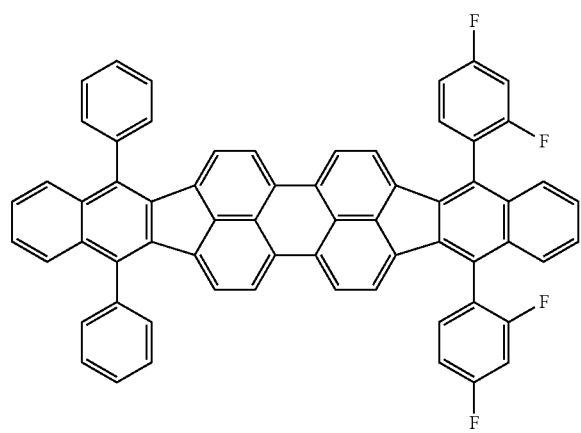
C9
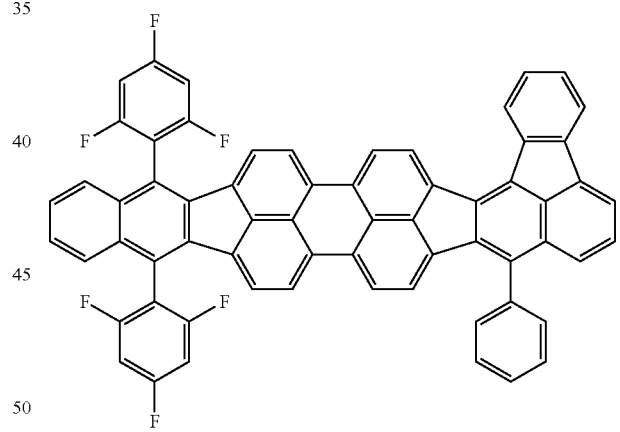
C6
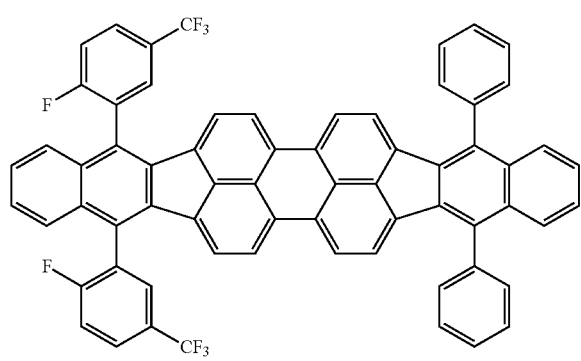
C10
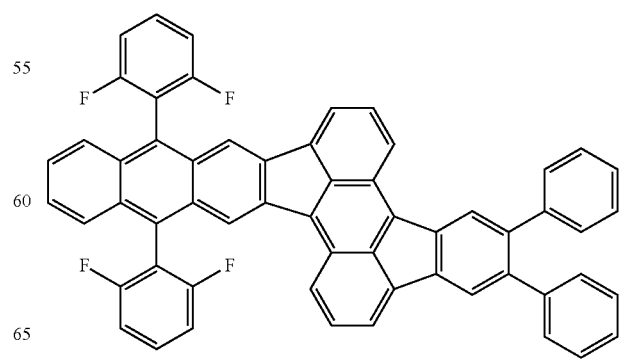

-continued
C11
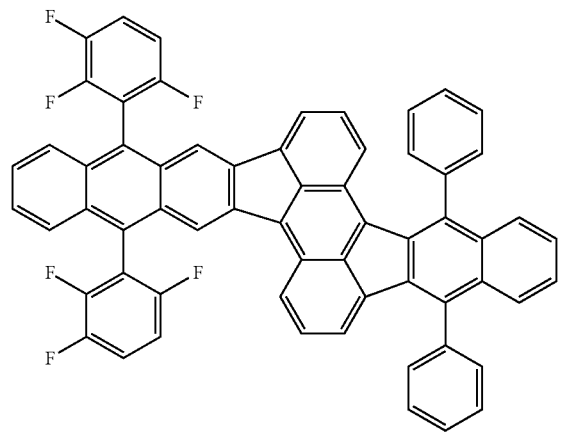
C12
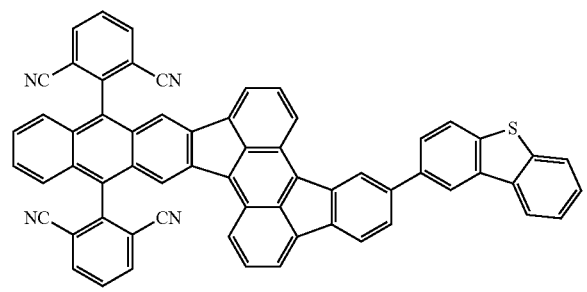
C13
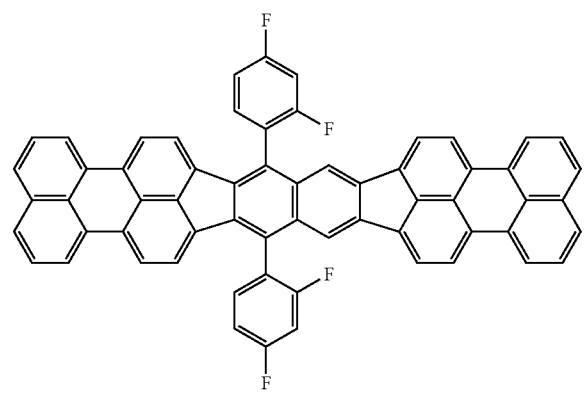
C14
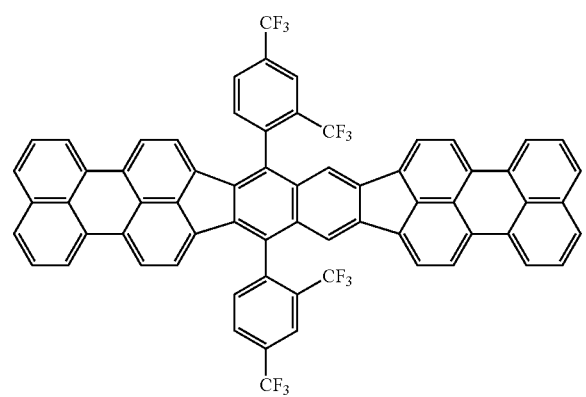
-continued
C15
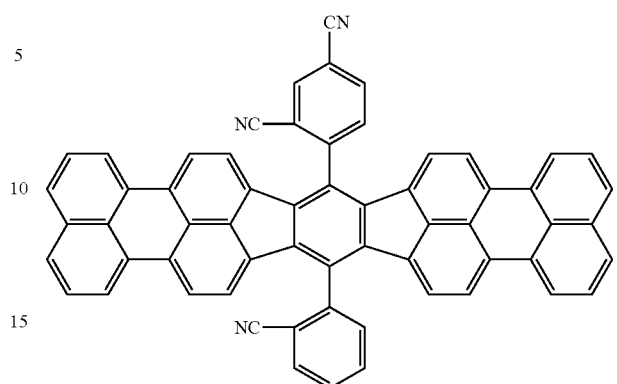
C16
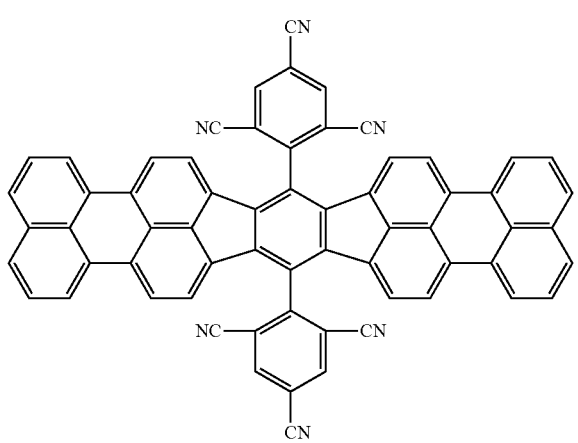
C17
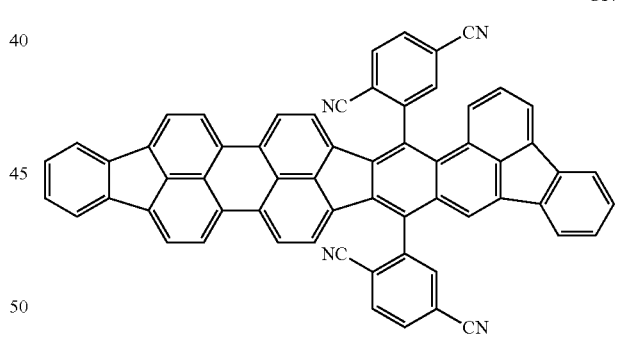
C18
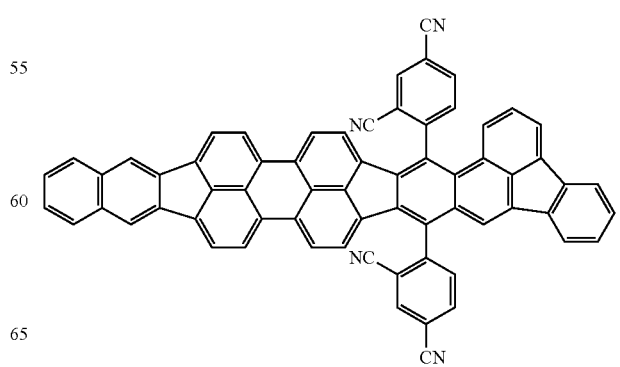

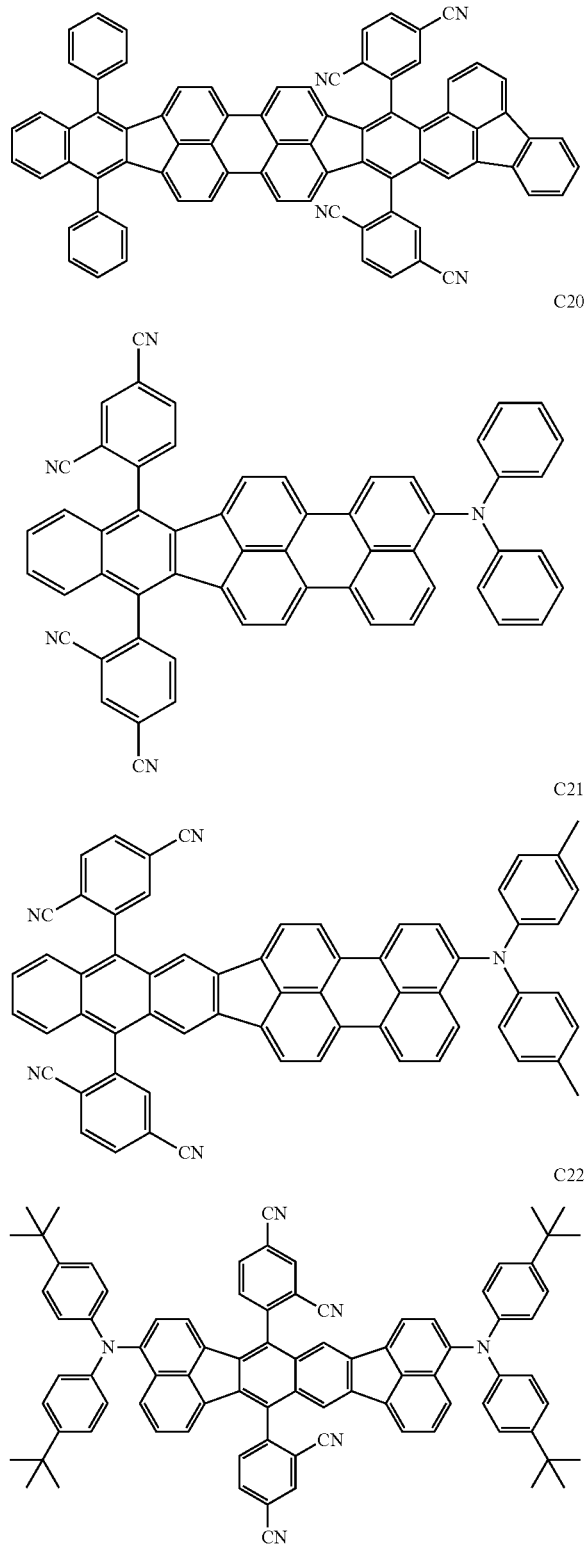

Among the above exemplary compounds, the exemplary compounds that belong to the A group are compounds in which the ring A is a polycyclic aromatic hydrocarbon having a fluoranthene skeleton and having 16 to 40 carbon atoms. The π conjugation length of the basic skeleton itself constituted by the ring A corresponds to a band gap of a blue light emission region. That is, such a compound is suitable for blue dopants as a light-emitting material.

On the other hand, among the above exemplary compounds, the exemplary compounds that belong to the B group are compounds in which the n conjugation length of the basic skeleton itself constituted by the ring A corresponds to a band gap of a green light emission region and in which the substituent allows the emission region to correspond to a green region. That is, such a compound is suitable for green dopants as a light-emitting material.

Among the above exemplary compounds, the exemplary compounds that belong to the C group are compounds in which the n conjugation length of the basic skeleton itself constituted by the ring A corresponds to a band gap of a red light emission region and in which the substituent allows the emission region to correspond to a red region. That is, such a compound is suitable for red dopants as a light-emitting material.

In this specification, the blue dopant refers to a light-emitting material having a peak wavelength of 430 nm to 480 nm in an emission spectrum. The green dopant refers to a light-emitting material having a peak wavelength of 500 nm to 570 nm in an emission spectrum. The red dopant refers to a light-emitting material having a peak wavelength of 580 nm to 680 nm in an emission spectrum.

Organic Light-Emitting Element

Hereafter, an organic light-emitting element according to an embodiment of the present disclosure will be described.

The organic light-emitting element according to this embodiment at least includes an anode and a cathode, which are a pair of electrodes, and an organic compound layer disposed between the electrodes. In the organic light-emitting element according to this embodiment, the organic compound layer may have a single-layer structure or a multilayer structure including a plurality of layers as long as the organic compound layer includes a light-emitting layer.

When the organic compound layer has a multilayer structure including a plurality of layers, the organic compound layer may include, in addition to the light-emitting layer, a hole injection layer, a hole transport layer, an electron blocking layer, a hole/exciton blocking layer, an electron transport layer, and an electron injection layer. The light-emitting layer may have a single-layer structure or a multilayer structure including a plurality of layers.

In the organic light-emitting element according to this embodiment, the organic compound according to this embodiment is contained in at least one layer of the organic compound layer. Specifically, the organic compound according to this embodiment is contained in any of the hole injection layer, the hole transport layer, the electron blocking layer, the light-emitting layer, the hole/exciton blocking layer, the electron transport layer, and the electron injection layer. The organic compound according to this embodiment may be contained in the light-emitting layer.

In the organic light-emitting element according to this embodiment, when the organic compound according to this embodiment is contained in the light-emitting layer, the light-emitting layer may be a layer formed of only the organic compound according to this embodiment or may be a layer formed of the organic compound according to this embodiment and other compounds. When the light-emitting layer is a layer formed of the organic compound according to this embodiment and other compounds, the organic compound according to this embodiment may be used as a host of the light-emitting layer or a guest of the light-emitting layer. Alternatively, the organic compound may be used as an assist material that can be contained in the light-emitting layer. Herein, the host refers to a compound having the highest mass ratio among the compounds that form the light-emitting layer. The guest refers to a compound that has a lower mass ratio than the host and that is responsible for main light emission among the compounds that form the light-emitting layer. The assist material refers to a compound that has a lower mass ratio than the host and that assists light emission of the guest among the compounds that form the light-emitting layer. The assist material is also referred to as a second host.

When the organic compound according to this embodiment is used as a guest of the light-emitting layer, the concentration of the guest may be 0.01 mass % or more and 20 mass % or less or may also be 0.1 mass % or more and 5 mass % or less relative to the whole light-emitting layer.

When the organic compound according to this embodiment is used as a guest of the light-emitting layer, a material having a higher LUMO energy level than the organic compound according to this embodiment (a material having a LUMO energy level closer to the vacuum level) may be used as the host. This is because when a material having a higher LUMO energy level than the organic compound according to this embodiment is used as the host, the organic compound according to this embodiment can accept a larger amount of electrons supplied to the host of the light-emitting layer.

As a result of thorough studies, the present inventors have found that when the organic compound according to this embodiment is used as the host or guest of the light-emitting layer, in particular, as the guest of the light-emitting layer, an element that produces an optical output with high efficiency and high luminance and that has very high durability is provided. This light-emitting layer may have a single-layer structure or a multilayer structure, or an emission color of this embodiment can be mixed with another color by adding a light-emitting material having another emission color. The multilayer structure refers to a state in which the light-emitting layer and another light-emitting layer are stacked. In this case, the emission color of the organic light-emitting element is not limited to red. The emission color may be specifically white or an intermediate color. In the case of white, the other light-emitting layer emits light having a color other than red, such as blue or green. The light-emitting layers are formed by a method such as vapor deposition or coating. The details of the method will be specifically described in Examples below.

The organic compound according to this embodiment can be used as a material for organic compound layers other than the light-emitting layer that constitute the organic light-emitting element according to this embodiment. Specifically, the organic compound may be used as a material for, for example, electron transport layers, electron injection layers, hole transport layers, hole injection layers, and hole blocking layers.

The organic compound according to this embodiment may be used in combination with, for example, a publicly known low-molecular-weight or high-molecular-weight compound such as a hole injection or transport compound, a compound serving as the host, a luminous compound, an electron injection or transport compound if necessary. Examples of these compounds will be described below.

A hole injection or transport material is suitably a material having a high hole mobility such that injection of holes from the anode is facilitated and the injected holes can be transported to the light-emitting layer. The hole injection or transport material is also suitably a material having a high glass transition temperature in order to suppress the deterioration of the film quality, such as crystallization in the organic light-emitting element. Examples of the low-molecular-weight or high-molecular-weight material having hole injectability or transportability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used for the electron blocking layer. Non-limiting specific examples of the compound used as the hole injection or transport material are shown below.

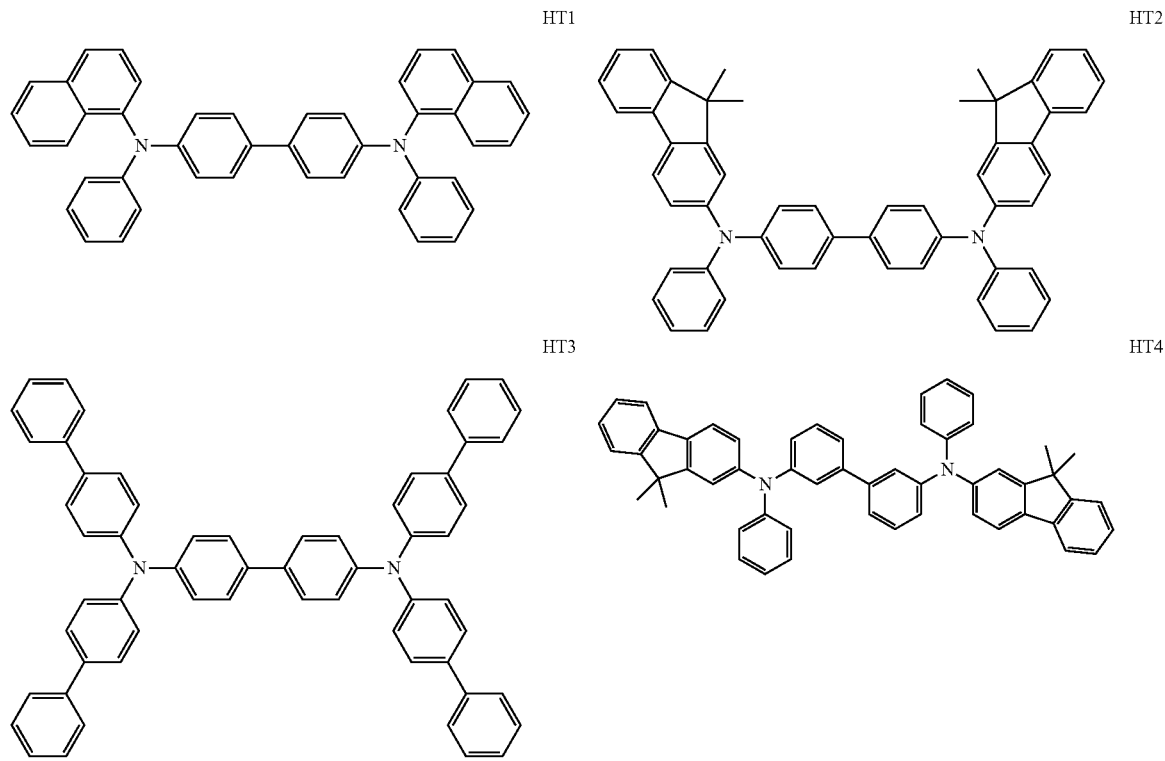

-continued
HT5
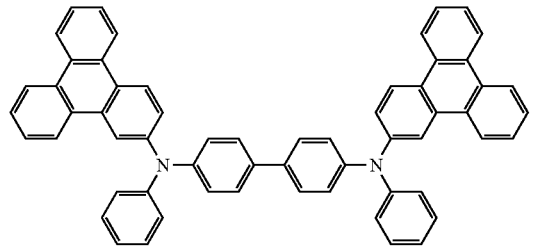
HT6
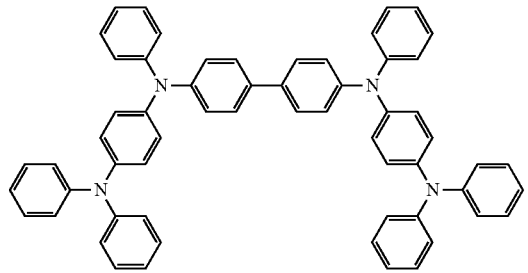
HT7
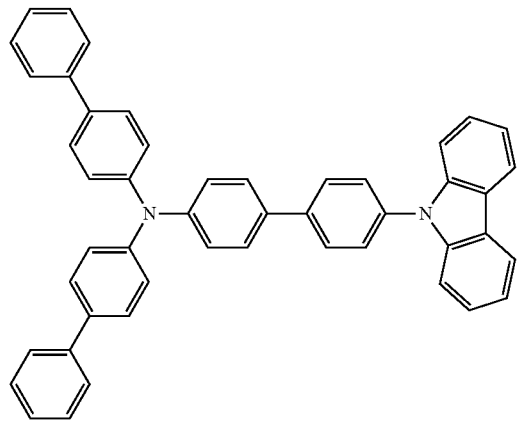
HT8
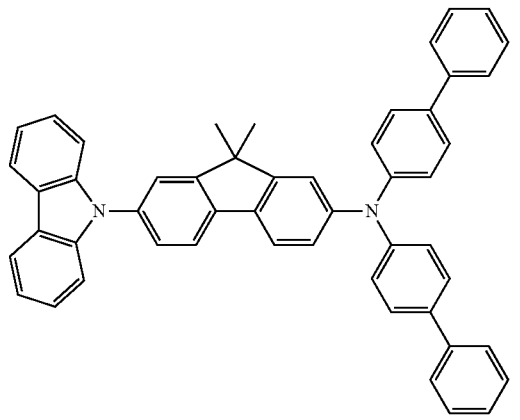
HT9
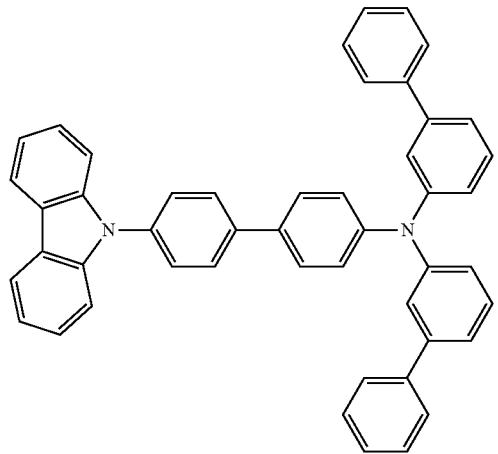
HT10
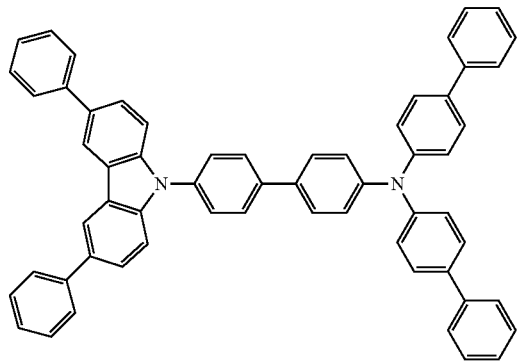
HT11
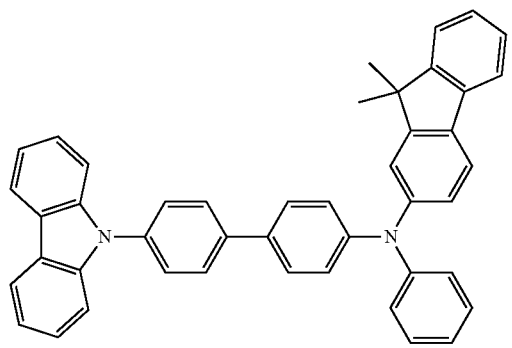
HT12
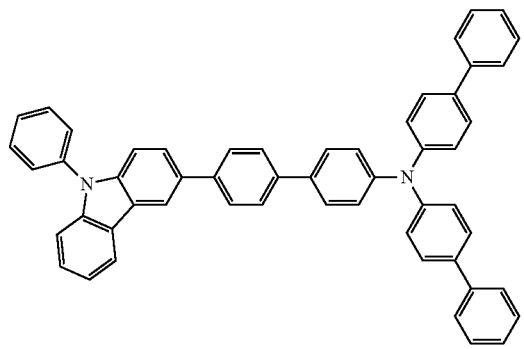

-continued

HT13
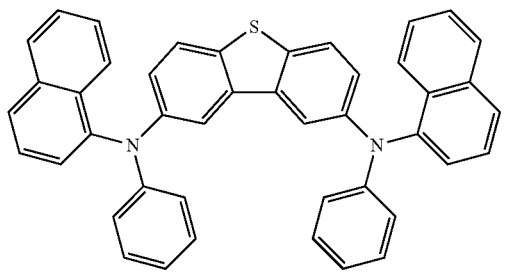

HT14
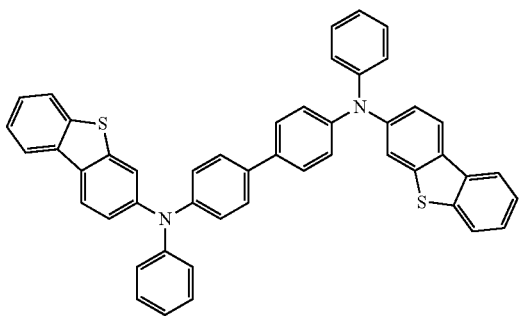

HT15
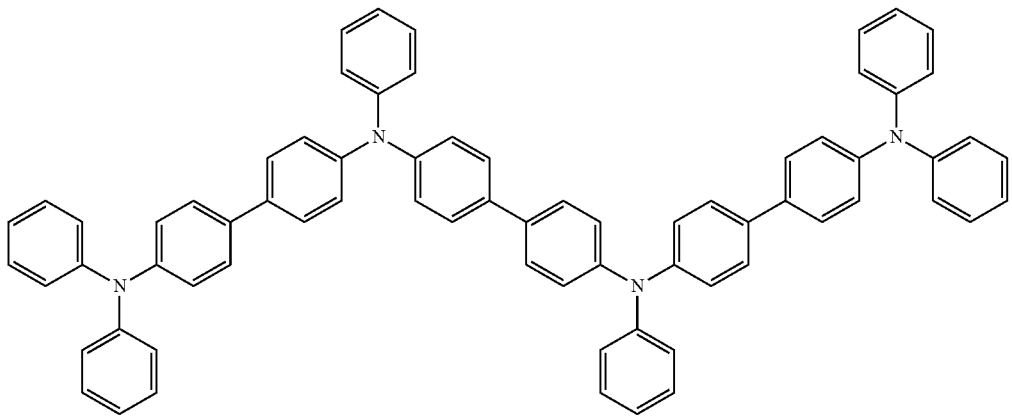

HT16
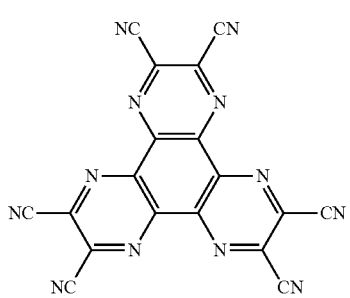

HT17
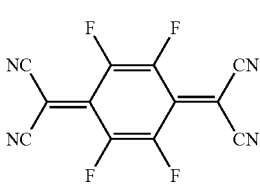

HT18
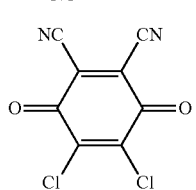

HT19
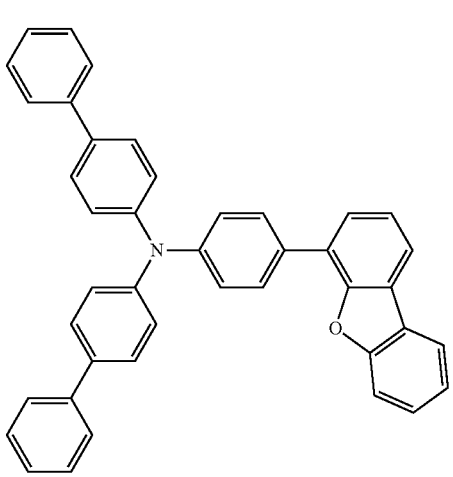

Examples of the light-emitting material mainly concerned with a light-emitting function include, in addition to the organic compound represented by the formula [1], fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

When a mixture layer is formed with another light-emitting material using the organic compound according to this embodiment or when light-emitting layers are stacked, the other light-emitting material also suitably has a low HOMO/LUMO energy level. This is because if the HOMO/LUMO energy level is high, formation of a quenching component or a trap level may occur, such as the case where the other light-emitting material forms an exciplex with the organic compound according to this embodiment.

Non-limiting specific examples of the compound used as the light-emitting material are shown below.

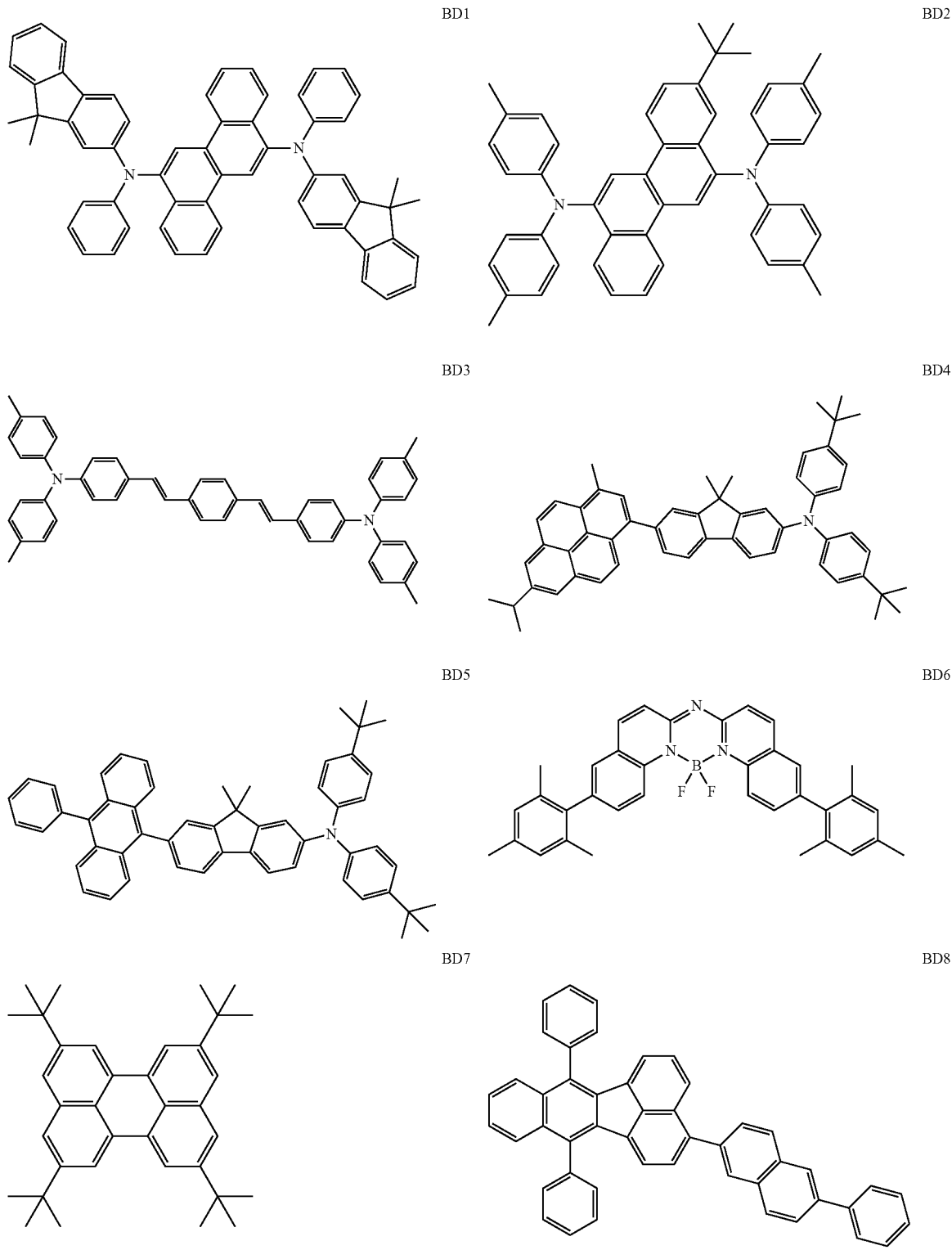

-continued
BD9
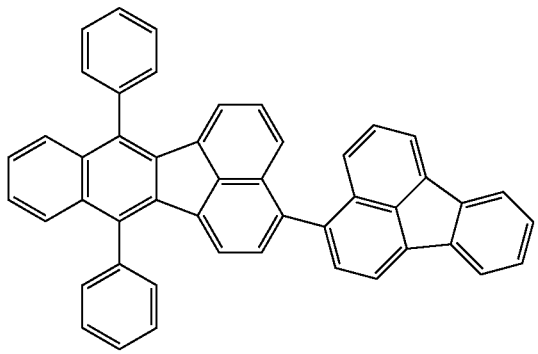
BD10
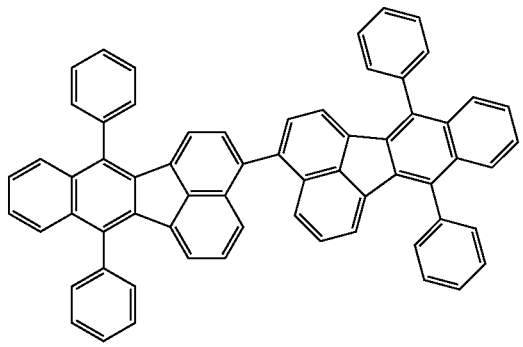
BD11
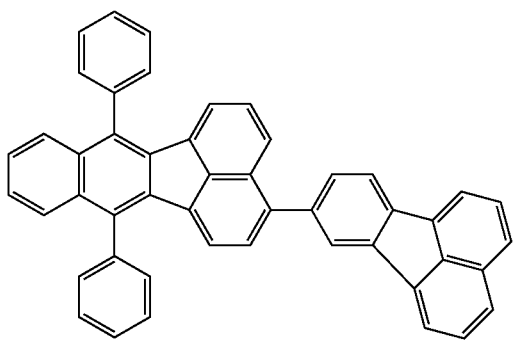
GD1
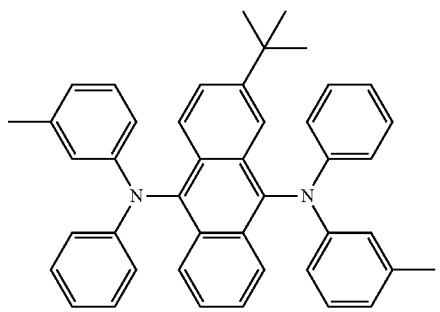
GD2
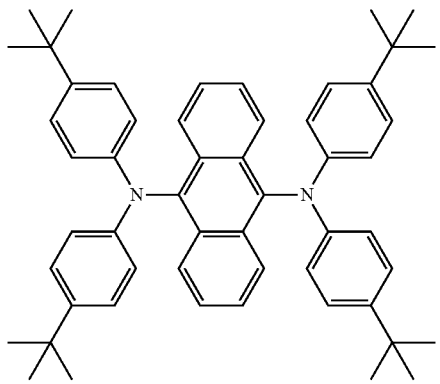
GD3
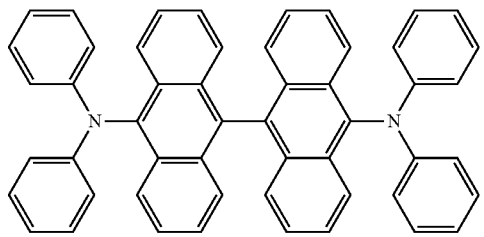
GD4
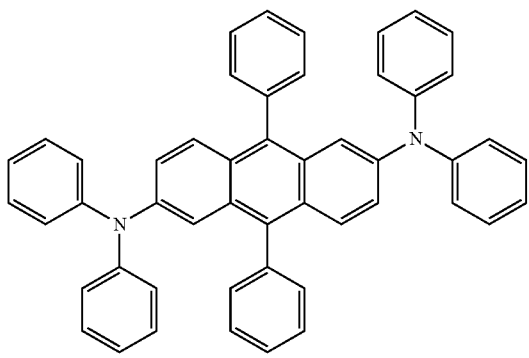
GD5
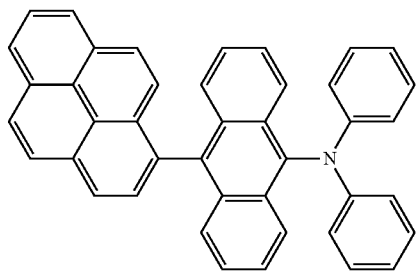

-continued
GD6
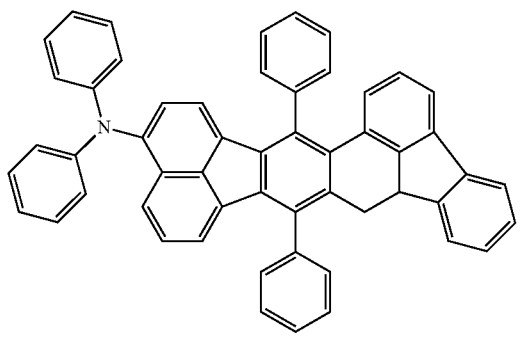
GD7
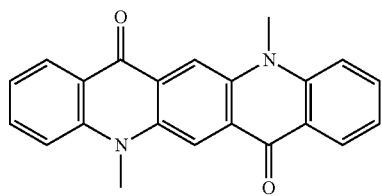
GD8
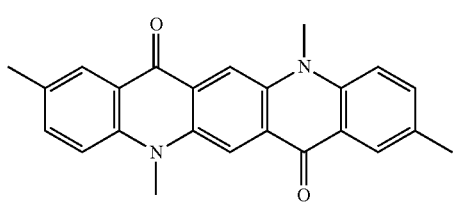
GD9
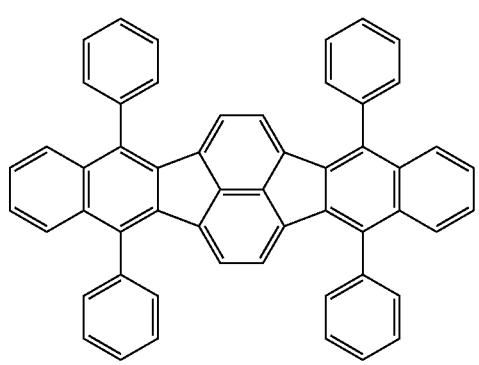
GD10
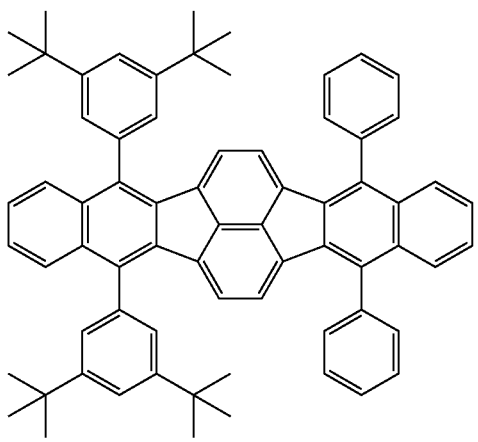
GD11
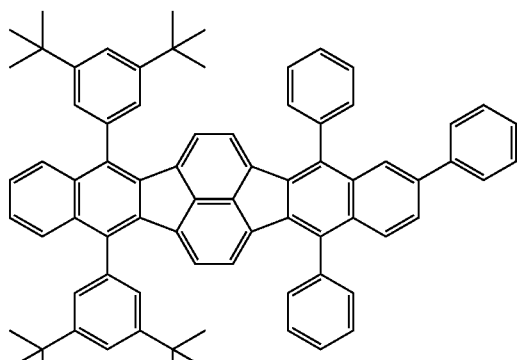
GD12
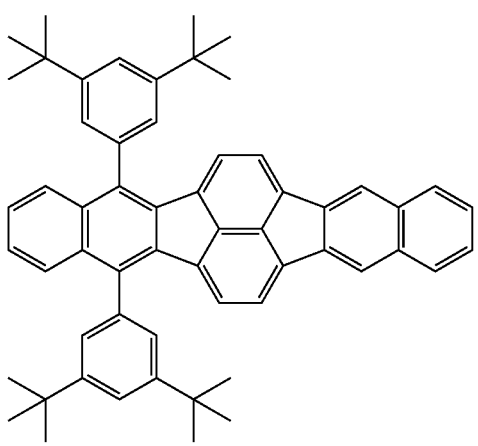
RD1
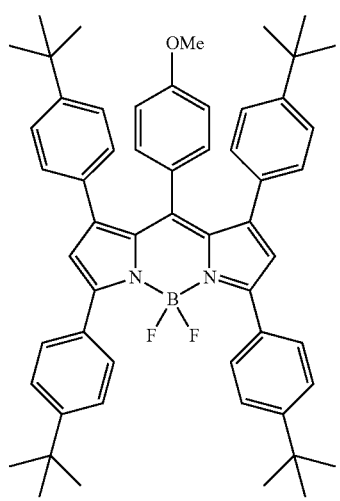

-continued
RD2
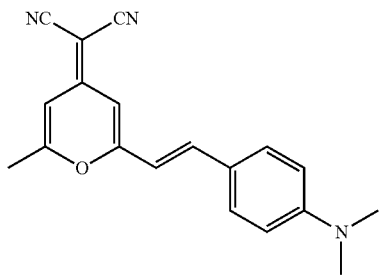
RD3
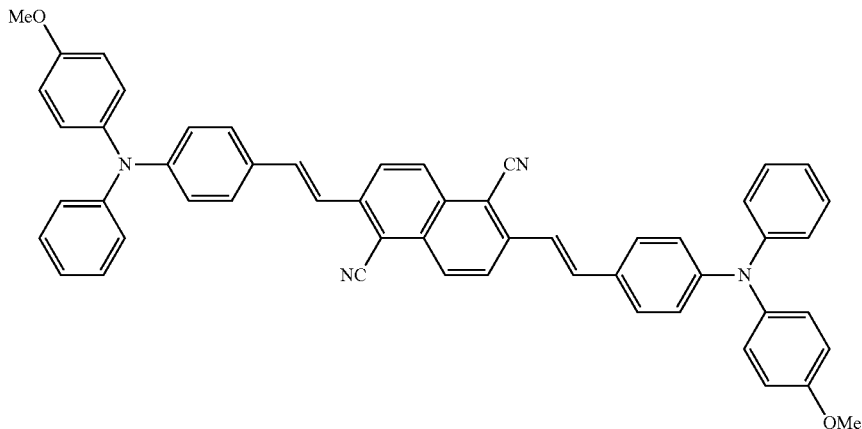
RD4
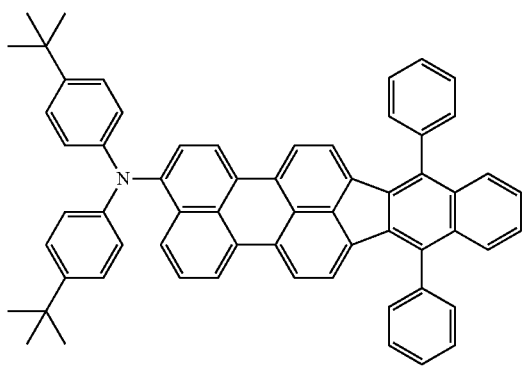
RD5
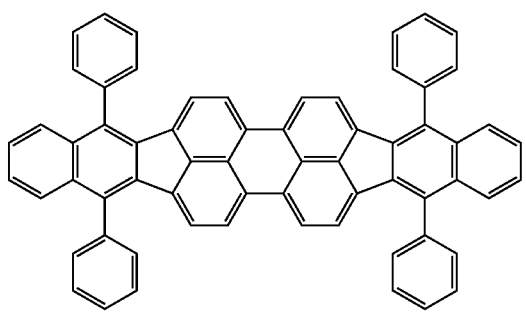
RD6
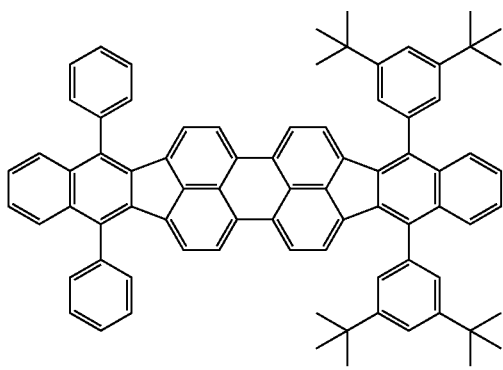
RD7
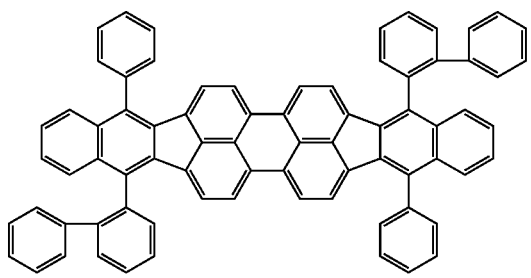

RD8

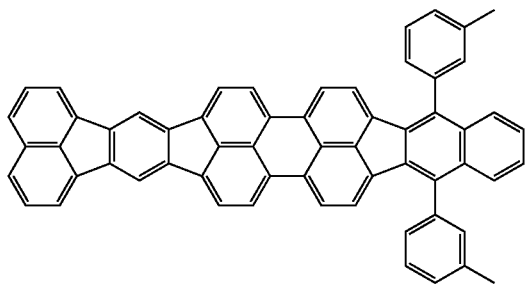

Examples of the light-emitting-layer host or light emission assist material contained in the light-emitting layer include aromatic hydrocarbon compounds and derivatives thereof, carbazole derivatives, dibenzofuran derivatives, dibenzothiophene derivatives, organoaluminum complexes such as tris(8-quinolinolato)aluminum, and organoberyllium complexes.

The host material is suitably formed of a hydrocarbon and suitably has a low HOMO/LUMO energy level. This is because if the host material contains a hetero atom such as a nitrogen atom, the HOMO/LUMO energy level increases, and formation of a quenching component or a trap level may occur, such as the case where the host material forms an exciplex with the organic compound according to this embodiment.

In particular, the host material may have an anthracene, tetracene, perylene, or pyrene skeleton in its molecular skeleton. This is because the host material is formed of a hydrocarbon as described above and also has an S1 energy capable of causing sufficient energy transfer to the organic compound according to this embodiment.

Non-limiting specific examples of the compound used as the light-emitting-layer host or light emission assist material contained in the light-emitting layer are shown below.

EM1

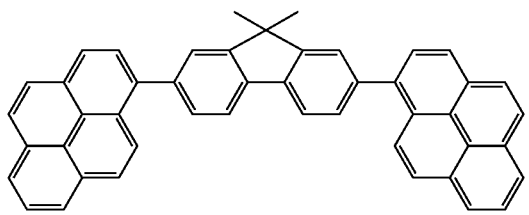

EM2

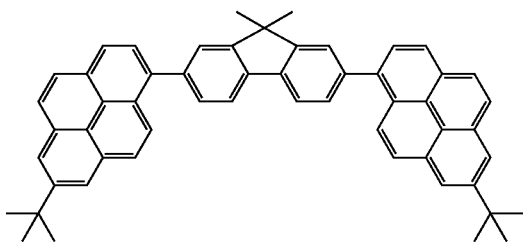

EM3

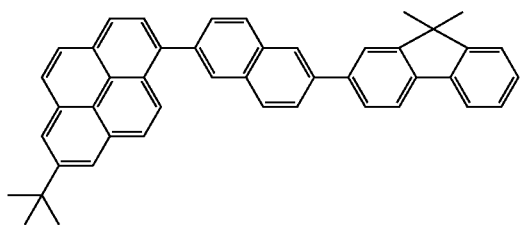

EM4

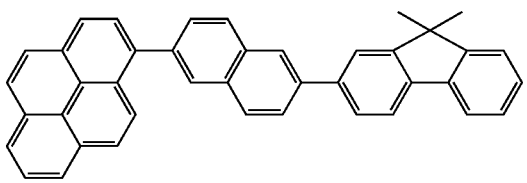

EM5

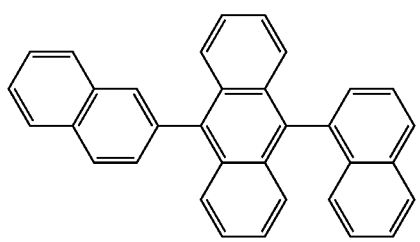

EM6

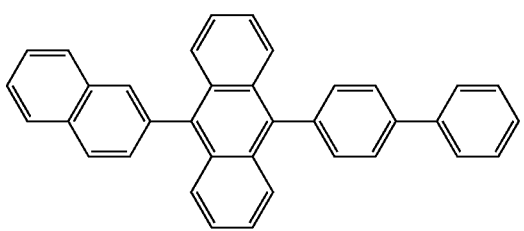

EM7
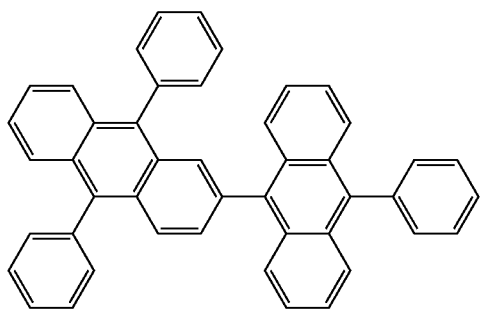
EM8
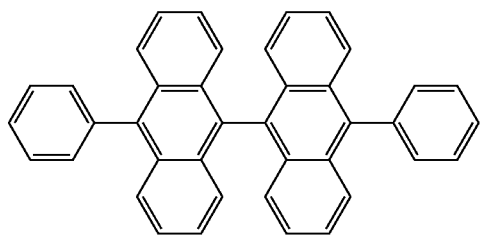
EM9
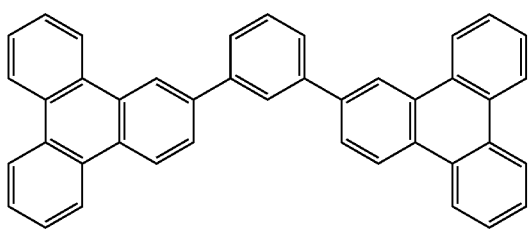
EM10
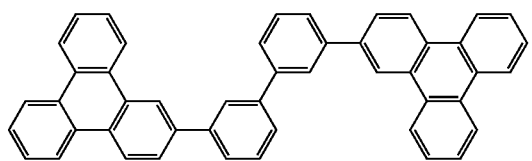
EM11
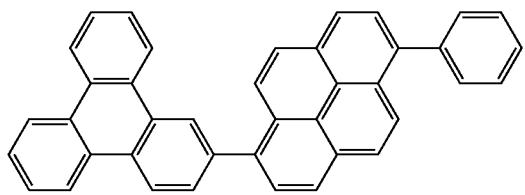
EM12
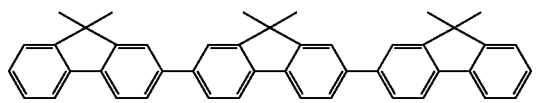
EM13
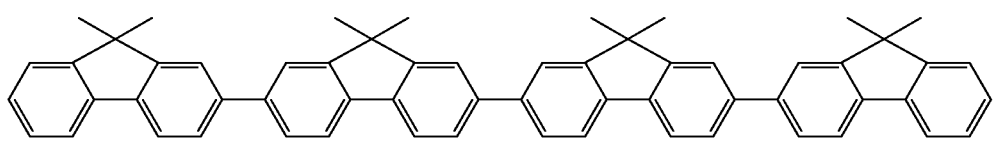
EM14
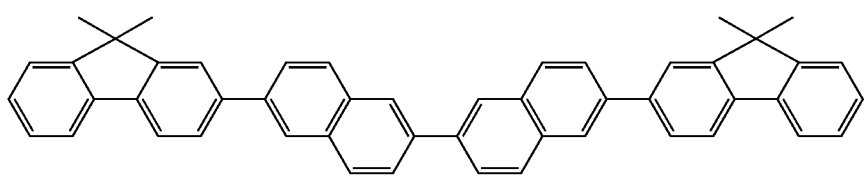
EM15
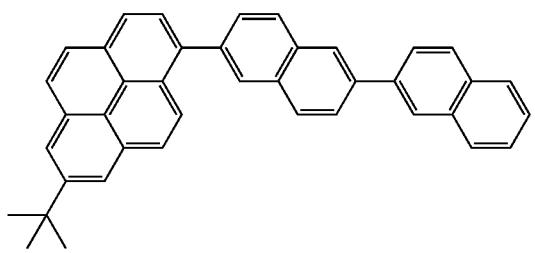
EM16
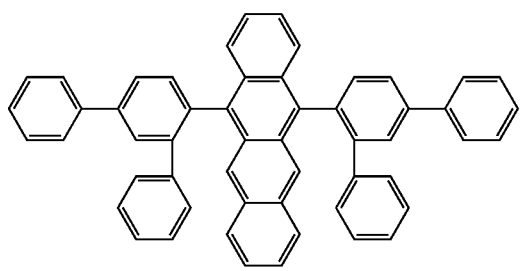

-continued
EM17
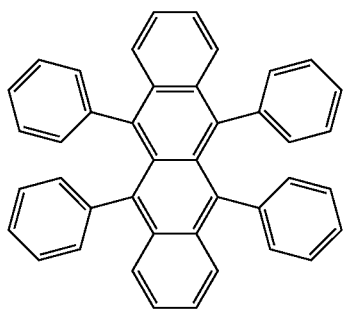
EM18
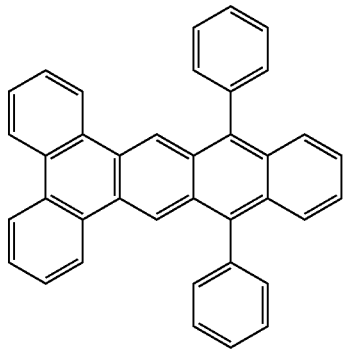
EM19
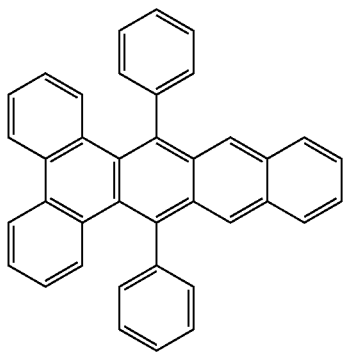
EM20
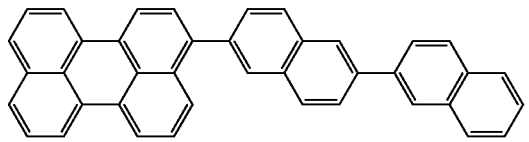
EM21
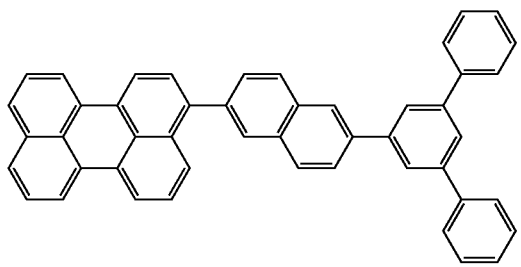
EM22
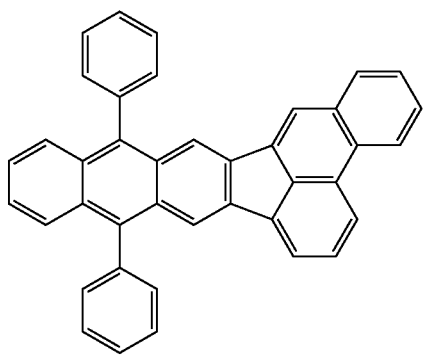
EM23
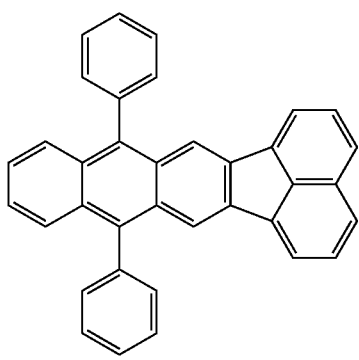
EM24
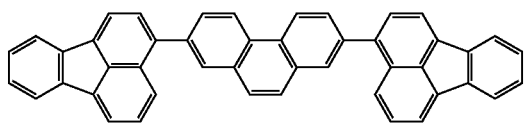

-continued

EM25

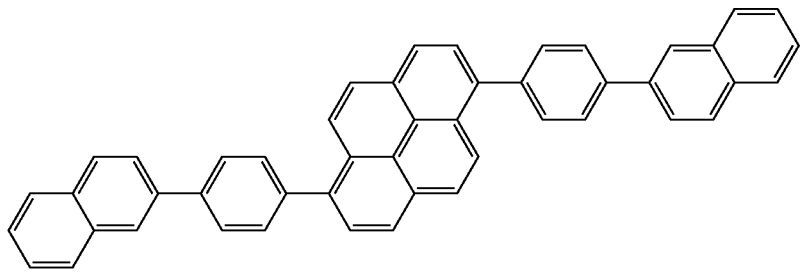

EM26

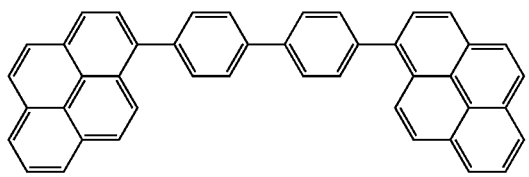

EM27

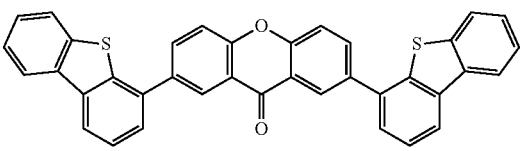

EM28

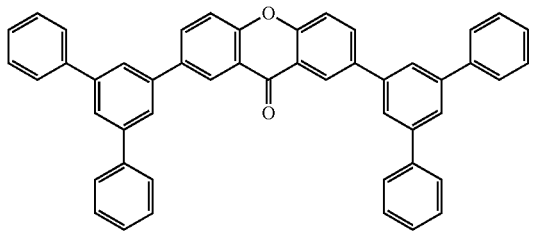

EM29

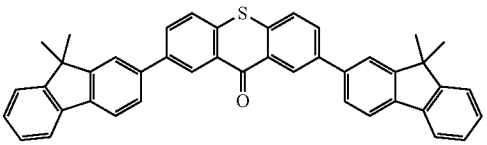

EM30

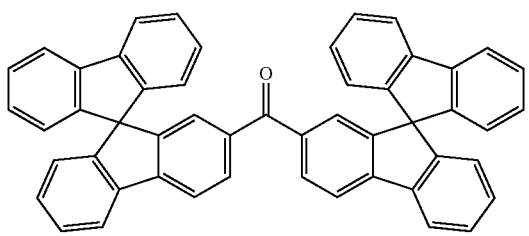

EM31

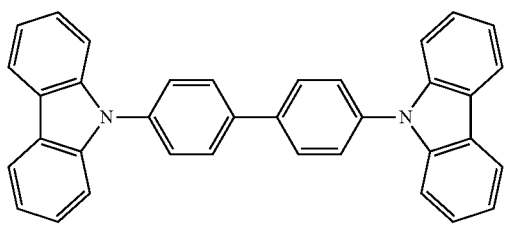

EM32

The electron transport material can be freely selected from materials capable of transporting electrons injected from the cathode to the light-emitting layer. The electron transport material is selected in consideration of, for example, the balance with the hole mobility of the hole transport material. Examples of the material having electron transportability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (e.g., fluorene derivatives, naphthalene derivatives, chrysene derivatives, and anthracene derivatives). The above electron transport material is also suitably used for the hole blocking layer. Non-limiting specific examples of the compound used as the electron transport material are shown below.

ET1

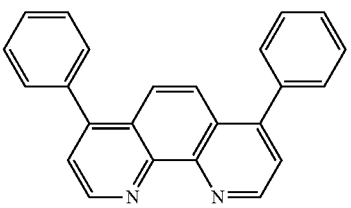

-continued
ET2
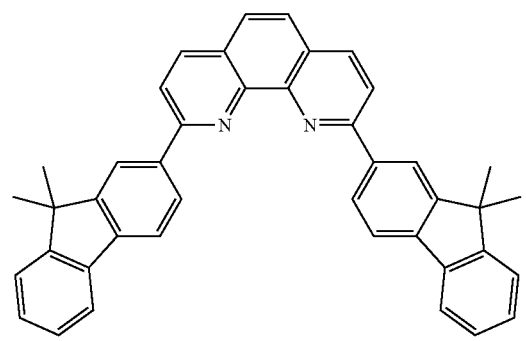
ET3
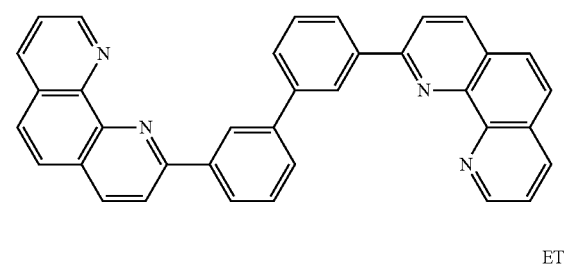
ET4
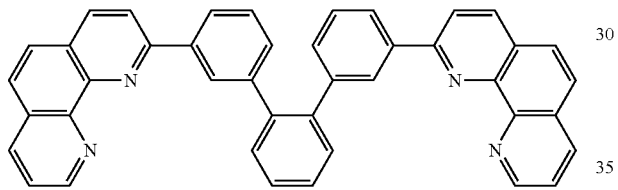
ET5
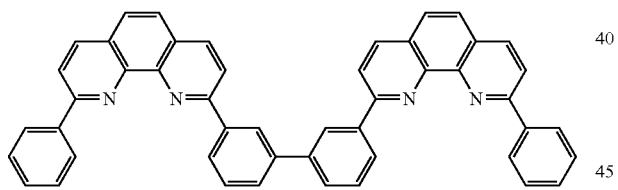
ET6
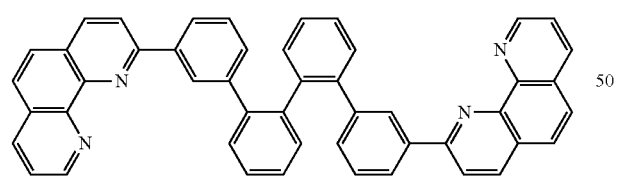
ET7
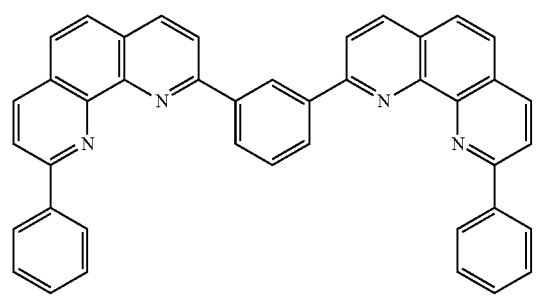
-continued
ET8
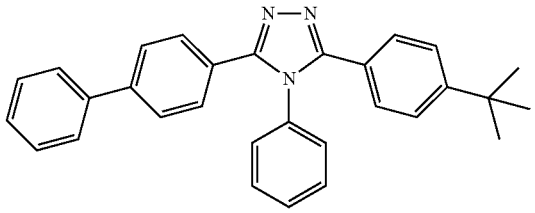
ET9
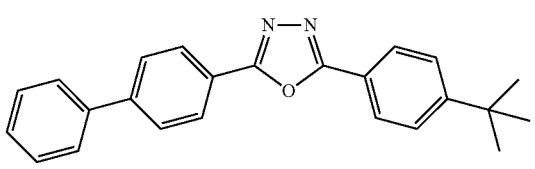
ET10
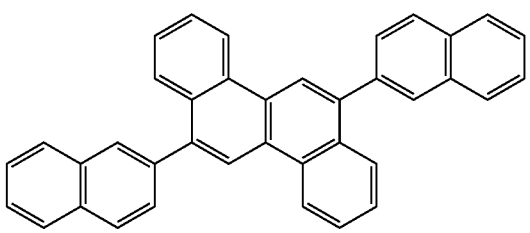
ET11
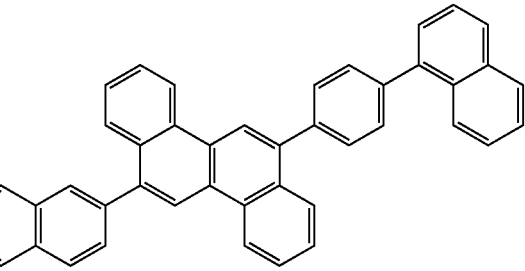
ET12
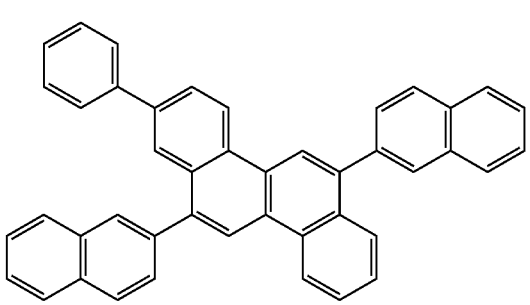
ET13
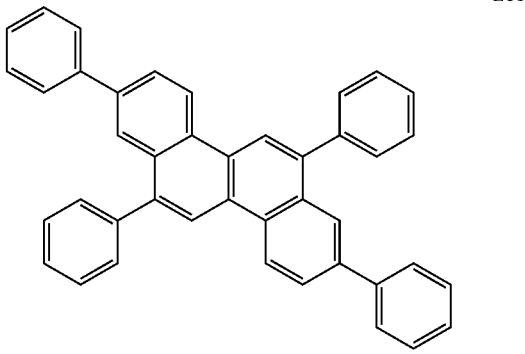

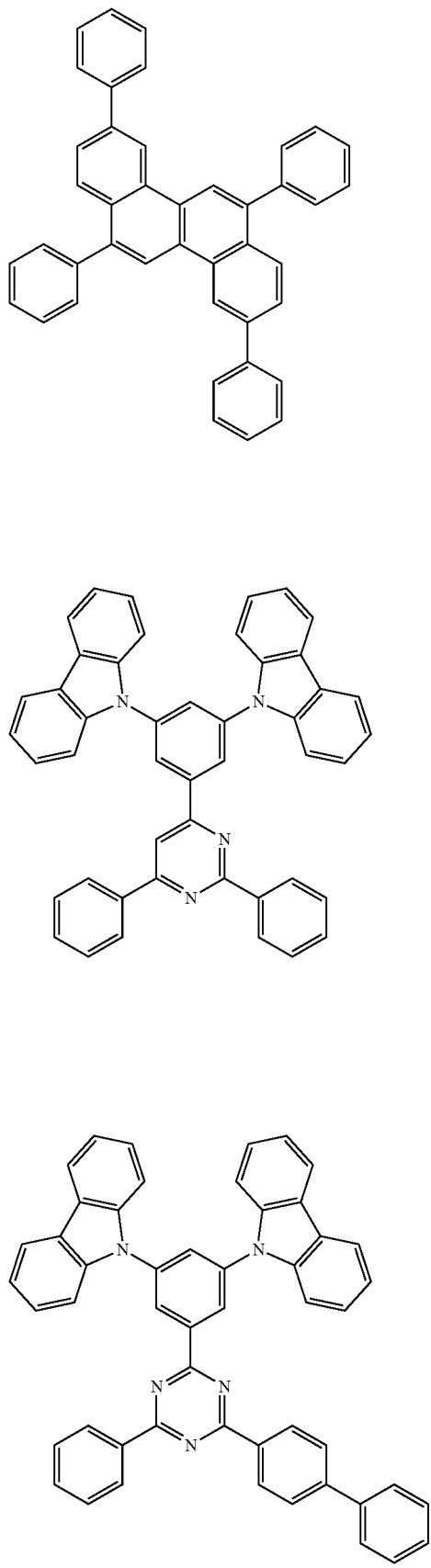

ET22
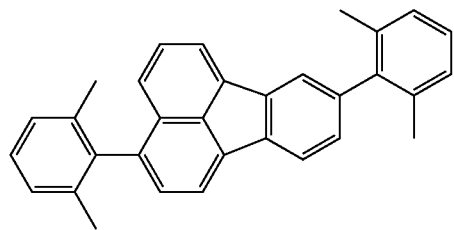

ET23
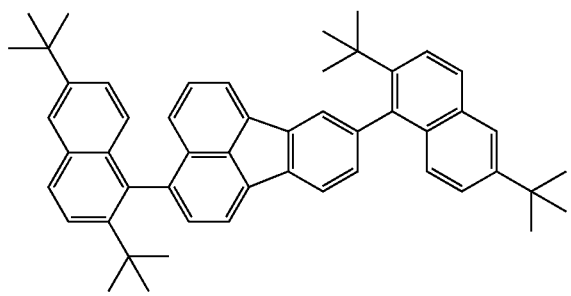

Configuration of Organic Light-Emitting Element

The organic light-emitting element is provided by forming an anode, an organic compound layer, and a cathode on a substrate. For example, a protective layer and a color filter may be disposed on the cathode. If the color filter is disposed, a planarizing layer may be disposed between the protective layer and the color filter. The planarizing layer may be formed of, for example, an acrylic resin.

Substrate

The substrate is formed of, for example, quartz, glass, silicon wafer, resin, or metal. A switching element such as a transistor and a wire may be disposed on the substrate, and an insulating layer may be disposed thereon. The insulating layer may be formed of any material as long as contact holes can be formed to establish electrical connection between the anode and the wire and the anode can be insulated from wires to which the anode is not connected.

Examples of the material for the insulating layer include resins such as polyimide, silicon oxide, and silicon nitride.

Electrode

The electrode may be a pair of electrodes. The pair of electrodes may be an anode and a cathode. When an electric field is applied in a direction in which the organic light-emitting element emits light, the electrode having a high electric potential is an anode and the other electrode is a cathode. It can also be said that the electrode that supplies holes to the light-emitting layer is an anode and the electrode that supplies electrons is a cathode.

The material for the anode desirably has as high a work function as possible. Examples of the material for the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Conductive polymers such as polyaniline, polypyrrole, and polythiophene can also be used.

These electrode materials may be used alone or in combination of two or more. The anode may have a single-layer structure or a multilayer structure.

When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the materials are not limited thereto. The electrode can be formed by photolithography.

On the other hand, the material for the cathode desirably has a low work function. Examples of the material for the cathode include alkali metals such as lithium; alkaline earth metals such as calcium; elemental metals such as aluminum, titanium, manganese, silver, lead, and chromium; mixtures containing these metals; alloys of these metals, such as magnesium-silver, aluminum-lithium, aluminum-magnesium, silver-copper, and zinc-silver; and metal oxides such as indium tin oxide (ITO). These electrode materials may be used alone or in combination of two or more. The cathode may have a single-layer structure or a multilayer structure. In particular, silver may be used and a silver alloy may also be used to suppress aggregation of silver. The silver alloy may have any mixing ratio such as 1:1 as long as the aggregation of silver can be suppressed.

Any device may be employed, such as a top emission device obtained by using a conductive oxide layer made of, for example, ITO as a cathode or a bottom emission device obtained by using a reflective electrode made of, for example, aluminum (Al) as a cathode. The method for forming a cathode is not particularly limited. For example, a DC and AC sputtering method is suitably employed because good film coverage can be achieved to readily reduce the resistance.

Protective Layer

A protective layer may be disposed on the cathode. For example, a glass plate including a moisture absorbent is bonded to the cathode. This suppresses permeation of water or the like into the organic compound layer and thus can suppress occurrence of display defects. In another embodiment, a passivation film made of silicon nitride or the like may be disposed on the cathode to suppress permeation of water or the like into the organic compound layer. For example, after the formation of the cathode, the resulting substrate may be transferred to another chamber without breaking the vacuum, and a silicon nitride film having a thickness of 2 m may be formed by a chemical vapor deposition (CVD) method to provide a protective layer. After the film formation by the CVD method, a protective layer may be disposed by an atomic layer deposition method (ALD method).

Color Filter

A color filter may be disposed on the protective layer. For example, a color filter provided in consideration of the size of organic light-emitting elements is disposed on another substrate, and this substrate may be bonded to the substrate on which the organic light-emitting elements have been disposed. Alternatively, a color filter may be patterned on the above-described protective layer by photolithography. The color filter may be formed of a polymer.

Planarizing Layer

A planarizing layer may be disposed between the color filter and the protective layer. The planarizing layer may be formed of an organic compound. The organic compound may be a low-molecular-weight organic compound or may be a high-molecular-weight organic compound, but is suitably a high-molecular-weight organic compound.

The planarizing layer may be disposed on and below the color filter, and both the planarizing layers may be formed of the same material or different materials. Specific examples of the material include polyvinylcarbazole resin, polycarbonate resin, polyester resin, ABS resin, acrylic resin, polyimide resin, phenolic resin, epoxy resin, silicone resin, and urea resin.

Counter Substrate

A counter substrate may be disposed on the planarizing layer. The name of the counter substrate is derived from the fact that the counter substrate is disposed at a position corresponding to that of the above-described substrate.

The counter substrate may be formed of the same material as the above-described substrate.

Organic Compound Layer

The organic compound layers (e.g., a hole injection layer, a hole transport layer, an electron blocking layer, a light-emitting layer, a hole blocking layer, an electron transport layer, and an electron injection layer) that constitute the organic light-emitting element according to an embodiment of the present disclosure are formed by the following method.

The organic compound layers that constitute the organic light-emitting element according to an embodiment of the present disclosure can be formed by a dry process such as a vacuum vapor deposition method, an ionized vapor deposition method, a sputtering method, or a method using plasma. Instead of the dry process, a wet process in which an organic compound is dissolved in an appropriate solvent and a layer is formed by a publicly known coating method (e.g., spin coating, dipping, a casting method, a Langmuir-Blodgett (LB) method, or an ink jet method) can also be employed.

When a layer is formed by, for example, a vacuum vapor deposition method or a solution coating method, crystallization or the like is unlikely to occur and the resulting layer has high stability over time. When a layer is formed by a coating method, the layer can be formed by using an appropriate binder resin in combination.

Non-limiting examples of the binder resin include polyvinylcarbazole resin, polycarbonate resin, polyester resin, ABS resin, acrylic resin, polyimide resin, phenolic resin, epoxy resin, silicone resin, and urea resin.

These binder resins may be used alone as a homopolymer or in combination as a mixture of two or more as a copolymer. Furthermore, publicly known additives such as a plasticizer, an antioxidant, and an ultraviolet absorber may be optionally used in combination.

Application of organic light-emitting element according to embodiment of the present disclosure The organic light-emitting element according to an embodiment of the present disclosure can be used as a member of display apparatuses and lighting apparatuses. In addition, the organic light-emitting element may be used as, for example, an exposure light source for electrophotographic image forming apparatuses, a backlight of liquid crystal display apparatuses, and a light-emitting device including a white light source having a color filter.

The display apparatus may be an image information processing apparatus that includes an image input unit which inputs image information from an area CCD, a linear CCD, a memory card, or the like and an information processing unit which processes the input information and that displays the input image on a display unit. The display apparatus includes a plurality of pixels, and at least one of the plurality of pixels may include the organic light-emitting element according to this embodiment and a transistor connected to the organic light-emitting element.

The display unit included in an image pickup apparatus or an ink jet printer may have a touch panel function. The touch panel function may be driven by any method such as a method that uses infrared rays, electrostatic capacitance, a resistive film, or electromagnetic induction. The display apparatus may be used as a display unit of multifunction printers.

Next, a display apparatus according to this embodiment will be described with reference to the attached drawings. FIG. 2 is a schematic sectional view illustrating an example of a display apparatus including organic light-emitting elements and TFT elements connected to the organic light-emitting elements. The TFT element is an example of active elements.

The display apparatus 10 in FIG. 2 includes a substrate 11 made of glass or the like and a moistureproof film 12 that is disposed on the substrate 11 and protects TFT elements or organic compound layers. The display apparatus 10 also includes metal gate electrodes 13, gate insulating films 14, and semiconductor layers 15.

Each of the TFT elements 18 includes a semiconductor layer 15, a drain electrode 16, and a source electrode 17. An insulating film 19 is disposed on the TFT element 18. An anode 21 that constitutes an organic light-emitting element 26 and the source electrode 17 are connected to each other through a contact hole 20.

The form of electrical connection between electrodes (anode 21 and cathode 23) included in the organic light-emitting element 26 and electrodes (source electrode 17 and drain electrode 16) included in the TFT element 18 is not limited to the form illustrated in FIG. 2. That is, it suffices that one of the anode 21 and the cathode 23 are electrically connected to one of the source electrode 17 and the drain electrode 16 of the TFT element 18.

In the display apparatus 10 in FIG. 2, an organic compound layer 22 is illustrated as if having a single-layer structure, but may have a multilayer structure. A first protective layer 24 and a second protective layer 25 for suppressing the deterioration of the organic light-emitting element 26 are disposed on the cathode 23.

In the display apparatus 10 in FIG. 2, a transistor is used as a switching element. Instead, an MIM element may be used as a switching element.

The transistor used in the display apparatus 10 in FIG. 2 is not limited to transistors that use a single-crystal silicon wafer, but may be thin-film transistors including an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. The thin-film transistors are also referred to as TFT elements.

The transistor included in the display apparatus 10 in FIG. 2 may be formed in a substrate such as a Si substrate. Herein, the phrase "formed in a substrate" signifies that a transistor is produced by processing the substrate itself, such as a Si substrate. That is, a transistor formed in a substrate can be regarded as a transistor integrally formed with a substrate.

In the organic light-emitting element according to this embodiment, the emission luminance is controlled by a TFT that is an example of a switching element. When a plurality of such organic light-emitting elements are arranged in a plane, an image can be displayed using an emission luminance of each of the organic light-emitting elements. The switching element according to this embodiment is not limited to TFTs. The switching element may be a transistor formed of low-temperature polysilicon or an active matrix driver formed on a substrate such as a Si substrate. The phrase "on a substrate" may also refer to "in a substrate". The size of a display unit determines whether a transistor is disposed in a substrate or a TFT is used. For example, in the case of a size of about 0.5 inches, the organic light-emitting element may be disposed on a Si substrate.

Figure 3:
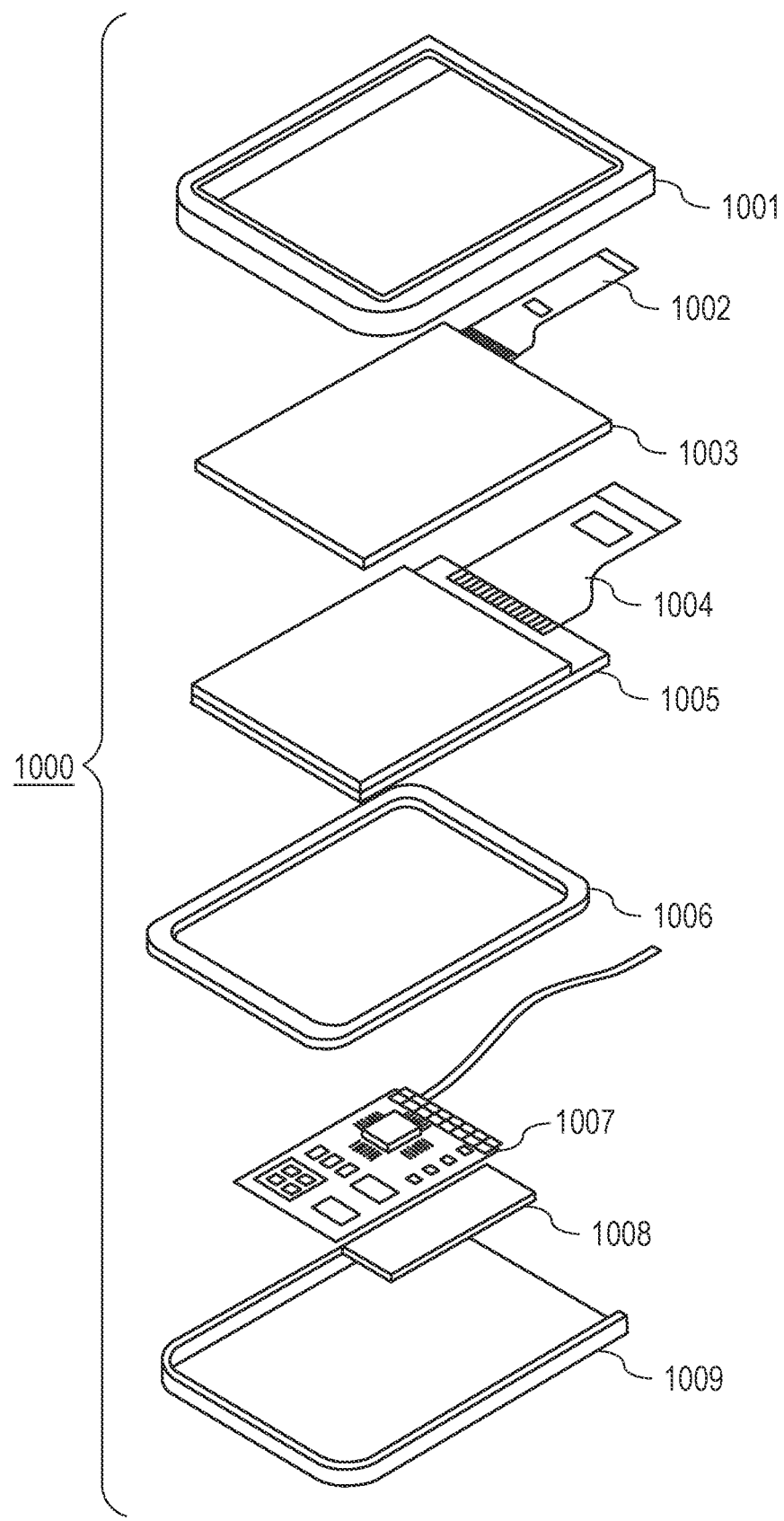
FIG. 3 schematically illustrates an example of a display apparatus according to an embodiment of the present disclosure.

FIG. 3 schematically illustrates an example of a display apparatus according to this embodiment. A display apparatus 1000 may include a touch panel 1003, a display panel 1005, a frame 1006, a circuit board 1007, and a battery 1008 between an upper cover 1001 and a lower cover 1009. Flexible printed circuits FPC 1002 and 1004 are connected to the touch panel 1003 and the display panel 1005, respectively. A transistor is printed on the circuit board 1007. The battery 1008 is not necessarily disposed if the display apparatus is not a mobile apparatus. Even if the display apparatus is a mobile apparatus, the battery 1008 may be disposed at a different position.

The display apparatus according to this embodiment may be used in a display unit of a photoelectric conversion apparatus such as an image pickup apparatus that includes an optical unit including a plurality of lenses and an image pickup element configured to receive light that has passed through the optical unit. The image pickup apparatus may include a display unit configured to display information obtained by the image pickup element. The display unit may be a display unit exposed to the outside of the image pickup apparatus or a display unit disposed in a viewfinder. The image pickup apparatus may be a digital camera or a digital video camera.

Figure 4A:
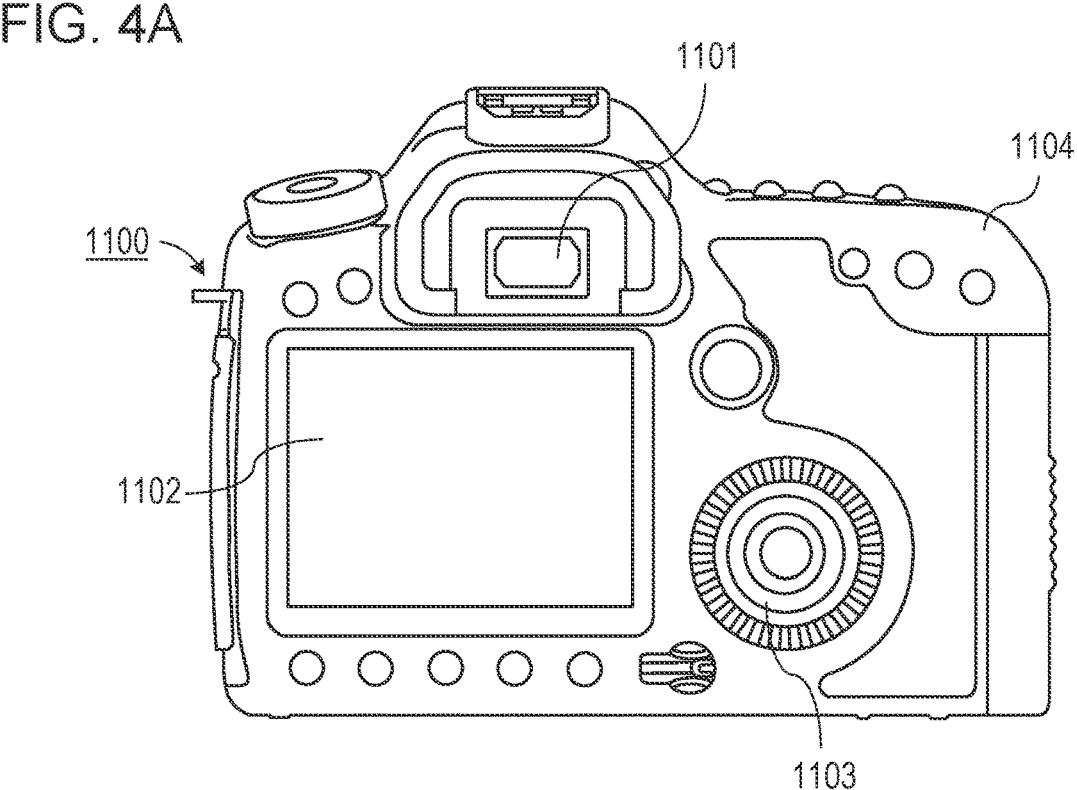
FIG. 4A schematically illustrates an example of an image pickup apparatus according to an embodiment of the present disclosure.

FIG. 4A schematically illustrates an example of an image pickup apparatus according to this embodiment. An image pickup apparatus 1100 may include a viewfinder 1101, a rear display 1102, an operating unit 1103, and a housing 1104. The viewfinder 1101 may include the display apparatus according to this embodiment. In this case, the display apparatus may display not only an image to be captured, but also environmental information, image capturing instructions, and the like. The environmental information may be, for example, the intensity of external light, the direction of external light, the moving speed of a subject, and the possibility that the subject is hidden by an object.

Since the timing appropriate for capturing an image is only a moment, the information is desirably displayed as quickly as possible. Therefore, the display apparatus including the organic light-emitting element according to this embodiment is suitably used. This is because the organic light-emitting element has a high response speed. The display apparatus including the organic light-emitting element can be more suitably used than these apparatuses and liquid crystal display apparatuses that are required to have a high display speed.

The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

The display apparatus according to this embodiment may include red, green, and blue color filters. The red, green, and blue color filters may be disposed in a delta arrangement.

The display apparatus according to this embodiment may be used in a display unit of an electronic apparatus such as a mobile terminal. The display unit may have both a display function and an operational function. Examples of the mobile terminal include cellular phones such as smartphones, tablet computers, and head-mounted displays.

Figure 4B:
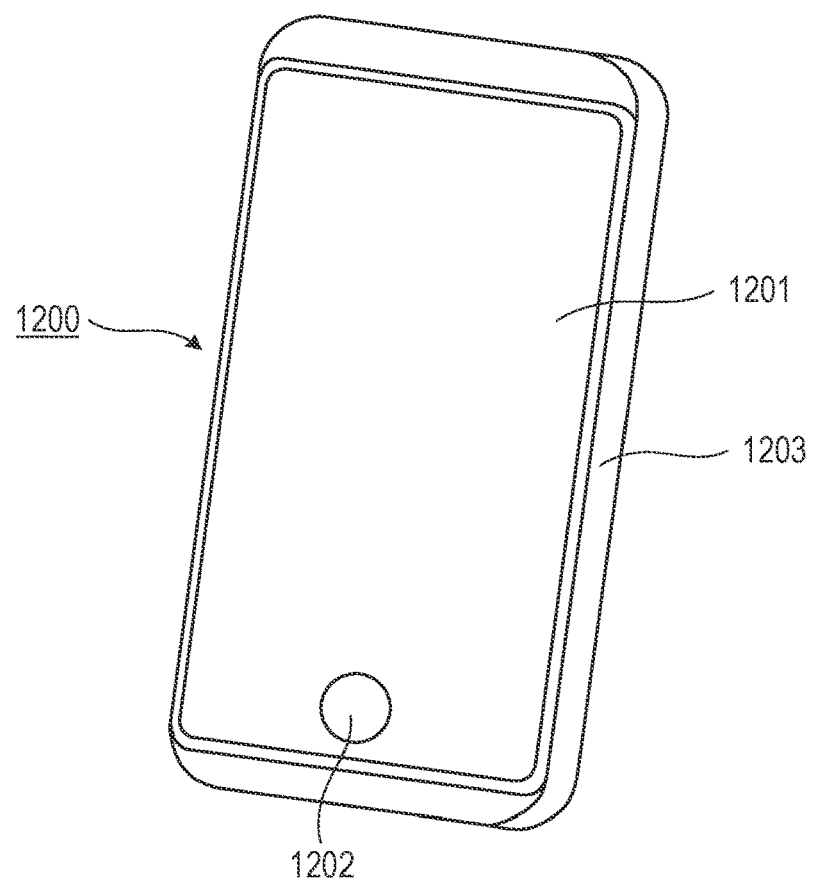
FIG. 4B schematically illustrates an example of an electronic apparatus according to an embodiment of the present disclosure.

FIG. 4B schematically illustrates an example of an electronic apparatus according to this embodiment. An electronic apparatus 1200 includes a display unit 1201, an operating unit 1202, and a housing 1203. The housing 1203 may include a circuit, a printed board including the circuit, a battery, and a communication unit. The operating unit 1202 may be a button or a touch panel response unit. The operating unit may be a biometric authentication unit that releases a lock through recognition of fingerprints. An electronic apparatus including a communication unit may be referred to as a communication apparatus.

Figure 5A:
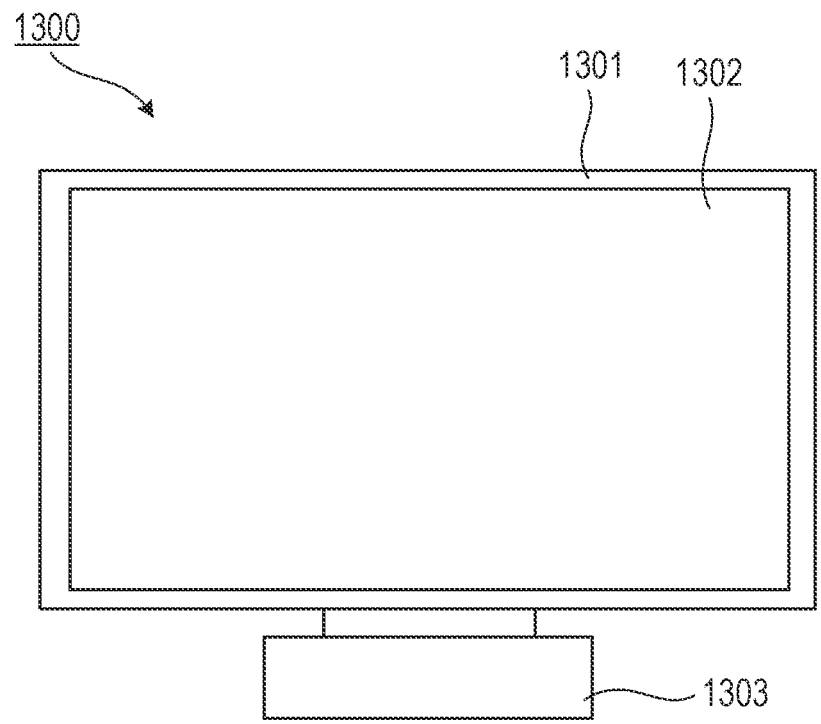
FIG. 5A schematically illustrates an example of a display apparatus according to an embodiment of the present disclosure.
Figure 5B:
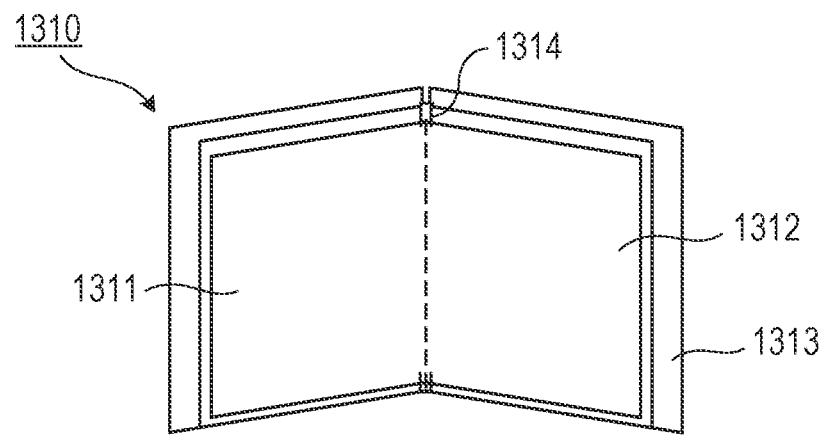
FIG. 5B schematically illustrates an example of a foldable display apparatus.

FIGS. 5A and 5B schematically illustrate examples of display apparatuses according to this embodiment. FIG. 5A illustrates a display apparatus such as a television monitor or a PC monitor. A display apparatus 1300 includes a frame 1301 and a display unit 1302. A light-emitting device according to this embodiment may be used for the display unit 1302. The display apparatus 1300 includes the frame 1301 and a base 1303 that supports the display unit 1302. The form of the base 1303 is not limited to that in FIG. 5A. The lower side of the frame 1301 may also serve as a base. The frame 1301 and the display unit 1302 may be curved. The radius of curvature may be 5000 mm or more and 6000 mm or less.

FIG. 5B schematically illustrates another example of the display apparatus according to this embodiment. A display apparatus 1310 in FIG. 5B is a so-called foldable display apparatus. The display apparatus 1310 includes a first display unit 1311, a second display unit 1312, a housing 1313, and a bending point 1314. The first display unit 1311 and the second display unit 1312 may include the light-emitting device according to this embodiment. The first display unit 1311 and the second display unit 1312 may constitute a single seamless display apparatus. The first display unit 1311 and the second display unit 1312 can be divided by the bending point. The first display unit 1311 and the second display unit 1312 may display different images or a single image may be displayed in a combination of the first and second display units.

Figure 6A:
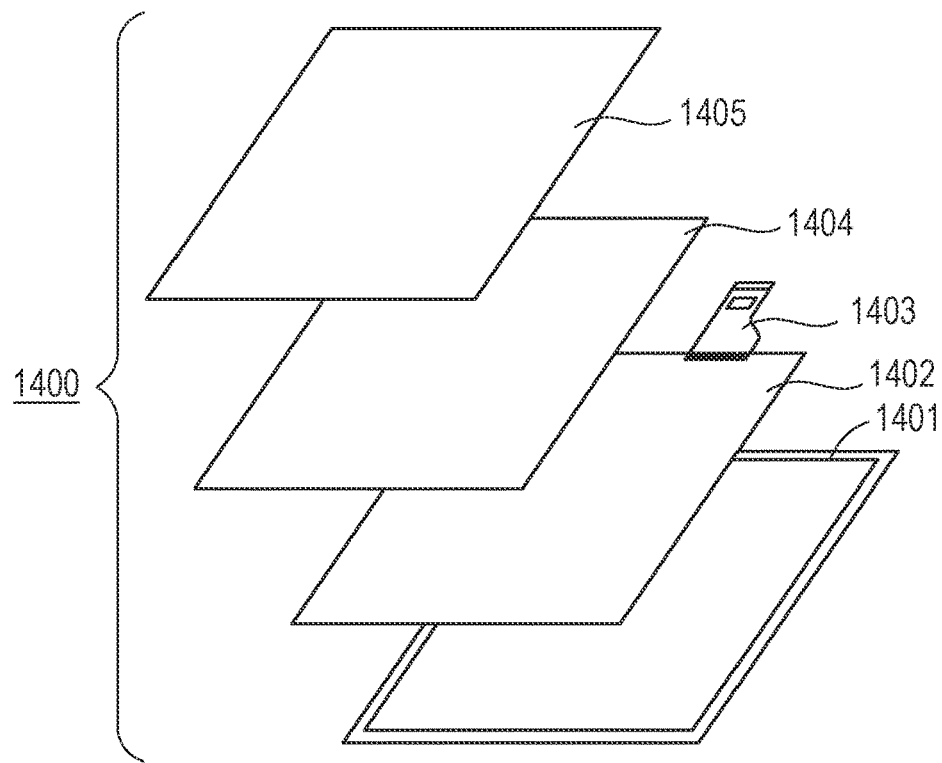
FIG. 6A schematically illustrates an example of a lighting apparatus according to an embodiment of the present disclosure.

FIG. 6A schematically illustrates an example of a lighting apparatus according to this embodiment. A lighting apparatus 1400 may include a housing 1401, a light source 1402, a circuit board 1403, and an optical filter 1404 and a light diffusion unit 1405 that transmit light emitted from the light source 1402. The light source 1402 may include the organic light-emitting element according to this embodiment. The optical filter 1404 may be a filter for improving the color rendering of the light source. The light diffusion unit 1405 used for lighting up or the like effectively diffuses light from the light source and allows the light to reach a wide area. The optical filter 1404 and the light diffusion unit 1405 may be disposed on the light-emitting side of the lighting apparatus. A cover may be optionally disposed on the outermost part.

The lighting apparatus is, for example, an apparatus that lights a room. The lighting apparatus may emit light of white, natural white, or any other color from blue to red. The lighting apparatus may include a light modulation circuit configured to modulate the light. The lighting apparatus may include the organic light-emitting element according to this embodiment and a power supply circuit connected to the organic light-emitting element. The power supply circuit is a circuit that converts an alternating voltage to a direct voltage. The color "white" has a color temperature of 4200 K and the color "natural white" has a color temperature of 5000 K. The lighting apparatus may include a color filter.

The lighting apparatus according to this embodiment may include a heat dissipation unit. The heat dissipation unit dissipates heat in the apparatus to the outside and is formed of, for example, a metal having a high specific heat or a liquid silicon.

Figure 6B:
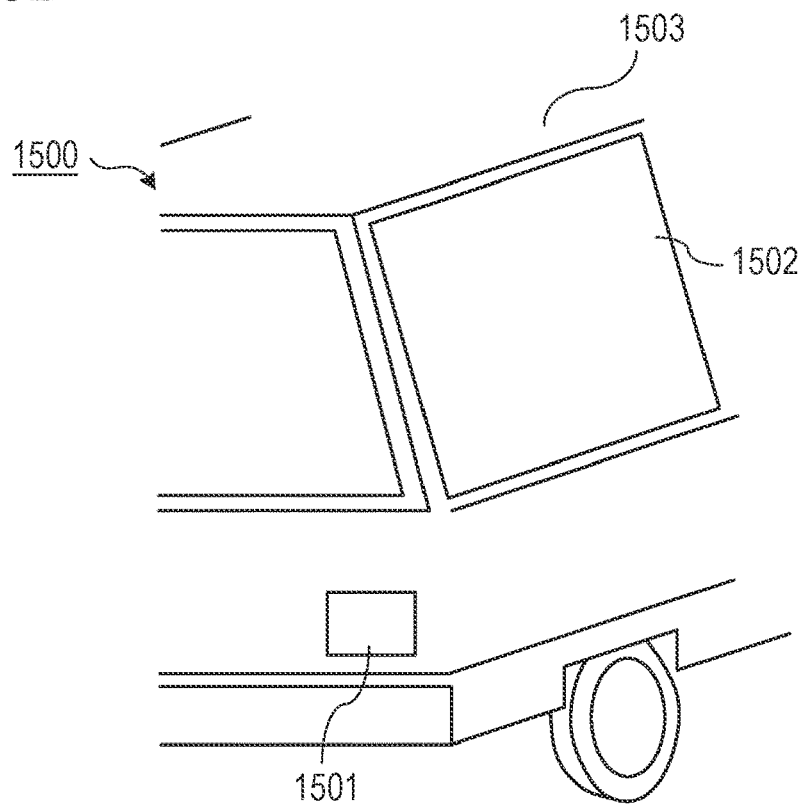
FIG. 6B schematically illustrates an example of an automobile including a lighting fixture for vehicles according to an embodiment of the present disclosure.

FIG. 6B schematically illustrates an automobile that is an example of a moving object according to this embodiment. The automobile includes a tail lamp that is an example of a lighting fixture. An automobile 1500 includes a tail lamp 1501, and the tail lamp may be lit through, for example, application of the brake.

The tail lamp 1501 may include the organic light-emitting element according to this embodiment. The tail lamp 1501 may include a protective member that protects the organic light-emitting element. The protective member may be made of any material as long as the protective member has a relatively high strength and transparency. The protective member may be made of polycarbonate or the like. The polycarbonate may be mixed with, for example, a furandicarboxylic acid derivative or an acrylonitrile derivative.

The automobile 1500 may include a car body 1503 and windows 1502 attached to the car body 1503. The windows 1502 may be transparent displays as long as the windows 1502 are not a front or rear window of the automobile. The transparent display may include the organic light-emitting element according to this embodiment. In this case, members, such as an electrode, included in the organic light-emitting element are formed of a transparent material.

The moving object according to this embodiment may be, for example, a ship, an aircraft, or a drone. The moving object may include a body and a lighting fixture disposed on the body. The lighting fixture may emit light for allowing the position of the body to be recognized. The lighting fixture may include the organic light-emitting element according to this embodiment.

Figure 7:
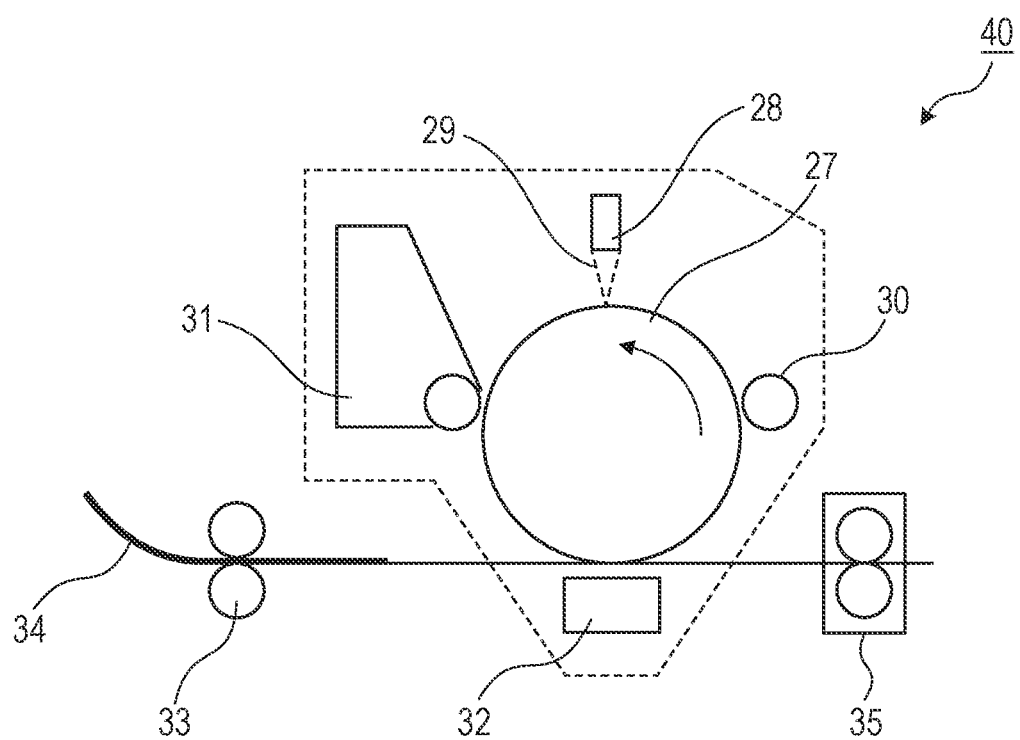
FIG. 7 schematically illustrates an example of an image forming apparatus according to an embodiment of the present disclosure.

FIG. 7 schematically illustrates an example of an image forming apparatus according to this embodiment. An image forming apparatus 40 is an electrophotographic image forming apparatus and includes a photosensitive member 27, an exposure light source 28, a developing unit 30, a charging unit 31, a transfer unit 32, conveyance rollers 33, and a fixing unit 35. Light 29 is emitted from the exposure light source 28, and an electrostatic latent image is formed on a surface of the photosensitive member 27. The exposure light source 28 includes the organic light-emitting element according to this embodiment. The developing unit 30 includes, for example, a toner. The charging unit 31 is configured to charge the photosensitive member 27. The transfer unit 32 is configured to transfer the developed image onto a recording medium 34. The conveyance rollers 33 are configured to convey the recording medium 34. The recording medium 34 is, for example, paper. The fixing unit 35 is configured to fix an image formed on the recording medium 34.

Figure 8A:
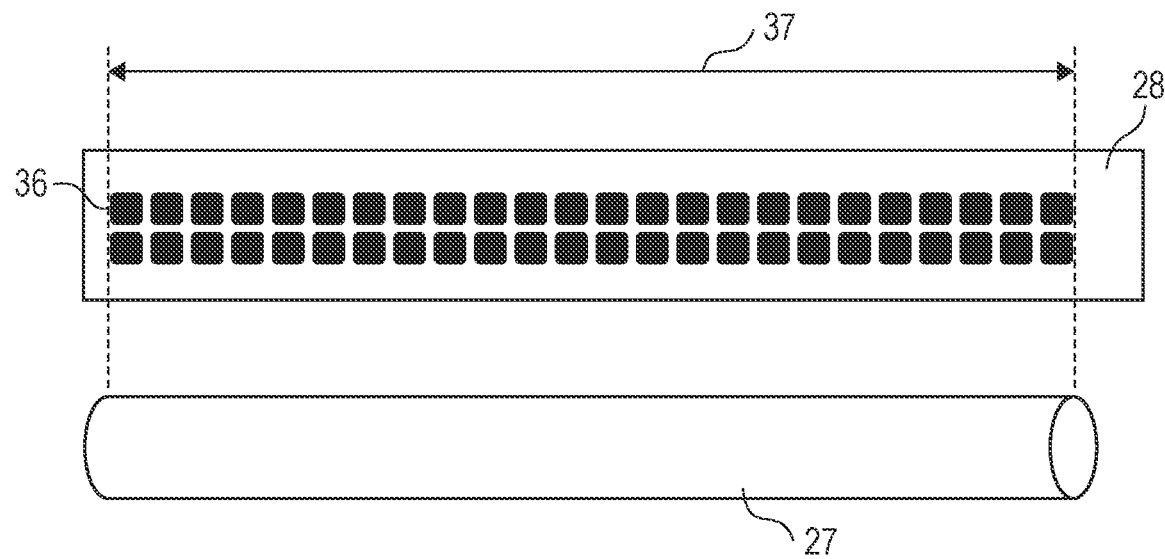
FIGS. 8A and 8B schematically illustrate examples of exposure light sources for an image forming apparatus according to an embodiment of the present disclosure.
Figure 8B:
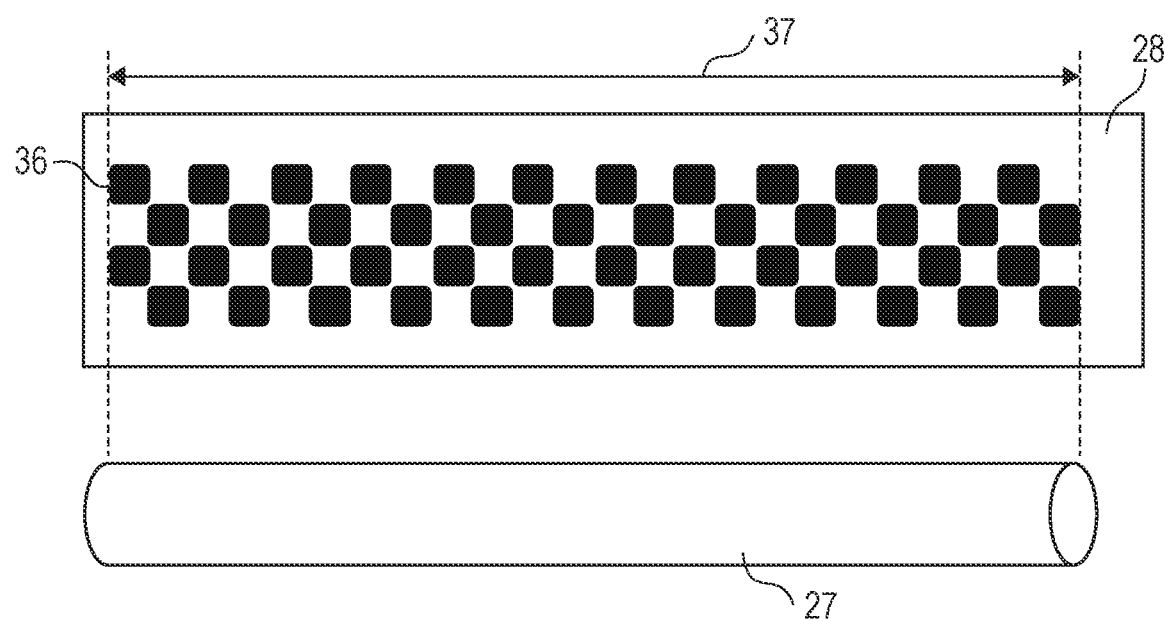

FIG. 8A and FIG. 8B schematically illustrate exposure light sources 28 in which a plurality of light-emitting units 36 are arranged on a long substrate. An arrow 37 indicates a row direction in which the organic light-emitting elements are arranged. This row direction is the same as the direction of the axis about which the photosensitive member 27 rotates. This direction can also be referred to as a longitudinal direction of the photosensitive member 27. FIG. 8A illustrates a state in which the light-emitting units 36 are arranged in the longitudinal direction of the photosensitive member 27. FIG. 8B illustrates a state in which the light-emitting units 36 are alternately arranged in a row direction in each of the first row and the second row, which is different from the state in FIG. 8A. In the first row and the second row, the light-emitting units 36 are arranged in different positions in a column direction. In the first row, the plurality of light-emitting units 36 are arranged apart from each other. In the second row, the light-emitting units 36 are arranged at positions corresponding to spacings between the light-emitting units 36 in the first row. In other words, the plurality of light-emitting units 36 are also arranged apart from each other in the column direction. The arrangement in FIG. 8B can also be referred to as, for example, a lattice arrangement, a staggered arrangement, or a checkered arrangement.

As described above, use of an apparatus including the organic light-emitting element according to this embodiment allows stable display with a good image quality for a long time.

EXAMPLES

Hereafter, the present disclosure will be described based on Examples. However, the present invention is not limited thereto.

Example 1 (Synthesis of Exemplary Compound A1)

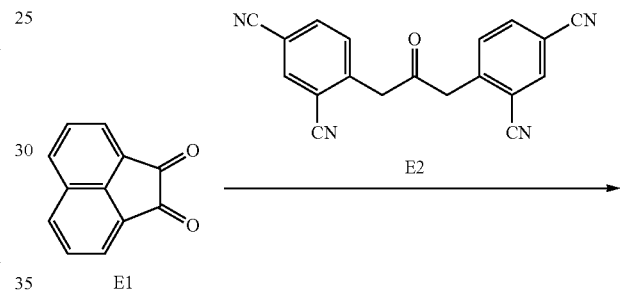

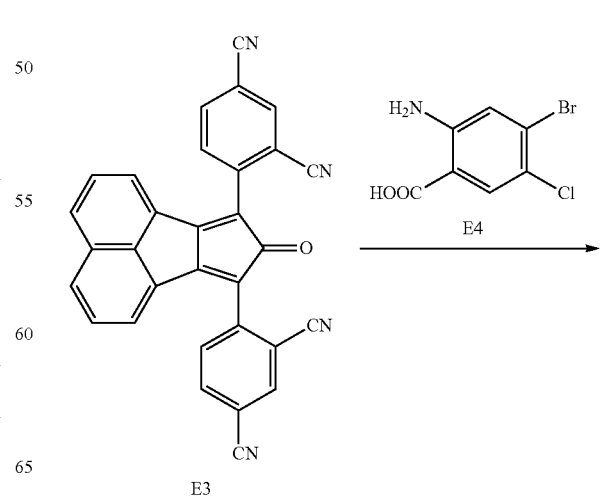

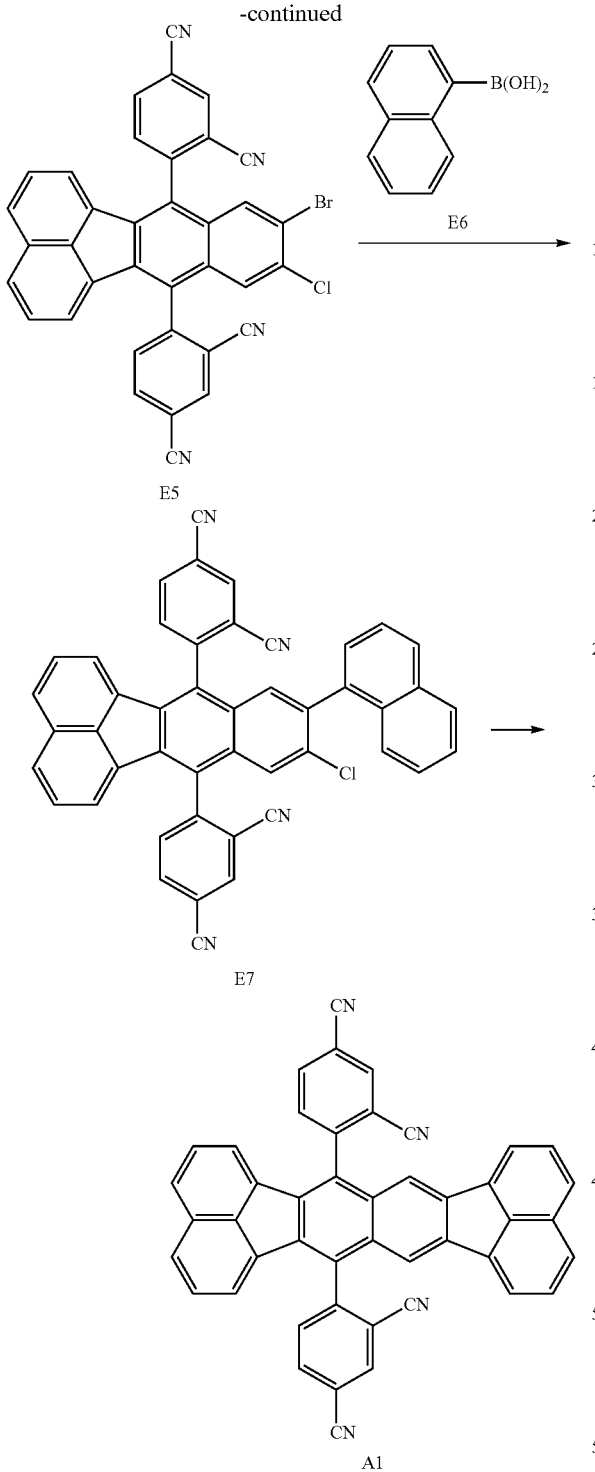

(1) Synthesis of Compound E3

The following reagents and solvent were charged into a 200 ml recovery flask.
Compound E1: 1.82 g (10 mmol)
Compound E2: 3.10 g (10 mmol)
Ethanol: 100 ml Subsequently, the reaction solution was heated to 70° C. in a nitrogen stream, and a KOH ethanol solution was added dropwise thereto. Furthermore, stirring was performed at this temperature (70° C.) for 6 hours. After the completion of the reaction, water was added and the resulting precipitate was separated. The separated product was washed by dispersion with methanol to obtain 3.42 g of a dark gray compound E3 (yield: 75%).

(2) Synthesis of Compound E5

The following reagents and solvent were charged into a 100 ml recovery flask.
Compound E3: 3.19 g (7 mmol)
Compound E4: 2.25 g (9 mmol)
Isoamyl nitrite: 1.05 g (9 mmol)
Toluene: 40 ml Subsequently, the reaction solution was heated to 110° C. in a nitrogen stream, and stirring was performed at this temperature (110° C.) for 3 hours. After the completion of the reaction, washing with 40 ml of water was performed twice. The organic layer was washed with a saturated saline solution and dried with magnesium sulfate. Then, after the resulting solution was separated, the filtrate was concentrated to obtain a brown liquid. The liquid was purified by column chromatography (chloroform/heptane=1:4) and then recrystallized with chloroform/methanol to obtain 3.67 g of a yellow crystalline compound E5 (yield: 85%).

(3) Synthesis of Compound E7

The following reagents and solvents were charged into a 200 ml recovery flask.
Compound E5: 1.85 g (3 mmol)
Compound E6: 0.51 g (3 mmol)
Pd(PPh$_3$)$_4$: 0.06 g
Toluene: 50 ml
Ethanol: 20 ml
2M-sodium carbonate aqueous solution: 50 ml Subsequently, the reaction solution was heated to 80° C. in a nitrogen stream, and stirring was performed at this temperature (80° C.) for 6 hours. After the completion of the reaction, water was added and liquid separation was performed. The resulting product was dissolved in chloroform, purified by column chromatography (chloroform), and then recrystallized with chloroform/methanol to obtain 1.49 g of a yellow crystalline compound E7 (yield: 75%).

(4) Synthesis of Exemplary Compound A1

The following reagents and solvent were charged into a 20 ml recovery flask.
Compound E7: 665 mg (1 mmol)
Pd(dba)$_2$: 58 mg
P(Cy)$_3$ (tricyclohexylphosphine): 84 mg
Potassium acetate: 196 mg
DMF: 10 ml Subsequently, the reaction solution was heated to 145° C. in a nitrogen stream, and stirring was performed at this temperature (145° C.) for 6 hours. After the completion of the reaction, ethanol was added to precipitate a crystal. The crystal was separated and sequentially washed by dispersion with water, ethanol, and heptane. Subsequently, the resulting purple crystal was dissolved in toluene by heating and then subjected to hot filtration and recrystallization with toluene/methanol to obtain 0.48 g of a yellow exemplary compound A1 (yield: 78%).

This compound was confirmed to have a purity of 99% or more, as measured by HPLC.

The exemplary compound A1 was subjected to mass spectrometry using MALDI-TOF-MS (Autoflex LRF manufactured by Bruker).

MALDI-TOF-MS

Measured value: m/z=628.85, Calculated value: $C_{46}H_{20}N_4$=628.69

Example 2 (Synthesis of Exemplary Compound A7)

An exemplary compound A7 was obtained by the same method as in Example 1, except that the following compound E8 was used instead of the compound E2 and the following compound E9 was used instead of the compound E6.

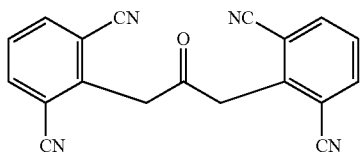
E8

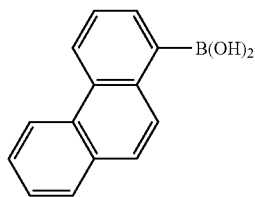
E9

The purity of the obtained compound was evaluated by HPLC. The purity was 98% or more.

Furthermore, the compound was subjected to mass spectrometry using MALDI-TOF-MS (Autoflex LRF manufactured by Bruker).

MALDI-TOF-MS

Measured value: m/z=678.43, Calculated value: $C_{50}H_{22}N_4$=678.75

Example 3 (Synthesis of Exemplary Compound B5)

An exemplary compound B5 was obtained by the same method as in Example 1, except that the following compound E10 was used instead of the compound E1, the following compound E11 was used instead of the compound E4, and the following compound E12 was used instead of the compound E6.

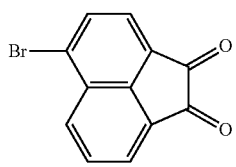
E10

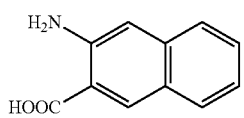
E11

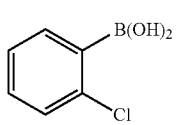
E12

The purity of the obtained compound was evaluated by HPLC. The purity was 98% or more.

Furthermore, the compound was subjected to mass spectrometry using MALDI-TOF-MS (Autoflex LRF manufactured by Bruker).

MALDI-TOF-MS

Measured value: m/z=628.02, Calculated value: $C_{46}H_{20}N_4$=628.69

Example 4 (Synthesis of Exemplary Compound C13)

An exemplary compound C13 was obtained by the same method as in Example 1, except that the following compound E13 was used instead of the compound E1, the following compound E14 was used instead of the compound E2, and the following compound E15 was used instead of the compound E6.

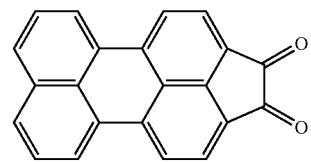
E13

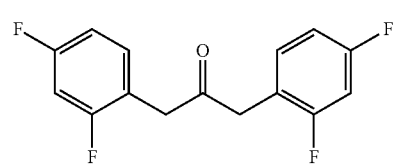
E14

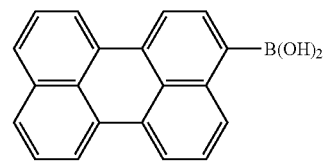
E15

The purity of the obtained compound was evaluated by HPLC. The purity was 98% or more.

Furthermore, the compound was subjected to mass spectrometry using MALDI-TOF-MS (Autoflex LRF manufactured by Bruker).

MALDI-TOF-MS

Measured value: m/z=848.22, Calculated value: $C_{62}H_{28}F_4$=848.90

Comparative Example 1 (Synthesis of Comparative Compound (9))

A comparative compound (9) below was obtained by the same method as in Example 4, except that the following compound E16 was used instead of the compound E14.

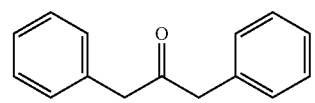
E16

-continued

Comparative compound (9)

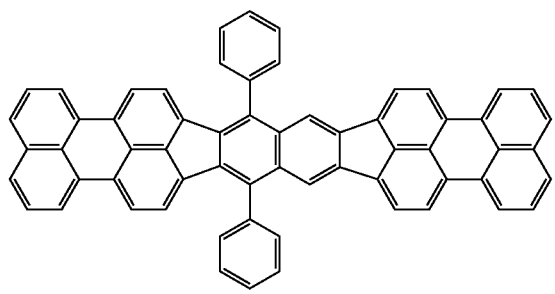

The exemplary compound C13 and the comparative compound (9) have the same basic skeleton constituted by the ring A and the same substituent constituted by the ring B, but are different in terms of the presence or absence of electron withdrawing group Q. To evaluate the sublimability of these compounds, the difference between the decomposition temperature and the sublimation temperature was determined. The difference in temperature was 10° C. in the comparative compound (9) whereas the difference in temperature was 100° C. in the exemplary compound C13. Since the exemplary compound C13 has a larger difference between the decomposition temperature and the sublimation temperature, the exemplary compound C13 has a large temperature margin in sublimation purification and thus has high sublimability.

Example 5 (Synthesis of Exemplary Compound A20)

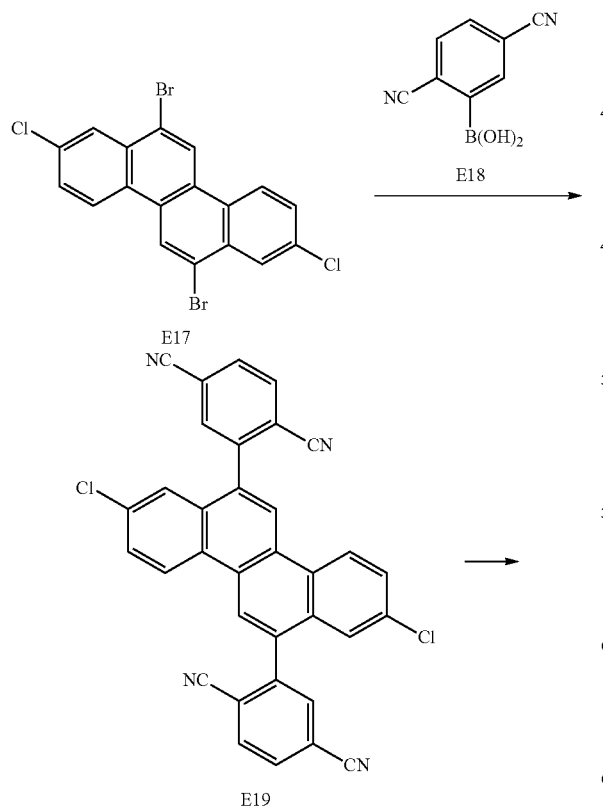

-continued

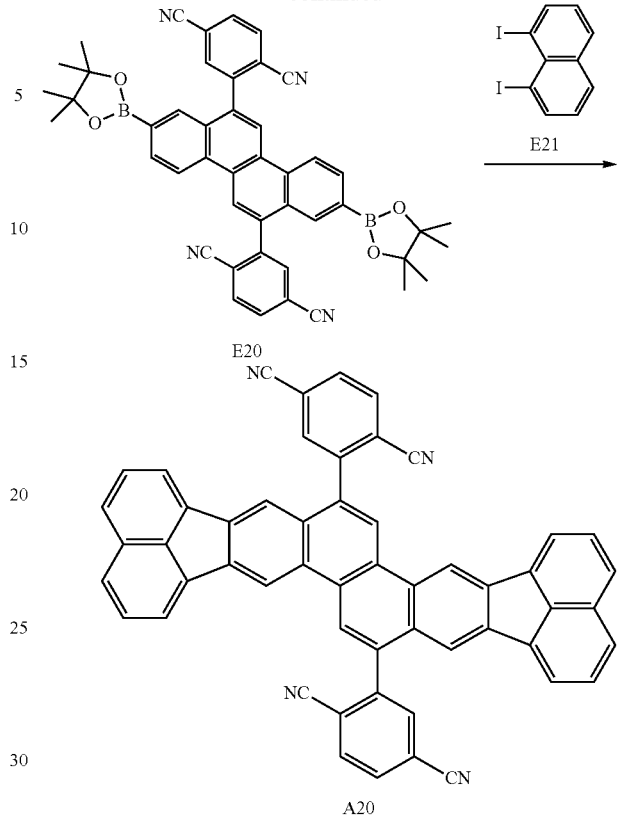

(1) Synthesis of Compound E19

The following reagents and solvents were charged into a 1000 ml recovery flask.
Compound E17: 4.55 g (10 mmol)
Compound E18: 3.78 g (22 mmol)
Pd(PPh$_3$)$_4$: 0.1 g
Toluene: 250 ml
Ethanol: 120 ml
2M-sodium carbonate aqueous solution: 120 ml Subsequently, the reaction solution was heated to 80° C. in a nitrogen stream, and stirring was performed at this temperature (80° C.) for 6 hours. After the completion of the reaction, water was added and liquid separation was performed. The resulting product was dissolved in chloroform, purified by column chromatography (chloroform), and then recrystallized with chloroform/methanol to obtain 4.12 g of a light yellow crystalline compound E19 (yield: 75%).

(2) Synthesis of Compound E20

The following reagents and solvent were charged into a 500 ml recovery flask.
Compound E19: 3.84 g (7 mmol)
bis(pinacolborane): 4.05 g (16 mmol)
Pd(dba)$_2$: 402 mg
P(Cy)$_3$ (tricyclohexylphosphine): 588 mg
Toluene: 20 ml Subsequently, the reaction solution was heated to 110° C. in a nitrogen stream, and stirring was performed at this temperature (110° C.) for 3 hours. After the completion of the reaction, washing with 40 ml of water was performed twice. The organic layer was washed with a saturated saline solution and dried with magnesium sulfate. Then, after the resulting solution was separated, the filtrate was concentrated to obtain a brown liquid. The liquid was purified by column chromatography (toluene) and then washed by dispersion with heptane to obtain 4.35 g of a brownish-white solid E20 (yield: 85%).

(3) Synthesis of Exemplary Compound A20

The following reagents and solvent were charged into a 20 ml recovery flask.
Compound E20: 732 mg (1 mmol)
Compound E21: 760 mg (2 mmol)
Pd(dba)$_2$: 58 mg
P(Cy)$_3$ (tricyclohexylphosphine): 84 mg
Potassium acetate: 196 mg
DMF: 10 ml Subsequently, the reaction solution was heated to 145° C. in a nitrogen stream, and stirring was performed at this temperature (145° C.) for 6 hours. After the completion of the reaction, ethanol was added to precipitate a crystal. Then, the crystal was separated and sequentially washed by dispersion with water, ethanol, and heptane. Subsequently, the resulting purple crystal was dissolved in toluene by heating and then subjected to hot filtration and recrystallization with toluene/methanol to obtain 0.44 g of a yellow exemplary compound A20 (yield: 60%).

The compound was confirmed to have a purity of 99% or more, as measured by HPLC.

The exemplary compound A1 was subjected to mass spectrometry using MALDI-TOF-MS (Autoflex LRF manufactured by Bruker).
MALDI-TOF-MS
Measured value: m/z=728.85, Calculated value: $C_{54}H_{24}N_4$=728.81

Comparative Example 2 (Synthesis of Comparative Compound (10))

A comparative compound (10) below was obtained by the same method as in Example 5, except that the following compound E21 was used instead of the compound E18.

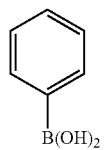

E21

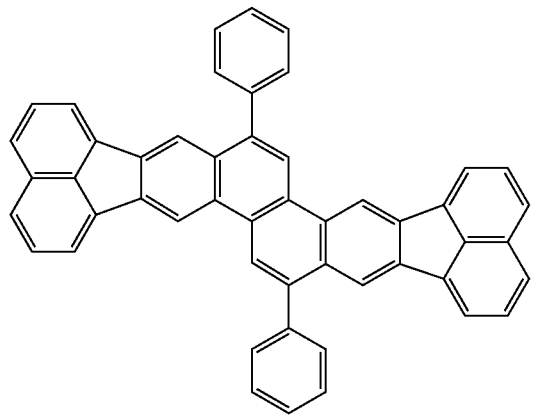

Comparative compound (10)

The exemplary compound A20 and the comparative compound (10) have the same basic skeleton constituted by the ring A and the same substituent constituted by the ring B, but are different in terms of the presence or absence of electron withdrawing group Q. To evaluate the oxidation potential of these compounds, CV measurement was performed. The oxidation potential was 1.05 V in the comparative compound (10) whereas the oxidation potential was 1.13 V in the exemplary compound A20. This shows that the exemplary compound A20 is a compound having higher oxidation stability.

Example 6

In this Example, a bottom-emission organic EL element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process. Subsequently, the organic EL layers and the electrode layer shown in Table 4 were successively formed on the ITO substrate by performing vacuum vapor deposition through resistance heating in a vacuum chamber at 1.33×10$^{-4}$ Pa. At this time, the electrode area of a counter electrode (metal electrode layer, cathode) was set to 3 mm$^2$.

TABLE 4

| | Material | | | Thickness (nm) |
|---|---|---|---|---|
| Cathode | Al | | | 100 |
| Electron injection layer (EIL) | LiF | | | 1 |
| Electron transport layer (ETL) | ET2 | | | 30 |
| Hole blocking layer (HBL) | ET13 | | | 10 |
| Light-emitting layer (EML) | Host Guest | EM3 A1 | Mass ratio EM3:A1 = 99:1 | 30 |
| Electron blocking layer (EBL) | HT12 | | | 10 |
| Hole transport layer (HTL) | HT3 | | | 30 |
| Hole injection layer (HIL) | HT16 | | | 10 |

The characteristics of the obtained element were measured and evaluated. The external quantum efficiency (E.Q.E) was 5.8%. The light-emitting element had a maximum emission wavelength of 453 nm and emitted blue light with a chromaticity of (X, Y)=(0.15, 0.17). For the measurement method, specifically, the current-voltage characteristics were measured with a microammeter 4140B manufactured by Hewlett-Packard Company, and the emission luminance was measured with a BM7 manufactured by TOPCON Corporation. Furthermore, a continuous driving test at a current density of 100 mA/cm$^2$ was performed to measure a time (LT90) taken when the luminance decrease reached 10%. The time was more than 100 hours. Table 5 shows the measurement results.

Examples 7 to 14 and Comparative Examples 5 And 4

Organic light-emitting elements were produced by the same method as in Example 6, except that the compounds were appropriately changed to those listed in Table 5. The characteristics of the obtained elements were measured and evaluated in the same manner as in Example 6. Table shows the measurement results.

TABLE 5

|  | HIL | HTL | EBL | EML Host | EML Guest | HBL | ETL | E.Q.E [%] | LT90 [h] | (x, y) |
|---|---|---|---|---|---|---|---|---|---|---|
| Example 6 | HT16 | HT3 | HT11 | EM3 | A1 | ET14 | ET2 | 5.8 | 120 | (0.15, 0.17) |
| Example 7 | HT2 | HT2 | HT8 | EM4 | A2 | ET12 | ET2 | 5.8 | 130 | (0.15, 0.18) |
| Example 8 | HT2 | HT2 | HT8 | EM4 | A7 | ET12 | ET2 | 5.9 | 120 | (0.15, 0.17) |
| Example 9 | HT2 | HT2 | HT11 | EM4 | A24 | ET10 | ET5 | 6.2 | 115 | (0.14, 0.15) |
| Example 10 | HT2 | HT2 | HT11 | EM5 | A10 | ET12 | ET3 | 6.0 | 105 | (0.14, 0.17) |
| Example 11 | HT16 | HT6 | HT11 | EM5 | A19 | ET13 | ET2 | 5.7 | 115 | (0.13, 0.13) |
| Example 12 | HT16 | HT6 | HT8 | EM6 | A11 | ET12 | ET2 | 5.9 | 110 | (0.15, 0.16) |
| Example 13 | HT16 | HT6 | HT11 | EM6 | A13 | ET15 | ET5 | 5.8 | 110 | (0.15, 0.18) |
| Example 14 | HT16 | HT6 | HT8 | EM | A3 | ET17 | ET5 | 5.9 | 110 | (0.15, 0.18) |
| Comparative Example 3 | HT16 | HT3 | HT11 | EM3 | Comparative compound (1) | ET12 | ET2 | 5.7 | 95 | (0.18, 0.32) |
| Comparative Example 4 | HT16 | HT3 | HT11 | EM3 | Comparative compound (10) | ET12 | ET2 | 5.5 | 70 | (0.15, 0.17) |

Table 5 shows that the organic light-emitting element including the comparative compound (1) emitted sky blue light with a chromaticity of (X, Y)=(0.18, 0.32). This is because the guest is the comparative compound (1) having a long emission wavelength. In the organic light-emitting element including the comparative compound (10), the time taken when the luminance decrease reached 10% was 70 hours. This is because the guest was the comparative compound (10) having a low oxidation potential. In contrast, the element including the organic compound according to an embodiment of the present disclosure had good blue light-emitting properties and high durability.

Example 15

In this Example, a top-emission organic EL element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

A Ti film having a thickness of 40 nm was formed on a glass substrate by a sputtering method and patterned by photolithography to form an anode. At this time, the electrode area of a counter electrode (metal electrode layer, cathode) was set to 3 mm$^2$. Subsequently, the cleaned substrate on which the electrode had been formed and materials were placed in a vacuum evaporation system (manufactured by ULVAC, Inc.), and the system was evacuated to a pressure of $1.33\times10^{-4}$ Pa ($1\times10^{-6}$ Torr) and then UV/ozone cleaning was performed. Subsequently, layers shown in Table 6 were formed. Lastly, sealing was performed in a nitrogen atmosphere.

TABLE 6

|  |  | Material | Thickness (nm) |
|---|---|---|---|
| Cathode | Mg | Mass ratio | 10 |
|  | Ag | Mg:Ag = 50:50 |  |
| Electron injection layer (EIL) | LiF |  | 1 |
| Electron transport layer (ETL) | ET2 |  | 30 |
| Hole blocking layer (HBL) | ET12 |  | 70 |

TABLE 6-continued

|  |  | Material | Thickness (nm) |
|---|---|---|---|
| Second light-emitting layer (2nd EML) | Second host | EM5 | Mass ratio | 10 |
|  | Second guest (blue dopant) | A1 | EM5:A1 = 99.0:1.0 |  |
| First light-emitting layer (1st EML) | First host | EM5 | Mass ratio | 10 |
|  | First guest (red dopant) | RD5 | EM5:RD5:GD10 = 96.5:0.5:3.0 |  |
|  | Third guest (green dopant) | GD10 |  |  |
| Electron blocking layer (EBL) |  | HT7 |  | 10 |
| Hole transport layer (HTL) |  | HT2 |  | 20 |
| Hole injection layer (HIL) |  | HT16 |  | 5 |

The characteristics of the obtained element were measured and evaluated. The obtained element exhibited good white light emission. Furthermore, a continuous driving test at an initial luminance of 2000 cd/m$^2$ was performed to measure a luminance decrease after 100 hours. The luminance decrease was 12%.

Examples 16 to 24 and Comparative Example 5

Organic light-emitting elements were produced by the same method as in Example 15, except that the compounds were appropriately changed to those listed in Table 7. The characteristics of the obtained elements were measured and evaluated in the same manner as in Example 15. Table 7 shows the measurement results.

TABLE 7

|  | 1st EML | | | 2nd EML | | Luminance decrease [%] |
|---|---|---|---|---|---|---|
|  | First host | First guest | Third guest | Second host | Second guest |  |
| Example 16 | EM5 | RD5 | GD10 | EM5 | A1 | 12 |
| Example 17 | EM1 | RD5 | GD9 | EM1 | A24 | 10 |
| Example 18 | EM1 | RD1 | GD4 | EM5 | A18 | 15 |
| Example 19 | EM4 | C20 | GD7 | EM6 | A7 | 20 |
| Example 20 | EM4 | RD7 | GD10 | EM6 | A2 | 12 |
| Example 21 | EM16 | RD1 | B6 | EM1 | BD9 | 15 |
| Example 22 | EM17 | RD5 | B5 | EM5 | BD1 | 18 |

TABLE 7-continued

| | 1st EML | | | 2nd EML | | Luminance decrease [%] |
|---|---|---|---|---|---|---|
| | First host | First guest | Third guest | Second host | Second guest | |
| Example 23 | EM1 | RD5 | GD10 | EM5 | A23 | 15 |
| Example 24 | EM2 | RD6 | GD11 | EM5 | A45 | 20 |
| Comparative Example 5 | EM5 | Comparative compound (9) | GD10 | EM5 | BD6 | 30 |

Table 7 shows that the organic light-emitting element including the comparative compound (9) had aluminance decrease of 30%. This is because the guest is the comparative compound (9) having low sublimability.

The organic compound according to an embodiment of the present disclosure has a high oxidation potential and high chemical stability. The organic compound also has high sublimability. Therefore, an organic light-emitting element having high driving durability can be provided by using this organic compound.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-162082, filed Sep. 5, 2019 which is hereby incorporated by reference herein in its entirety.

What is claimed is:
1. An organic compound represented by formula [1],

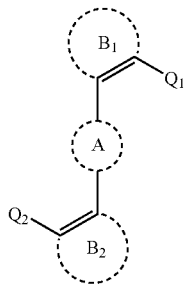

[1]

wherein ring A is any one of FF7, FF8, FF9, FF10, FF12, FF13, or FF14 and optionally has, as a substituent, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, or a silyl group, rings $B_1$ and $B_2$ are aromatic hydrocarbon rings having 6 to 18 carbon atoms, the ring $B_1$ has two or more electron withdrawing groups, and $Q_1$ represents one of the electron withdrawing groups of the ring $B_1$, is a cyano group and is located at an ortho position of the ring $B_1$ with respect to the ring A, and the ring $B_2$ has two or more electron withdrawing groups, and $Q_2$ represents one of the electron withdrawing groups of the ring $B_2$, is a cyano group and is located at an ortho position of the ring $B_2$ with respect to the ring A

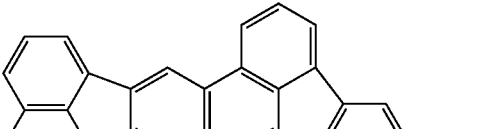

FF7

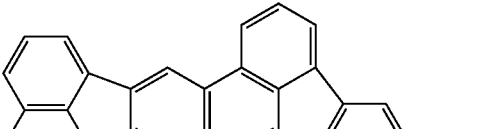

FF8

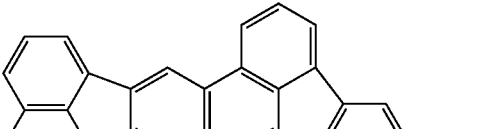

FF9

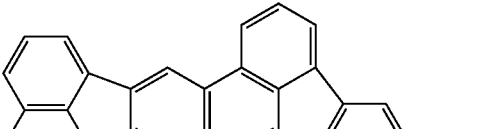

FF10

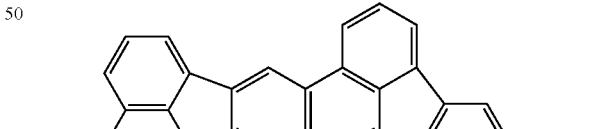

FF12

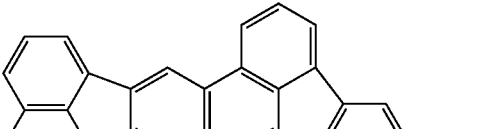

FF13

-continued

FF14

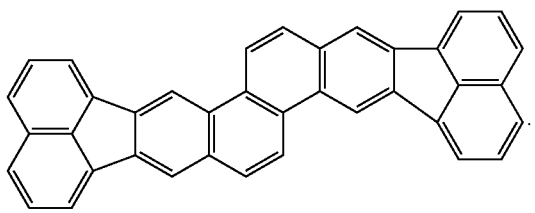

2. The organic compound according to claim 1, wherein the ring A is FF12 or FF14.

3. The organic compound according to claim 1,
wherein the ring A has a fluoranthene skeleton represented by formula [2] or a benzo(k)fluoranthene skeleton represented by formula [3], and
the rings $B_1$ and $B_2$ bond to the ring A at any one of positions * in the formula [2] or [3]

[2]

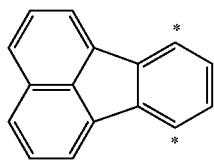

[3]

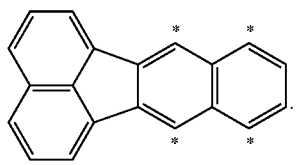

4. The organic compound according to claim 1, wherein the ring $B_1$ and the ring $B_2$ have the same structure, and $Q_1$ and $Q_2$ represent the same electron withdrawing group.

5. The organic compound according to claim 1, wherein the rings $B_1$ and $B_2$ are any one of a benzene ring and a naphthalene ring.

6. The organic compound according to claim 1, wherein one or more of the two or more withdrawing groups that the ring $B_1$ has, other than $Q_1$, is selected from a group consisting of a fluorine atom, a trifluoromethyl group, and a cyano group, and one or more of the two or more withdrawing groups that the ring $B_2$ has, other than $Q_2$, is selected from a group consisting of a fluorine atom, a trifluoromethyl group, and a cyano group.

7. The organic compound according to claim 1, wherein the two or more withdrawing groups that the ring $B_1$ has are cyano groups, and the two or more withdrawing groups that the ring $B_2$ has are cyano groups.

8. The organic compound according to claim 1, wherein when a substituent is further introduced to the alkyl group, the alkoxy group, the amino group, the aryl group, the heterocyclic group, and the aryloxy group, the substituent represents alkyl group, aralkyl group, aryl group, heterocyclic group, amino group, alkoxy group, aryloxy group, halogen atom, or cyano group.

9. An organic light-emitting element comprising:
an anode;
a cathode; and
an organic compound layer disposed between the anode and the cathode,
wherein the organic compound layer comprises one or more layers, and
at least one layer of the one or more layers includes the organic compound according to claim 1.

10. The organic light-emitting element according to claim 9, wherein the layer including the organic compound is a light-emitting layer.

11. The organic light-emitting element according to claim 10,
wherein the organic compound layer further includes another light-emitting layer disposed together with the light-emitting layer so as to form a multilayer structure, and
the other light-emitting layer emits light having a color different from a color of light emitted from the light-emitting layer.

12. The organic light-emitting element according to claim 11, wherein the organic light-emitting element emits white light.

13. A display apparatus comprising a plurality of pixels, wherein at least one of the plurality of pixels includes the organic light-emitting element according to claim 9 and a transistor connected to the organic light-emitting element.

14. A photoelectric conversion apparatus comprising:
an optical unit including a plurality of lenses;
an image pickup element that receives light which has passed through the optical unit; and
a display unit that displays an image captured by the image pickup element, wherein the display unit includes the organic light-emitting element according to claim 9.

15. An electronic apparatus comprising:
a display unit including the organic light-emitting element according to claim 9;
a housing in which the display unit is disposed; and
a communication unit that is disposed in the housing and communicates with an external unit.

16. A lighting apparatus comprising:
a light source including the organic light-emitting element according to claim 9; and
a light diffusion unit or an optical filter that transmits light emitted from the light source.

17. A moving object comprising:
a lighting fixture including the organic light-emitting element according to claim 9; and
a body on which the lighting fixture is disposed.

18. An exposure light source of an electrophotographic image forming apparatus, comprising the organic light-emitting element according to claim 9.

* * * * *